United States Patent
Brooks et al.

(10) Patent No.: US 8,927,585 B2
(45) Date of Patent: *Jan. 6, 2015

(54) TRPV4 ANTAGONISTS

(75) Inventors: Carl Brooks, King of Prussia, PA (US); Mui Cheung, King of Prussia, PA (US); Krista B. Goodman, King of Prussia, PA (US); Marlys Hammond, Littleton, CO (US)

(73) Assignee: GlaxoSmithKline Intellectual Property (NO.2) Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/125,367

(22) PCT Filed: Jun. 15, 2012

(86) PCT No.: PCT/US2012/042603
§ 371 (c)(1),
(2), (4) Date: Dec. 11, 2013

(87) PCT Pub. No.: WO2012/174340
PCT Pub. Date: Dec. 20, 2012

(65) Prior Publication Data
US 2014/0135369 A1    May 15, 2014

Related U.S. Application Data

(60) Provisional application No. 61/498,099, filed on Jun. 17, 2011.

(51) Int. Cl.
*C07D 413/06* (2006.01)
*C07D 413/14* (2006.01)

(52) U.S. Cl.
CPC ............ *C07D 413/14* (2013.01); *C07D 413/06* (2013.01)
USPC .......................................... 514/376; 548/216

(58) Field of Classification Search
CPC ... C07D 209/04; C07D 235/04; C07D 263/08
USPC ................... 548/216, 229; 514/375
See application file for complete search history.

(56) References Cited

U.S. PATENT DOCUMENTS

| | | |
|---|---|---|
| 2002/0065266 A1 | 5/2002 | Jensen et al. |
| 2005/0137202 A1 | 6/2005 | Matsuoka et al. |
| 2009/0042897 A1 | 2/2009 | Bentley et al. |
| 2009/0270375 A1 | 10/2009 | Hubschwerlen et al. |
| 2010/0216821 A1 | 8/2010 | Barton et al. |
| 2014/0113916 A1* | 4/2014 | Brooks et al. .......... 514/256 |
| 2014/0121206 A1* | 5/2014 | Brooks et al. .......... 514/234.5 |

FOREIGN PATENT DOCUMENTS

| | | |
|---|---|---|
| WO | WO2012174342 | 12/2012 |
| WO | WO2013012500 | 1/2013 |

* cited by examiner

*Primary Examiner* — Kamal Saeed
(74) *Attorney, Agent, or Firm* — Linda E. Hall; John L. Lemanowicz

(57) ABSTRACT

The present invention relates to spirocarbamate analogs, pharmaceutical compositions containing them and their use as TRPV4 antagonists.

9 Claims, No Drawings

TRPV4 ANTAGONISTS

This application is a 371 of International Application No. PCT/US2012/042603, filed 15 Jun. 2012, which claims the benefit of U.S. Provisional Application Ser. No. 61/498,099, filed 17 Jun. 2011, which is incorporated herein in its entirety.

FIELD OF THE INVENTION

The present invention relates to spirocarbamate analogs, pharmaceutical compositions containing them and their use as TRPV4 antagonists.

BACKGROUND OF THE INVENTION

TRPV4 is a member of the Transient Receptor Potential (TRP) superfamily of cation channels and is activated by heat, demonstrating spontaneous activity at physiological temperatures (Guler et al., 2002. *J Neurosci* 22: 6408-6414). Consistent with its polymodal activation property TRPV4 is also activated by hypotonicity and physical cell stress/pressure (Strotmann et al., 2000. *Nat Cell Biol* 2: 695-702), through a mechanism involving phospholipase A2 activation, arachidonic acid and epoxyeicosatrienoic acid generation (Vriens et al., 2004. *Proc Natl Acad Sci USA* 101: 396-401), In addition, amongst other mechanisms proposed, tyrosine kinase activity may also regulate TRPV4 (Wegierski et al., 2009. *J Biol Chem.* 284: 2923-33).

Heart failure results in the decreased ability of the left ventricle to pump blood into the peripheral circulation as indicated by a reduced ejection fraction and/or left ventricular dialation. This increases the left ventricular end diastolic pressure resulting in enhanced pulmonary blood pressures. This places the septal barrier, which separates the circulatory aqueous environment and the alveolar airspaces of the lung, at risk. Increased pulmonary pressure results in the flow of fluid from the pulmonary circulation into the alveolar space resulting in lung edema/congestion, as is observed in patients with congestive heart failure.

TRPV4 is expressed in the lung (Delany et al., 2001. *Physiol. Genomics* 4: 165-174) and has been shown to mediate $Ca^{2+}$ entry in isolated endothelial cells and in intact lungs (Jian et al., 2009 *Am J Respir Cell Mol Biol* 38: 386-92). Endothelial cells are responsible for forming the capillary vessels that mediate oxygen/carbon dioxide exchange and contribute to the septal barrier in the lung. Activation of TRPV4 channels results in contraction of endothelial cells in culture and cardiovascular collapse in vivo (Willette et al., 2008 *J Pharmacol Exp Ther* 325: 466-74), at least partially due to the enhanced filtration at the septal barrier evoking lung edema and hemorrage (Alvarez et al., 2006. *Circ Res* 99: 988-95). Indeed filtration at the septal barrier is increased in response to increased vascular and/or airway pressures and this response is dependent on the activity of TRPV4 channels (Jian et al., 2008 *Am J Respir Cell Mol Biol* 38: 386-92). Overall this suggests a clinical benefit of inhibiting TRPV4 function in the treatment of heart failure associated lung congestion.

Additional benefit is suggested in inhibiting TRPV4 function in pulmonary-based pathologies presenting with symptoms including lung edema/congestion, infection, inflammation, pulmonary remodeling and/or altered airway reactivity. A genetic link between TRPV4 and chronic obstructive pulmonary disorder (COPD) has recently been identified (Zhu et al., 2009. *Hum Mol Genetics,* 18: 2053-62) suggesting potential efficacy for TRPV4 modulation in treatment of COPD with or without coincident emphysema. Enhanced TRPV4 activity is also a key driver in ventilator-induced lung injury (Hamanaka et al., 2007. *Am J Physiol* 293: L923-32) and it is suggested that TRPV4 activation may underlie pathologies involved in acute respiratory distress syndrome (ARDS), pulmonary fibrosis and asthma (Liedtke & Simon, 2004. *Am J Physiol* 287: 269-71). A potential clinical benefit for TRPV4 blockers in the treatment of sinusitis, as well as allergic and non-allergic rhinitis is also supported (Bhargave et al., 2008. *Am J Rhinol* 22:7-12).

TRPV4 has been shown to be involved in Acute Lung Injury (ALI). Chemical activation of TRPV4 disrupts the alvelor septal blood barrier potentially leading to pulmonary edema (Alvarez et al, Circ Res. 2006 Oct. 27; 99(9):988-95. TRPV4 is a necessary step in a process known to cause or worsen ALI in humans (Hamanaka et al, Am J Physiol Lung Cell Mol Physiol. 2007 October; 293(4):L923-32).

Furthermore TRPV4 has in recent years been implicated in a number of other physiological/pathophysiological processes in which TRPV4 antagonists are likely to provide significant clinical benefit. These include various aspects of pain (Todaka et al., 2004. *J Biol Chem* 279: 35133-35138; Grant et al., 2007. *J Physiol* 578: 715-733; Alessandri-Haber et al., 2006. *J Neurosci* 26: 3864-3874), genetic motor neuron disorders (Auer-Grumbach et al., 2009. *Nat. Genet.* PMID: 20037588; Deng et al., 2009. *Nat Genet* PMID: 20037587; Landouré et al., 2009. *Nat Genet* PMID: 20037586), cardiovascular disease (Earley et al., 2005. *Circ Res* 97: 1270-9; Yang et al., 2006. *Am. J Physiol.* 290:L1267-L1276), and bone related disorders; including osteoarthritis (Muramatsu et al., 2007. *J. Biol. Chem.* 282: 32158-67), genetic gain-of function mutations (Krakow et al., 2009. *Am J Hum Genet* 84: 307-15; Rock et al., 2008 *Nat Genet* 40: 999-1003) and osteoclast differentiation (Masuyama et al. 2008. *Cell Metab* 8: 257-65).

SUMMARY OF THE INVENTION

In one aspect this invention provides for spirocarbamate analogs, pharmaceutically acceptable salts thereof, and pharmaceutical compositions containing them.

In a second aspect, this invention provides for the use of the compounds of Formula (I) as TRPV4 antagonists.

In another aspect, this invention provides for the use of the compounds of Formula (I) for treating and preventing conditions associated with TRPV4 imbalance.

In yet another aspect, this invention provides for the use of the compounds of Formula (I) for the treatment or prevention of atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, overactive bladder, pain, motor neuron disorders, genetic gain of function disorders, cardiovascular disease, renal dysfunction, osteoarthritis crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence.

The TRPV4 antagonist may be administered alone or in conjunction with one or more other therapeutic agents, eg. agents being selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blocker, aldosterone antagonists, iontropes, NSAIDS, nitric oxide donors, calcium channel modulators, muscarinic antagonists, steroidal anti-inflammatory drugs, bronchodilators, anti-histamines, leukotriene antagonist, HMG-CoA reductase inhibitors, dual non-selective β-adrenoceptor and α$_1$-adrenoceptor antagonists, type-5 phosphodiesterase inhibitors, and renin inhibitors.

Other aspects and advantages of the present invention are described further in the following detailed description of the preferred embodiments thereof.

DETAILED DESCRIPTION OF THE INVENTION

The present invention provides for compounds of Formula (I):

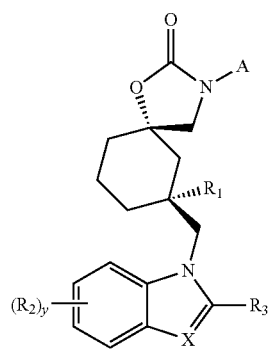

Wherein:
R$_1$ is hydrogen, C$_{1-3}$ alkyl, CH$_2$OH, CH$_2$—O—CH$_3$, CH$_2$OCH$_2$Ph, CH$_2$CN, CN, halo or C(O)OCH$_3$;
R$_2$ is independently hydrogen, CN, CF$_3$, halo, SO$_2$C$_{1-3}$alkyl, C$_{1-3}$ alkyl or C≡CH;
R$_3$ is hydrogen, C$_{1-2}$ alkyl, CF$_3$ or —OH;
R$_4$ is hydrogen, halo or C$_{1-3}$ alkyl;
X is CR$_4$ or N;
A is C$_{1-6}$ alkyl unsubstituted or substituted by 1-5 substituents chosen from:
halo, C$_{1-3}$ alkyl, C$_{3-6}$ cycloalkyl, Si(CH$_3$)$_3$, CN, C≡CH, OC$_{1-3}$alkyl, SMe, CF$_3$, OCF$_3$, SCF$_3$, C(O)OR$_c$, C(O)(NR$_d$R$_e$), tetrahydrofuryl, tetrahydropyranyl, tetrahydropyrrolyl, or oxotetrahydropyrrolyl;
wherein the tetrahydrofuryl and tetrahydropyranyl may be further substituted with one or two C$_{1-3}$ alkyl groups;
or A is C$_{5-6}$cycloalkyl substituted by one or more C$_{1-3}$alkyl groups;
or A is (CHR$_f$)$_n$—(CR$_a$R$_b$)—(CH$_2$)$_m$—R$_x$;
R$_a$ is hydrogen or C$_{1-3}$alkyl; wherein the C$_{1-3}$alkyl may be further substituted with one or more halos;
R$_b$ is C$_{1-3}$alkyl;
or R$_a$ and R$_b$ together with the carbon atom they are attached form a C$_{3-6}$ cycloalkyl group;
or one of the carbon atoms in the C$_{3-6}$cycloalkyl group formed by R$_a$ and R$_b$ may be replaced with an oxygen to form an oxetane, tetrahydrofuryl or tetrahydropyranyl group;
or one of the carbon atoms in the C$_{3-6}$cycloalkyl group formed by R$_a$ and R$_b$ may be replaced by a nitrogen to form a dihydropyrroyl group which may be further substituted with SO$_2$Me, C$_{1-4}$ alkyl, or C(O)C$_{1-4}$ alkyl;
R$_x$ is hydrogen, dihydrofuryl, C(O)OR$_c$, C(O)—(NR$_d$R$_e$), OC$_{1-4}$alkyl, CF$_3$, CN, C(O)piperidinyl, C$_{1-4}$ alkyl, or —OCF$_3$;
R$_c$ is C$_{1-4}$ alkyl;
R$_d$ is C$_{1-4}$ alkyl or C$_{3-6}$ cycloalkyl;
R$_e$ is hydrogen or C$_{1-4}$ alkyl;
R$_f$ is hydrogen or C$_{1-3}$ alkyl;
n is 1, 2, or 3;
m is 0, 1, or 2;
y is 0, 1, or 2;
or a pharmaceutically acceptable salt thereof.

"Alkyl" refers to a monovalent saturated hydrocarbon chain having the specified number of carbon member atoms. For example, C$_{1-4}$ alkyl refers to an alkyl group having from 1 to 4 carbon member atoms. Alkyl groups may be straight or branched. Representative branched alkyl groups have one, two, or three branches. Alkyl includes methyl, ethyl, propyl, (n-propyl and isopropyl), and butyl (n-butyl, isobutyl, s-butyl, and t-butyl).

"Cycloalkyl" refers to a monovalent saturated or unsaturated hydrocarbon ring having the specified number of carbon member atoms. For example, C$_{3-6}$cycloalkyl refers to a cycloalkyl group having from 3 to 6 carbon member atoms. Unsaturated cycloalkyl groups have one or more carbon-carbon double bonds within the ring. Cycloalkyl groups are not aromatic. Cycloalkyl includes cyclopropyl, cyclopropenyl, cyclobutyl, cyclobutenyl, cyclopentyl, cyclopentenyl, cyclohexyl, and cyclohexenyl.

When used herein, the terms 'halogen' and 'halo' include fluorine, chlorine, bromine and iodine, and fluoro, chloro, bromo, and iodo, respectively.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

With regard to stereoisomers, the compounds of Formula (I) may have one or more asymmetric carbon atom and may occur as racemates, racemic mixtures and as individual enantiomers or diastereomers or diastereomeric mixtures. All such isomeric forms are included within the present invention, including mixtures thereof.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of the compounds according to Formula (I) may be prepared. These pharmaceutically acceptable salts may be prepared in situ during the final isolation and purification of the compound, or by separately treating the purified compound in its free acid or free base form with a suitable base or acid, respectively.

In certain embodiments, compounds according to Formula (I) may contain an acidic functional group and are, therefore, capable of forming pharmaceutically acceptable base addition salts by treatment with a suitable base. Examples of such bases include a) hydroxides, carbonates, and bicarbonates of sodium, potassium, lithium, calcium, magnesium, aluminium, and zinc; and b) primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, succinic acid, malic acid, malonic acid, tartaric acid, citric acid, salicylic acid, benzoic acid, tannic acid, formic acid, stearic acid, lactic acid, ascorbic acid, methylsulfonic acid, p-toluenesulfonic acid, oleic acid, lauric acid, and the like.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Representative Embodiments

In one embodiment:

$R_1$ is hydrogen, $C_{1-3}$ alkyl, $CH_2OH$, $OH_2$—O—$CH_3$, $CH_2OCH_2Ph$, $CH_2CN$, CN, halo or $C(O)OCH_3$;

$R_2$ is independently hydrogen, CN, $CF_3$, halo, $SO_2C_{1-3}$ alkyl, $C_{1-3}$ alkyl or C≡CH;

$R_3$ is hydrogen, $C_{1-2}$ alkyl, $CF_3$ or —OH;

$R_4$ is hydrogen, halo or $C_{1-3}$ alkyl;

X is $CR_4$ or N;

A is $C_{1-6}$ alkyl unsubstituted or substituted by 1-5 substituents chosen from:

halo, $C_{1-3}$ alkyl, $C_{3-6}$ cycloalkyl, $Si(CH_3)_3$, CN, C≡CH, $OC_{1-3}$alkyl, SMe, $OF_3$, $OCF_3$, $SCF_3$, $C(O)OR_c$, $C(O)(N-R_dR_e)$, tetrahydrofuryl, tetrahydropyranyl, tetrahydropyrrolyl, or oxotetrahydropyrrolyl;

wherein the tetrahydrofuryl and tetrahydropyranyl may be further substituted with one or two $C_{1-3}$ alkyl groups;

or A is $C_{5-6}$cycloalkyl substituted by one or more $C_{1-3}$alkyl groups;

or A is $(CHR_f)_n$—$(CR_aR_b)$—$(CH_2)_m$—$R_x$;

$R_a$ is hydrogen or $C_{1-3}$alkyl; wherein the $C_{1-3}$alkyl may be further substituted with one or more halos;

$R_b$ is $C_{1-3}$alkyl;

or $R_a$ and $R_b$ together with the carbon atom they are attached form a $C_{3-6}$ cycloalkyl group;

or one of the carbon atoms in the $C_{3-6}$cycloalkyl group formed by $R_a$ and $R_b$ may be replaced with an oxygen to form an oxetane, tetrahydrofuryl or tetrahydropyranyl group;

or one of the carbon atoms in the $C_{3-6}$cycloalkyl group formed by $R_a$ and $R_b$ may be replaced by a nitrogen to form a dihydropyrroyl group which may be further substituted with $SO_2Me$, $C_{1-4}$ alkyl, or $C(O)C_{1-4}$ alkyl;

$R_x$ is hydrogen, dihydrofuryl, $C(O)OR_c$, $C(O)$—$(NR_dR_e)$, $OC_{1-4}$alkyl, $CF_3$, CN, $C(O)$piperidinyl, $C_{1-4}$ alkyl, or —$OCF_3$;

$R_c$ is $C_{1-4}$ alkyl;

$R_d$ is $C_{1-4}$ alkyl or $C_{3-6}$ cycloalkyl;

$R_e$ is hydrogen or $C_{1-4}$ alkyl;
$R_f$ is hydrogen or $C_{1-3}$ alkyl;
n is 1, 2, or 3;
m is 0, 1, or 2.
y is 0, 1, or 2.
In another embodiment:
$R_1$ is hydrogen or $C_{1-3}$ alkyl;
$R_2$ is independently hydrogen, CN, $CF_3$, halo or $C_{1-3}$ alkyl;
$R_3$ is hydrogen, $C_{1-2}$ alkyl, $CF_3$ or —OH;
X is N;
A is $C_{1-6}$ alkyl unsubstituted or substituted by 1-5 substituents chosen from:
halo, $C_{1-3}$alkyl, $C_{3-6}$cycloalkyl, $Si(CH_3)_3$, CN, C≡CH, $OC_{1-3}$alkyl, SMe, $CF_3$, $OCF_3$, $SCF_3$, $C(O)OR_c$, $C(O)(NR_dR_e)$, tetrahydrofuryl, tetrahydropyranyl, tetrahydropyrrolyl, or oxotetrahydropyrrolyl;
  wherein the tetrahydrofuryl and tetrahydropyranyl may be further substituted with one or two $C_{1-3}$ alkyl groups;
or A is $C_{5-6}$cycloalkyl substituted by one or more $C_{1-3}$alkyl groups;
or A is $(CHR_f)_n$—$(CR_aR_b)$—$(CH_2)_m$—$R_x$;
$R_a$ is hydrogen or $C_{1-3}$alkyl; wherein the $C_{1-3}$alkyl may be further substituted with one or more halos;
$R_b$ is $C_{1-3}$alkyl;
or $R_a$ and $R_b$ together with the carbon atom they are attached form a $C_{3-6}$ cycloalkyl group;
or one of the carbon atoms in the $C_{3-6}$cycloalkyl group formed by $R_a$ and $R_b$ may be replaced with an oxygen to form an oxetane, tetrahydrofuryl or tetrahydropyranyl group;
or one of the carbon atoms in the $C_{3-6}$cycloalkyl group formed by $R_a$ and $R_b$ may be replaced by a nitrogen to form a dihydropyrroyl group which may be further substituted with $SO_2Me$, $C_{1-4}$ alkyl, or $C(O)C_{1-4}$ alkyl;
$R_x$ is hydrogen, dihydrofuryl, $C(O)OR_c$, $C(O)$—$(NR_dR_e)$, $OC_{1-4}$alkyl, $CF_3$, CN, C(O)piperidinyl, $C_{1-4}$ alkyl, or —$OCF_3$;
$R_c$ is $C_{1-4}$ alkyl;
$R_d$ is $C_{1-4}$ alkyl or $C_{3-6}$ cycloalkyl;
$R_e$ is hydrogen or $C_{1-4}$ alkyl;
$R_f$ is hydrogen or $C_{1-3}$ alkyl;
n is 1, 2, or 3;
m is 0, 1, or 2;
y is 1 or 2.
In yet another embodiment:
$R_1$ is hydrogen or $C_{1-3}$ alkyl;
$R_2$ is independently hydrogen, CN, halo or $C_{1-3}$ alkyl;
$R_3$ is hydrogen;
X is N;
A is $C_{1-6}$ alkyl unsubstituted or substituted by 1-5 substituents chosen from:
halo, $C_{1-3}$alkyl, $C_{3-6}$cycloalkyl, $Si(CH_3)_3$, CN, C≡CH, $OC_{1-3}$alkyl, SMe, $CF_3$, $OCF_3$, $SCF_3$, $O(O)OR_c$, $C(O)(N-R_dR_e)$, tetrahydrofuryl, tetrahydropyranyl, tetrahydropyrrolyl, or oxotetrahydropyrrolyl;
  wherein the tetrahydrofuryl and tetrahydropyranyl may be further substituted with one or two $C_{1-3}$ alkyl groups;
or A is $(CHR_f)_n$—$(CR_aR_b)$—$(CH_2)_m$—$R_x$;
$R_a$ is hydrogen or $C_{1-3}$alkyl; wherein the $C_{1-3}$alkyl may be further substituted with one or more halos;
$R_b$ is $C_{1-3}$alkyl;
or $R_a$ and $R_b$ together with the carbon atom they are attached form a $C_{3-6}$ cycloalkyl group;
or one of the carbon atoms in the $C_{3-6}$cycloalkyl group formed by $R_a$ and $R_b$ may be replaced with an oxygen to form an oxetane, tetrahydrofuryl or tetrahydropyranyl group;
or one of the carbon atoms in the $C_{3-6}$cycloalkyl group formed by $R_a$ and $R_b$ may be replaced by a nitrogen to form a dihydropyrroyl group which may be further substituted with $SO_2Me$, $C_{1-4}$ alkyl, or $C(O)C_{1-4}$ alkyl;
$R_x$ is hydrogen, dihydrofuryl, $C(O)OR_c$, $C(O)$—$(NR_dR_e)$, $OC_{1-4}$alkyl, $CF_3$, CN, C(O)piperidinyl, $C_{1-4}$ alkyl, or —$OCF_3$;
$R_c$ is $C_{1-4}$ alkyl;
$R_d$ is $C_{1-4}$ alkyl or $C_{3-6}$ cycloalkyl;
$R_e$ is hydrogen or $C_{1-4}$ alkyl;
$R_f$ is hydrogen or $C_{1-3}$ alkyl;
n is 1;
m is 0 or 1; and
y is 1 or 2.

It is to be understood that the present invention covers all combinations of particular groups described hereinabove.

Specific examples of compounds of the present invention include the following:

1-(((5S,7S)-7-methyl-3-neopentyl-2-oxo-1-oxa-3-azaspiro[4.5]decan-7-yl)methyl)-1H-benzo[d]imidazole-6-carbonitrile;

1-(((5S,7S)-3-neopentyl-2-oxo-1-oxa-3-azaspiro[4.5]decan-7-yl)methyl)-1H-benzo[d]imidazole-6-carbonitrile;

1-(((5S,7S)-2-oxo-3-((trimethylsilyl)methyl)-1-oxa-3-azaspiro[4.5]decan-7-yl)methyl)-1H-benzo[d]imidazole-6-carbonitrile;

1-(((5S,7S)-3-((1-(methoxymethyl)cyclopentyl)methyl)-2-oxo-1-oxa-3-azaspiro[4.5]decan-7-yl)methyl)-1H-benzo[d]imidazole-6-carbonitrile;

1-(((5S,7S)-3-((1-ethylcyclobutyl)methyl)-2-oxo-1-oxa-3-azaspiro[4.5]decan-7-yl)methyl)-1H-benzo[d]imidazole-6-carbonitrile;

1-(((5S,7S)-3-((2-methyltetrahydrofuran-2-yl)methyl)-2-oxo-1-oxa-3-azaspiro[4.5]decan-7-yl)methyl)-1H-benzo[d]imidazole-6-carbonitrile;

1-(((5S,7S)-7-methyl-3-((2-methyltetrahydrofuran-2-yl)methyl)-2-oxo-1-oxa-3-azaspiro[4.5]decan-7-yl)methyl)-1H-benzo[d]imidazole-6-carbonitrile;

1-(((5S,7S)-3-((2-ethyltetrahydrofuran-2-yl)methyl)-2-oxo-1-oxa-3-azaspiro[4.5]decan-7-yl)methyl)-1H-benzo[d]imidazole-6-carbonitrile;

1-(((5S,7S)-7-methyl-2-oxo-3-(((S)-tetrahydrofuran-2-yl)methyl)-1-oxa-3-azaspiro[4.5]decan-7-yl)methyl)-1H-benzo[d]imidazole-6-carbonitrile;

1-(((5S,7S)-3-(2-ethoxy-2-methylpropyl)-2-oxo-1-oxa-3-azaspiro[4.5]decan-7-yl)methyl)-1H-benzo[d]imidazole-6-carbonitrile;

1-(((5S,7S)-3-((2-methyltetrahydro-2H-pyran-2-yl)methyl)-2-oxo-1-oxa-3-azaspiro[4.5]decan-7-yl)methyl)-1H-benzo[d]imidazole-6-carbonitrile;

1-(((5S,7S)-3-(3-isopropoxy-2,2-dimethylpropyl)-2-oxo-1-oxa-3-azaspiro[4.5]decan-7-yl)methyl)-1H-benzo[d]imidazole-6-carbonitrile;

1-(((5S,7S)-3-(2-cyano-2-methylpropyl)-2-oxo-1-oxa-3-azaspiro[4.5]decan-7-yl)methyl)-1H-benzo[d]imidazole-6-carbonitrile;

1-(((5S,7S)-3-(2,2-dimethyl-3-(trifluoromethoxy)propyl)-2-oxo-1-oxa-3-azaspiro[4.5]decan-7-yl)methyl)-1H-benzo[d]imidazole-6-carbonitrile;

1-(((5S,7S)-3-(2,2-dimethylcyclohexyl)-2-oxo-1-oxa-3-azaspiro[4.5]decan-7-yl)methyl)-1H-benzo[d]imidazole-6-carbonitrile;

methyl 3-(-7-((6-cyano-1H-benzo[d]imidazol-1-yl)methyl)-2-oxo-1-oxa-3-azaspiro[4.5]decan-3-yl)-2,2-dimethylpropanoate;

5-fluoro-1-(((-2-oxo-3-(2,2,3,3,3-pentafluoropropyl)-1-oxa-3-azaspiro[4.5]decan-7-yl)methyl)-1H-benzo[d]imidazole-6-carbonitrile;

7-((6-chloro-1H-benzo[d]imidazol-1-yl)methyl)-7-methyl-3-neopentyl-1-oxa-3-azaspiro[4.5]decan-2-one;

7-((5,6-dichloro-1H-benzo[d]imidazol-1-yl)methyl)-7-methyl-3-neopentyl-1-oxa-3-azaspiro[4.5]decan-2-one;

7-((5,6-difluoro-1H-benzo[d]imidazol-1-yl)methyl)-7-methyl-3-neopentyl-1-oxa-3-azaspiro[4.5]decan-2-one;

7-((5,6-dimethoxy-1H-benzo[d]imidazol-1-yl)methyl)-7-methyl-3-neopentyl-1-oxa-3-azaspiro[4.5]decan-2-one;

7-((5,6-dimethyl-1H-benzo[d]imidazol-1-yl)methyl)-7-methyl-3-neopentyl-1-oxa-3-azaspiro[4.5]decan-2-one;

3-neopentyl-7-((6-(trifluoromethyl)-1H-benzo[d]imidazol-1-yl)methyl)-1-oxa-3-azaspiro[4.5]decan-2-one;

2-ethyl-1-((-7-methyl-3-neopentyl-2-oxo-1-oxa-3-azaspiro[4.5]decan-7-yl)methyl)-1H-benzo[d]imidazole-6-carbonitrile;

5-chloro-1-((3-(2,2-dimethylpropyl)-2-oxo-1-oxa-3-azaspiro[4.5]dec-7-yl)methyl)-1H-benzimidazole-6-carbonitrile;

4-chloro-1-((-3-((4-methyltetrahydro-2H-pyran-4-yl)methyl)-2-oxo-1-oxa-3-azaspiro[4.5]decan-7-yl)methyl)-1H-benzo[d]imidazole-6-carbonitrile;

1-((-3-((4-ethyltetrahydro-2H-pyran-4-yl)methyl)-2-oxo-1-oxa-3-azaspiro[4.5]decan-7-yl)methyl)-1H-benzo[d]imidazole-6-carbonitrile;

1-((-3-(2-methylbutyl)-2-oxo-1-oxa-3-azaspiro[4.5]decan-7-yl)methyl)-1H-benzo[d]imidazole-6-carbonitrile;

5-fluoro-1-((3-neopentyl-2-oxo-1-oxa-3-azaspiro[4.5]decan-7-yl)methyl)-1H-benzo[d]imidazole-6-carbonitrile;

4-fluoro-1-((3-neopentyl-2-oxo-1-oxa-3-azaspiro[4.5]decan-7-yl)methyl)-1H-benzo[d]imidazole-6-carbonitrile;

4-chloro-1-((7-methyl-3-neopentyl-2-oxo-1-oxa-3-azaspiro[4.5]decan-7-yl)methyl)-1H-benzo[d]imidazole-6-carbonitrile;

1-((7-ethyl-3-neopentyl-2-oxo-1-oxa-3-azaspiro[4.5]decan-7-yl)methyl)-1H-benzo[d]imidazole-6-carbonitrile;

1-{[3-(2,2-dimethylpropyl)-2-oxo-1-oxa-3-azaspiro[4.5]dec-7-yl]methyl}-1H-benzimidazole-6-carbonitrile-d2;

4-chloro-1-(((5S,7S)-3-neopentyl-2-oxo-1-oxa-3-azaspiro[4.5]decan-7-yl)methyl)-1H-benzo[d]imidazole-6-carbonitrile;

4-bromo-1-((3-neopentyl-2-oxo-1-oxa-3-azaspiro[4.5]decan-7-yl)methyl)-1H-benzo[d]imidazole-6-carbonitrile;

4-methoxy-1-((3-neopentyl-2-oxo-1-oxa-3-azaspiro[4.5]decan-7-yl)methyl)-1H-benzo[d]imidazole-6-carbonitrile;

5-fluoro-1-((3-((2-methyltetrahydrofuran-2-yl)methyl)-2-oxo-1-oxa-3-azaspiro[4.5]decan-7-yl)methyl)-1H-benzo[d]imidazole-6-carbonitrile;

5-fluoro-1-((3-(3-methoxy-2,2-dimethylpropyl)-2-oxo-1-oxa-3-azaspiro[4.5]decan-7-yl)methyl)-1H-benzo[d]imidazole-6-carbonitrile;

1-(((5S,7S)-3-((2-ethyltetrahydro-2H-pyran-2-yl)methyl)-2-oxo-1-oxa-3-azaspiro[4.5]decan-7-yl)methyl)-1H-benzo[d]imidazole-6-carbonitrile;

1-(((5S,7S)-3-(3-ethoxy-2,2-dimethylpropyl)-2-oxo-1-oxa-3-azaspiro[4.5]decan-7-yl)methyl)-1H-benzo[d]imidazole-6-carbonitrile;

4-chloro-1-(((5S,7S)-3-((2-methyltetrahydrofuran-2-yl)methyl)-2-oxo-1-oxa-3-azaspiro[4.5]decan-7-yl)methyl)-1H-benzo[d]imidazole-6-carbonitrile;

7-((6-chloro-5-fluoro-1H-benzo[d]imidazol-1-yl)methyl)-3-((2-methyltetrahydrofuran-2-yl)methyl)-1-oxa-3-azaspiro[4.5]decan-2-one;

1-(((5S,7S)-2-oxo-3-((tetrahydro-2H-pyran-2-yl)methyl)-1-oxa-3-azaspiro[4.5]decan-7-yl)methyl)-1H-benzo[d]imidazole-6-carbonitrile;

5-fluoro-1-((3-((1-(methoxymethyl)cyclopropyl)methyl)-2-oxo-1-oxa-3-azaspiro[4.5]decan-7-yl)methyl)-1H-benzo[d]imidazole-6-carbonitrile;

1-(((5S,7S)-3-(3-methoxy-2,2-dimethylpropyl)-2-oxo-1-oxa-3-azaspiro[4.5]decan-7-yl)methyl)-1H-benzo[d]imidazole-6-carbonitrile;

1-(((5S,7S)-3-((4-(methoxymethyl)tetrahydro-2H-pyran-4-yl)methyl)-2-oxo-1-oxa-3-azaspiro[4.5]decan-7-yl)methyl)-1H-benzo[d]imidazole-6-carbonitrile;

(5S,7S)-3-(3-methoxy-2,2-dimethylpropyl)-7-((6-(trifluoromethyl)-1H-benzo[d]imidazol-1-yl)methyl)-1-oxa-3-azaspiro[4.5]decan-2-one;

1-(((5S,7S)-2-oxo-3-(2,2,3,3,3-pentafluoropropyl)-1-oxa-3-azaspiro[4.5]decan-7-yl)methyl)-1H-benzo[d]imidazole-6-carbonitrile;

1-(((5S,7S)-3-(2-methoxy-2-methylpropyl)-2-oxo-1-oxa-3-azaspiro[4.5]decan-7-yl)methyl)-1H-benzo[d]imidazole-6-carbonitrile;

4-chloro-1-(((5S,7S)-2-oxo-3-(((S)-tetrahydrofuran-2-yl)methyl)-1-oxa-3-azaspiro[4.5]decan-7-yl)methyl)-1H-benzo[d]imidazole-6-carbonitrile;

1-(((5S,7S)-3-((1-methylcyclobutyl)methyl)-2-oxo-1-oxa-3-azaspiro[4.5]decan-7-yl)methyl)-1H-benzo[d]imidazole-6-carbonitrile;

1-{[(5S,7S)-3-(2,2-dimethylpropyl)-2-oxo-1-oxa-3-azaspiro[4.5]dec-7-yl]methyl}-1H-benzimidazole-6-carbonitrile-d2;

1-(((5S,7S)-3-(2,2-dimethylbutyl)-2-oxo-1-oxa-3-azaspiro[4.5]decan-7-yl)methyl)-1H-benzo[d]imidazole-6-carbonitrile;

1-(((5S,7S)-3-((S)-2-methylbutyl)-2-oxo-1-oxa-3-azaspiro[4.5]decan-7-yl)methyl)-1H-benzo[d]imidazole-6-carbonitrile;

1-(((5S,7S)-3-(cyclopentylmethyl)-2-oxo-1-oxa-3-azaspiro[4.5]decan-7-yl)methyl)-1H-benzo[d]imidazole-6-carbonitrile;

4-methyl-1-((3-neopentyl-2-oxo-1-oxa-3-azaspiro[4.5]decan-7-yl)methyl)-1H-benzo[d]imidazole-6-carbonitrile;

1-{[(5S,7S)-7-methyl-3-(2-methylpropyl)-2-oxo-1-oxa-3-azaspiro[4.5]dec-7-yl]methyl}-1H-benzimidazole-6-carbonitrile;

or a pharmaceutically acceptable salt thereof.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general formula (I) and pharmaceutically acceptable derivatives and salts thereof may be accomplished as outlined below in Schemes 1-3. In the following description, the groups are as defined above for compounds of formula (I) unless otherwise indicated. Abbreviations and terms are set forth before the examples section. Starting materials are commercially available or are made from commercially available starting materials using methods known to those skilled in the art.

As shown in Scheme 1, enantiomerically-pure compounds of Formula I can be prepared in a multi-step sequence from substituted cyclohexenone ($R_1$=H, Me). S,S-hydrobenzoin can be condensed with the cyclohexenone in benzene to form the optically-pure ketal. Cyclopropanation of the ketal olefin using zinc and diiodomethane provides one cyclopropane diastereomer which can be ring-opened to the alkylbromide using hydrobromic acid in methanol. The bromide can be displaced with potassium phthalimide and deprotected with hydrazine to afford the primary amine. This amine can be alkylated via $S_{NAr}2$ displacement with a substituted ortho-fluoronitrobenzene to provide the aniline intermediate. The nitro-group can be reduced with iron in acetic acid and condensed with trimethylorthoformate to provide the resulting benzimidazole. The ketal can be removed using formic acid to provide the corresponding ketone which can then be converted to the epoxide using either trimethylsulfoxonium iodide or trimethylsulfonium iodide and base such as t-butoxide or sodium hydride to provide a mixture of cis-/trans-epoxides.

The spirocarbamate group can be installed via a two step procedure. First, the epoxide can be treated with an amine at elevated temperatures in an alcohol solvent (iPrOH, MeOH, or EtOH) or DMF to afford the aminoalcohol. The crude aminoalcohol can be dissolved in 1,4-dioxane and treated with CDI at elevated temperatures to provide the compound of Formula I.

Scheme 1

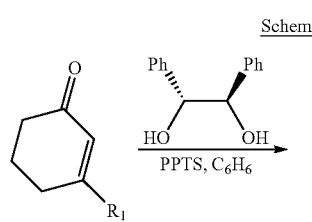

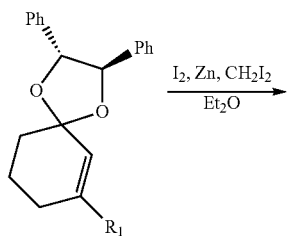

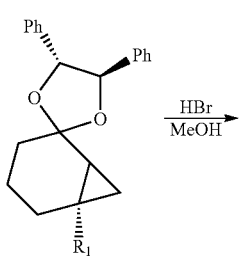

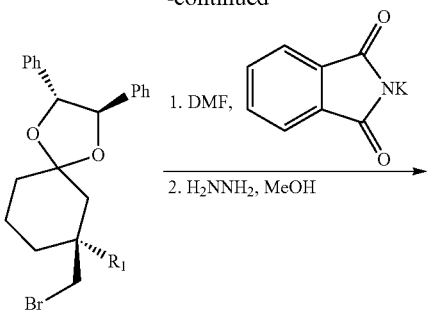

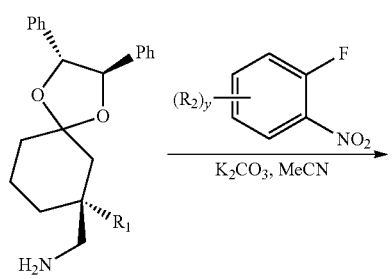

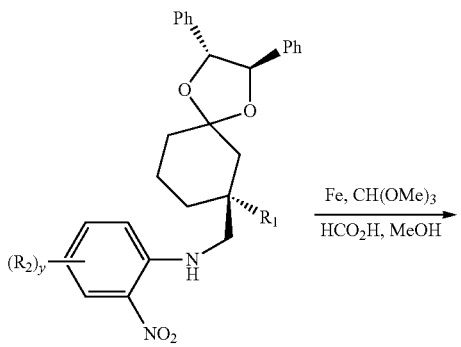

Scheme 1

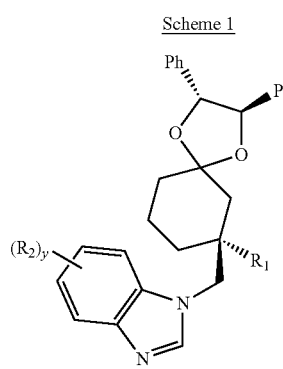

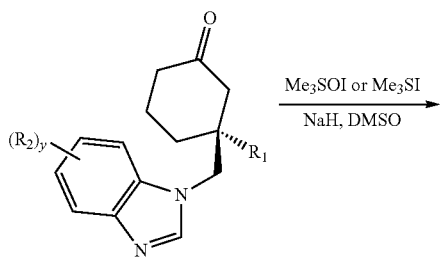

-continued

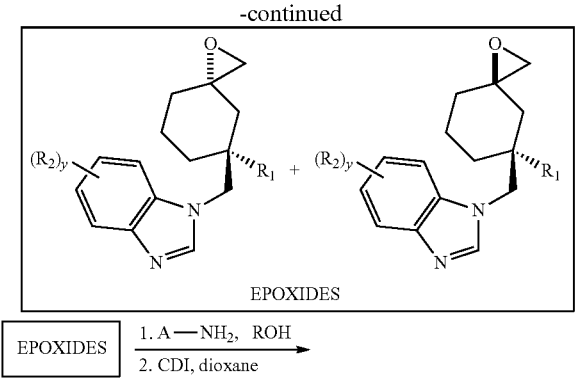

EPOXIDES $\xrightarrow{\text{1. A—NH}_2,\ \text{ROH}}{\text{2. CDI, dioxane}}$

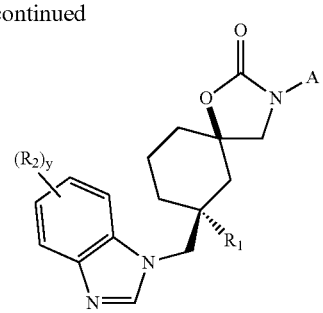

Alternatively, optically-pure compounds of Formula 1 can be prepared as shown in Scheme 2. Michael addition of nitromethane into the cyclohexenone using a chiral thiourea catalyst can provide an optically-enriched nitromethylcyclohexanone. The ketone can be protected as the acetonide with ethylene glycol, and the nitro group can be reduced to the primary amine using catalytic hydrogenation over palladium on carbon. The requisite benzimidazole moiety can then be installed from the primary amine via $S_{N_{Ar}}2$ addition of the amine into a substituted 2-fluoronitrobenzene followed by reduction of the nitrobenzene to the phenylenediamine. The diamine can be condensed with trimethyl orthoformate under acidic conditions to form the substituted benzimidazole. Acetonide group can then be removed under acidic conditions to form ketone. Ketone can be converted to the compound of Formula I via the epoxide opening strategy as described in Scheme 1.

Scheme 2

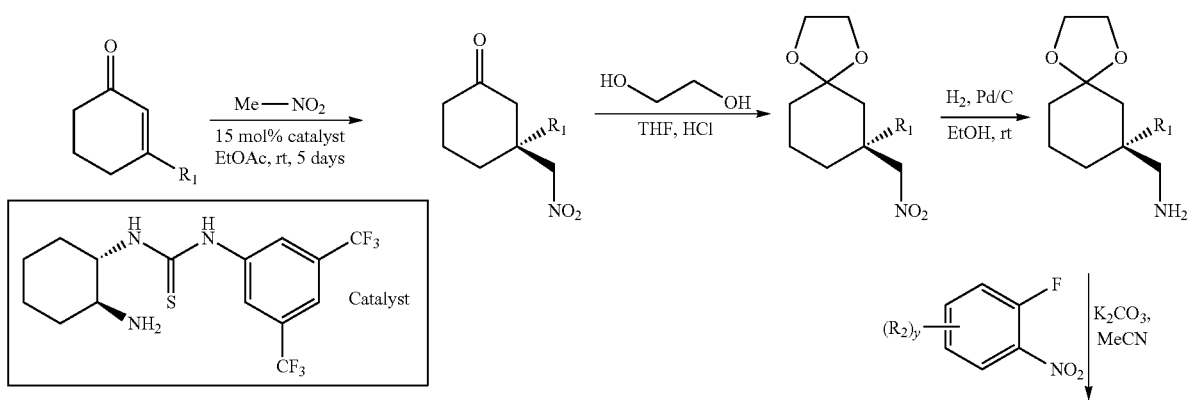

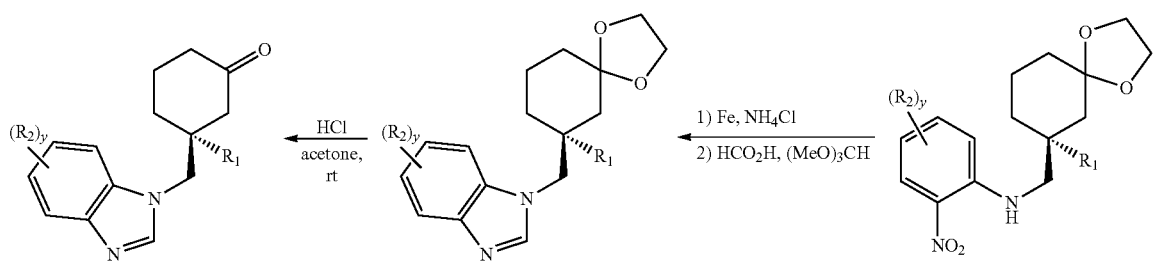

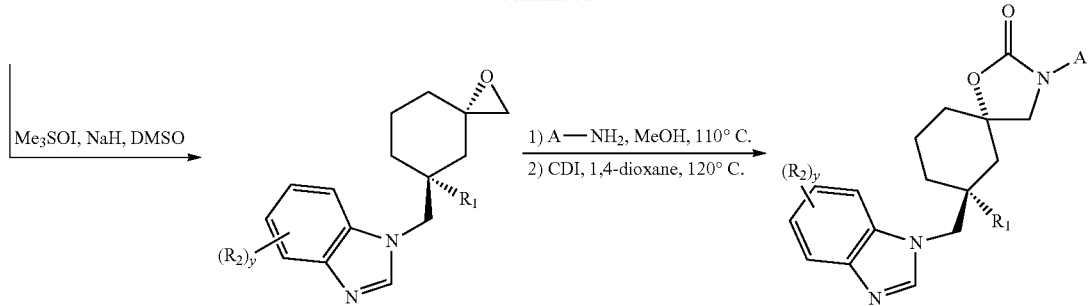

Racemic compounds of Formula I can be prepared using modified racemic versions of Schemes 1 or 2 or in a multi-step sequence starting from methyl 3-hydroxybenzoate as described in Scheme 3. Methyl 3-hydroxybenzoate can be hydrogenated over rhodium on alumina in ethanol followed by oxidation of the secondary alcohol to the ketone using ruthenium oxide and sodium perbromate. The ketone can then be converted to the epoxide and, subsequently, to the spirocyclic carbamate as described previously in Scheme 1. Incorporation of an $R_1$-substituent can be introduced by alkylating a preformed ester enolate with an electrophile such as iodomethane. Installation of the benzimidazole moiety requires an initial reduction of the methyl ester with $LiAlH_4$. The resulting alcohol can then be converted to the alkyl bromide. This installation of a leaving group allows for two alternative approaches to building the benzimidazole group. Symmetrical benzimidazoles can be used as nucleophiles in the displacement of the bromide to complete the synthesis, or 2-nitroanilines can be used as nucleophiles to displace the bromide. The resulting 2-nitroaniline intermediate can then be condensed with trimethyl orthoformate to form the benzimidazole as described previously. Alternatively, the bromide could be displaced with sodium azide. The azide can be reduced with sodium borohydride and nickel (II) chloride to provide the primary amine which can then be elaborated to the benzimidazole group as previously described in Schemes 1 and 2.

Scheme 3

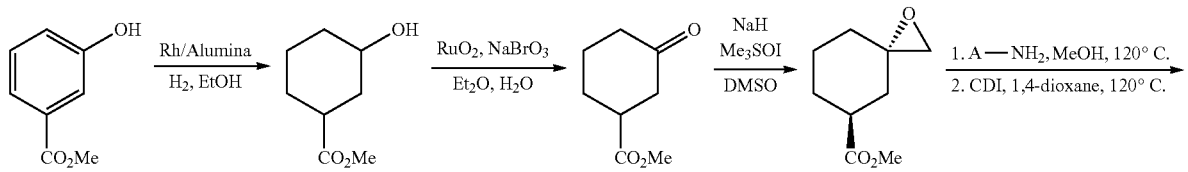

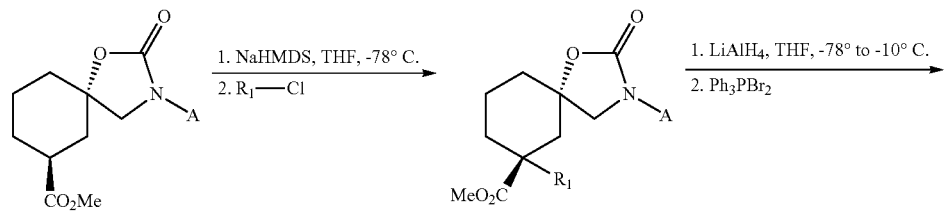

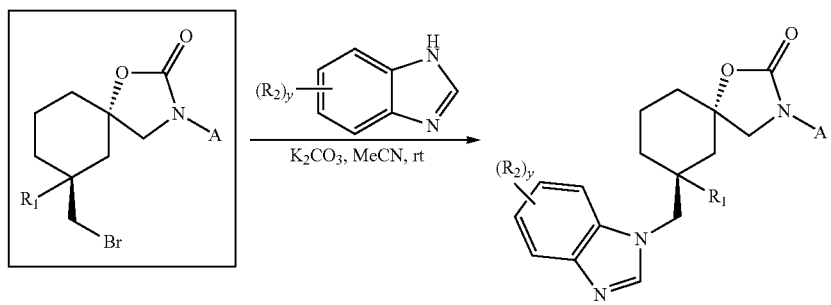

-continued

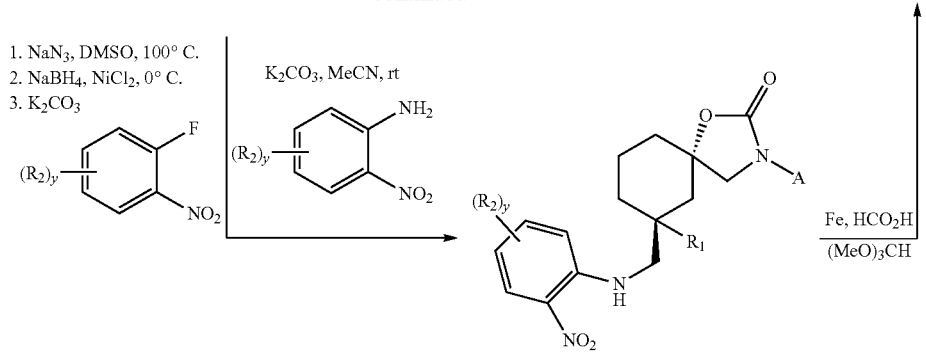

Biological Activity

As stated above, the compounds according to Formula I are TRPV4 antagonists, and are useful in the treatment or prevention of atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, pulmonary fibrosis, sinusitis/rhinitis, asthma, overactive bladder, pain, motor neuron disorders, genetic gain of function disorders, cardiovascular disease, renal dysfunction and osteoarthritis.

The biological activity of the compounds according to Formula I can be determined using any suitable assay for determining the activity of a candidate compound as a TRPV4 antagonist, as well as tissue and in vivo models.

The biological activity of the compounds of Formula (I) are demonstrated by the following tests.

Ligand-Gated Assay:

TRP channel activation/opening results in an influx of divalent and monovalent cations including calcium. The resulting changes in intracellular calcium were monitored using a calcium selective fluorescent dye Fluo4 (MDS Analytical Technologies). Dye loaded cells were initially exposed to test compound to verify a lack of agonist activity. Cells were subsequently activated by addition of an agonist and inhibition of the agonist-induced activation was recorded. Human embryonic kidney 293 cells stably expressing the macrophage scavenger receptor class II (HEK-293-MSR-II) and transduced with 1% BacMam (J. P. Condreay, S. M. Witherspoon, W. C. Clay and T. A. Kost, Proc Natl Acad Sci 96 (1999), pp. 127-132) virus expressing the human TRPV4 gene were plated at 15000 cells/well in a volume of 50 µL in a 384 well poly-D lysine coated plate. Cells were incubated for 24 hours at 37 degrees and 5% $CO_2$. Media was then aspirated using a Tecan Plate-washer and replaced with 20 µL of dye loading buffer: HBSS, 500 uM Brilliant Black (MDS Analytical Technologies), 2 uM Fluo-4. Dye loaded plates were then incubated in the dark at room temperature for 1-1.5 hours. 10 µL of test compound diluted in HBSS (HBSS with 1.5 mM Calcium Chloride, 1.5 mM Magnesium Chloride and 10 mM HEPES. pH 7.4), +0.01% Chaps was added to the plate, incubated for 10 min at room temperature in the dark and then 10 µL of agonist was added at a final concentration equal to the agonist $EC_{80}$. Calcium release was measured using the FLIPRtetra (MDS Analytical Technologies) or FLIPR384 (MDS Analytical Technologies).

All examples described herein possessed TRPV4 biological activity with $IC_{50}$s ranges from 0.1 nM-0.5 uM.

Hypotonicity Assay (BHK Cells):
Hypotonicity Assay (BHK Cells):

BHK/AC9_DMEM/F12 conditioned (Baby Hamster Kidney) cells were transduced with 2% BacMam virus expressing the human TRPV4 gene and were plated at 10K cells per well in a volume of 50 µL in 384 well poly-D-lysine coated plates. Cells were incubated for 18-24 hours at 37 degrees and 5% $CO_2$. The following day, the media was aspirated using a Tecan Plate-washer and replaced with 20 µL of dye loading buffer: HBSS buffer (HBSS with 1.5 mM Calcium Chloride, 1.5 mM Magnesium Chloride and 10 mM HEPES. pH 7.4), 2.5 mM Probenecid, 500 µM Brilliant Black, 2 µM Fluo-4. The dye loaded cells were incubated for 1-1.5 hours at room temperature in the dark. 10 µL of test compound diluted in $HBSS/H_2O$ (~1:2.3)+0.01% Chaps was added to the plate, incubated for 10 min at room temperature in the dark, and then 10 uL of hypotonic buffer ($H_2O$+1.5 mM $CaCl_2$+~68 mM NaCl; 140 mOsm stock/260 mOsm FAC) was used to test the inhibition of the hypotonicity-induced activation. Reaction was measured on a heated stage (37 degrees) using the FLIPRtetra. ($pIC_{50}$ range 6.3-10.0)

Fluorescent Imaging Plate Reader (FLIPR) Assay

The FLIPR assay detects changes in intracellular $Ca^{2+}$ ($Ca^{2+}_i$) ion concentrations following stimulation of various biochemical pathways that can increase $Ca^{2+}_i$ levels. An increase in $Ca^{2+}_i$ was quantified with the use of dye that becomes activated and subsequently contained within cells, then selectively fluoresces when bound to $Ca^{2+}$. A molecule known to selectively activate human TRPV4 channels, (N-((1S)-1-{[4-((2S)-2-{[(2,4-dichlorophenyl)sulfonyl]amino}-3-hydroxypropanoyl)-1-piperazinyl]carbonyl}-3-methylbutyl)-1-benzothiophene-2-carboxamide; GSK1016790A); (Thorneloe, et al., J Pharmacol Exp Ther, 326: 432, August 2008), was applied to cells to trigger TRPV4 channel-dependent influx of $Ca^{2+}$ from the extracellular solution and prevention of the dye accumulation by a molecule was considered as evidence of blockade of native TRPV4 channel activity.

Alveolar macrophages are critical mediators of Acute Lung Injury in multiple animal models and mouse alveolar macrophages display functional changes that are triggered by a prototypical TRPV4 activator (the phorbol ester 4αPDD) and absent in cells where the Trpv4 gene product has been deleted (Hamanaka, et al., 2010). In light of these findings, we obtained primary alveolar macrophages from broncho-alveolar lavage (BAL) solutions obtained from healthy human volunteers. BAL fluid was centrifuged and the resulting cell pellet was washed phosphate-buffered saline (PBS) and resuspended. This solution was then centrifuged and the cell pellet was resuspended in cell culture medium (DMEM with 10% fetal bovine serum supplemented with 1000 units/L penicillin/1000 µg/L streptomycin). In humans and laboratory animals, BAL cells consist largely of alveolar macrophages, although cell populations may be further enriched for alveolar macrophages by adherence to plastic materials such as wells of 96-well plates. We utilized this established principle to enrich for alveolar macrophages by plating human alveolar macrophages at densities of ~40,000 cells/well in 96-well plates, followed by washes with fresh medium after 30-60 minutes of incubation at 37° C. in a 5% $CO_2$ atmosphere and again after 18-24 h of incubation in the same conditions.

After 18 to 24 hours, media was aspirated and replaced with 100 ml load media containing EMEM with Earl's salts and L-Glutamine, 0.1% BSA (Millipore), 4 mM Fluo-4-acetoxymethyl ester fluorescent indicator dye (Fluo-4 AM, Invitrogen) and 2.5 mM probenecid. Cells were then incubated for 1 hour at 37° C. After aspirating off the dye containing media, the cells were washed 3 times with 100 mL of KRH assay buffer (120 mM NaCl, 4.6 mM KCl, 1.03 mM $KH_2PO_4$, 25 mM $NaHCO_3$, 1.0 mM $CaCl_2$, 1.1 mM $MgCl_2$, 11 mM Glucose, 20 mM HEPES, 0.1% gelatin, 2.5 mM probenecid, pH 7.4). To evaluate antagonist effects of a compound, 100 mL KRH assay buffer, containing 0.1% DMSO, 10 & 100 nM of the compound or the precedented, non-selective TRPV channel blocker Ruthenium Red (10 µM), was added to the wells and the plate warmed to 37° C. for 15 minutes before being placed in FLIPR (Molecular Devices, Sunnyvale, Calif.) where dye loaded cells are exposed to excitation light (488 nm) from a 6 watt Argon Laser. After the basal emission fluorescence measurements, the cellular response to a concentration range of TRPV4 opener, GSK1016790A (0.3-1000 nM), was monitored in FLIPR for 10 minutes at 516 nm emission fluorescence intensity. A secondary response to ionomycin (1 µM) was then recorded for all wells for 5 minutes. Peak emission from each well after addition of each stimulant is then exported to an excel spreadsheet. Results from each well were converted to % ionomycin. This data was then transferred to GraphPad Prism version 4.03 for plotting of response to each treatment condition. Shift of receptor EC50 response to GSK1016790A in presence of compound compared to vehicle was utilized to determine compound potency and type of receptor interaction using classical Schild analysis.

Patch Clamp Experiments

Patch clamp experiments can measure cationic currents moving through TRPV4-containing channels in the plasma membrane of cells including human alveolar macrophages. In traditional whole-cell patch-clamp recordings, cells are cultured in a manner such that multiple cells do not directly contact one another to confound the capacitance value of an individual cell's plasma membrane. The membrane of a single cell is contacted by a glass electrode and the membrane is ruptured, resulting in whole-cell configuration, which allows the investigator to fill the cytoplasm of the cell with the contents of the electrode (intracellular) solution and also to evoke membrane currents by manipulating the voltage of the cell membrane. Ionic gradients are established based on the differences in the ions contained within the intracellular solution and those contained within the extracellular solution, which is delivered over the cells via a gravity-fed perfusion system. When applicable, agonists that provoke TRPV4-dependent currents and/or blockers of TRPV4-containing channels can be added to the extracellular solution.

Human primary alveolar macrophages were plated on glass coverslips in growth medium overnight at a low density in order to avoid direct contact between cells. Patch clamp recordings were performed in whole-cell mode. Cells were perfused with standard extracellular solution consisting of (in mM): mM): 140 NaCl, 5 NaCl, 2 $MgCl_2.6H_2O$, 5 $CsCl_2$, 10 HEPES, and 10 D-Glucose, bubbled with 95% $O_2$/5% $CO_2$ gas and adjusted to pH 7.4 with NaOH. The internal solution used to fill the cell via the glass electrode consisted of (in mM: mM) 140 CsCl, 4 $MgCl_2$, 10 N-[2-hydroxyethyl]piperazine-N'-[2-ethanesulfonic acid] (HEPES), and 5 ethylene glycol bis(β-aminoethyl ether)-N,N,N',N'-tetraacetic acid (EGTA), adjusted to pH 7.2 with CsOH. Voltage ramps from −80 to +80 mV over durations of 500 msec were applied and sampled at 500 Hz, and the recordings were filtered at 10 kHz. Data were analyzed using clampfit software and analyzed in Excel spreadsheets or Graphpad Prism 4.

Hypotonic solutions are often used as surrogates for application of mechanical force on cells, as hypotonic extracellular solutions cause cell membranes to stretch. Since hypotonic solutions have been demonstrated to activate TRPV4 and produce TRPV4-dependent currents in cells expressing TRPV4-containing ion channels (Alessandri-Haber, et al., Neuron, 39: 497, July 2003), extracellular solution was replaced with a hypotonic extracellular solution consisting of (in mM): 74 NaCl, 5 KCl, 1.2 $KH_2PO_4$, 1.3 $MgCl_2$, 2.4 $CaCl_2$, and 26 $NaHCO_3$, adjusted to pH 7.4 with NaOH in order to evoke TRPV4-dependent currents. Once the hypotonic solution had evoked changes in currents (quantified at −80 and +80 mV), compound was added to the hypotonic extracellular solution and the reduction in currents was quantified.

Methods of Use

The compounds of the invention are TRPV4 antagonists, and are useful in the treatment or prevention of atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, overactive bladder, pain, motor neuron disorders, genetic gain of function disorders, cardiovascular disease, renal dysfunction, osteoarthritis crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence. Accordingly, in another aspect the invention is directed to methods of treating such conditions.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per dose. Preferred dosages are 10-500 mg BID per person.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

The compounds may be administered alone or in conjunction with one or more other therapeutic agents, said agents being selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blocker, aldosterone antagonists, iontropes, NSAIDS, nitric oxide donors, calcium channel modulators, muscarinic antagonists, steroidal anti-inflammatory drugs, bronchodilators, anti-histamines, leukotriene antagonists, HMG-CoA reductase inhibitors, dual non-selective β-adrenoceptor and $\alpha_1$-adrenoceptor antagonists, type-5 phosphodiesterase inhibitors, and renin inhibitors.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Flash column chromatography was performed on silica gel.

LCMS data was generated on an Agilent 1100 Series LCMS system using a Sunfire C18, 5 μm column (3×50 mm). Column temperature was kept at a constant 40° C. with a 1.2 mL/min solvent flowrate. A gradient elution of 10-100% MeOH/water/0.1% TFA over 2.5 min was used for each sample. Dual wavelength detection (220 nm/254 nm) was used for sample analysis.

The naming program used is ACD Name Pro 6.02 or Chem Draw Ultra 12.0.

The following abbreviations and terms had the indicated meanings throughout:

| Abbreviation | Meaning |
| --- | --- |
| AcOH | acetic acid |
| aq | aqueous |
| $Boc_2O$ | di-tert-butyl dicarbonate |
| Brine | saturated aqueous NaCl |
| CAN | ceric ammonium nitrate |
| CDI | Carbonyl diimidazole |
| $CCl_4$ | carbon tetrachloride |
| $CH_2Cl_2$ or DCM | methylene chloride |
| $CH_3CN$ or MeCN | acetonitrile |
| $CH_3I$ or MeI | methyl iodide |
| $CH_3SNa$ | sodium methyl mercaptide |
| $(COCl)_2$ | oxalyl chloride |
| $Cs_2CO_3$ | cesium carbonate |
| CuI | copper(I) iodide |
| d | day |
| DCE | dichloroethane |
| DMAP | 4-dimethylaminopyridine |
| DMF | N,N-dimethylformamide |
| DMSO | dimethylsulfoxide |
| DIEA | N,N-diisopropylethylamine |
| Equiv | equivalents |
| Et | ethyl |
| EtI | ethyl iodide |
| $Et_3N$ | triethylamine |
| EtOH | ethanol |
| $Et_2O$ | diethyl ether |
| EtOAc | ethyl acetate |
| h, hr | hour |
| HBr | hydrobromic acid |
| HCl | hydrochloric acid |
| HOBt | 1-hydroxybenzotriazole |
| $H_2SO_4$ | sulfuric acid |
| i-PrI | 2-iodopropane |
| i-PrOH | isopropanol |
| i-$Pr_2$NEt | N',N'-diisopropylethylamine |

| Abbreviation | Meaning |
|---|---|
| $K_2CO_3$ | potassium carbonate |
| KOH | potassium hydroxide |
| KOtBu | Potassium tert-butoxide |
| LCMS | liquid chromatography-mass spectroscopy |
| m-CPBA | meta-chloroperoxybenzoic acid |
| Me | methyl |
| MeI | methyl iodide |
| MeOH or $CH_3OH$ | methanol |
| $MgSO_4$ | magnesium sulfate |
| min | minute |
| mL | milliliters |
| MS | mass spectrum |
| μw | microwave |
| $NaBH_4$ | sodium borohydride |
| $NaBH(OAc)_3$ | sodium triacetoxyborohydride |
| n-BuLi | n-butyllithium |
| $Na_2CO_3$ | sodium carbonate |
| NaH | sodium hydride |
| $NaHCO_3$ | sodium bicarbonate |
| NaOH | sodium hydroxide |
| $Na_2SO_4$ | sodium sulfate |
| $NH_2OH·HCl$ | hydroxylamine hydrochloride |
| $NH_4Cl$ | ammonium chloride |
| $NH_4OH$ | ammonium hydroxide |
| NiCl | nickel chloride |
| nm | nanometers |
| NMP | N-methylpyrrolidone |
| Pd/C | palladium on carbon |
| Ph | phenyl |
| PPTS | Pyridinium p-toluenesulfonate |
| $Rh/Al_2O_3$ | rhodium on aluminum oxide |
| rt | room temperature |
| satd | saturated |
| SCX | strong cation exchange |
| SPE | solid phase extraction |
| SFC | Supercritical fluid chromatography |
| TFA | trifluoroacetic acid |
| THF | tetrahydrofuran |
| $t_R$ | retention time |

Intermediate 1

1-{[(1S)-1-methyl-3-oxocyclohexaneyl]methyl}-1H-benzimidazole-6-carbonitrile

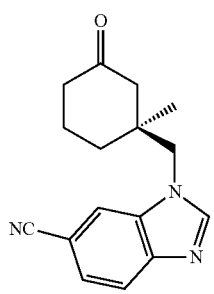 [SMILES: C[C@]1(Cn2cnc3ccc(C#N)cc32)CCCC(=O)C1]

(2R,3R)-7-Methyl-2,3-diphenyl-1,4-dioxaspiro[4.5]dec-6-ene (1R,2R)-1,2-diphenyl-1,2-ethanediol (150 g, 699 mmol) and 3-methyl-2-cyclohexen-1-one (77 g, 699 mmol) were suspended in benzene (1398 mL) and treated with PPTS (4.39 g, 17.48 mmol). The flask was fitted with a Dean-Stark trap filled with benzene and a condenser. The reaction was heated to 115° C. for 3 days, and then the reaction was cooled to ambient temperature and diluted with ether. The mixture was washed with saturated aq $NaHCO_3$. The organic layer was dried over $MgSO_4$, filtered and concentrated to give a red/orange liquid (214 g, 100% yield). The liquid was used without further purification.

(1S,4'R,5'R,6R)-6-Methyl-4',5'-diphenylspiro[bicyclo[4.1.0]heptane-2,2'-[1,3]-dioxolane]

Zinc/copper couple was freshly prepared by quickly washing zinc dust with 1N HCl (4×100 mL) in a flask and decanting the supernatant. The solid was then washed in the same manner with distilled water (4×120 mL), 2 mol % $CuSO_4$ solution (2×200 mL), distilled water (4×120 mL), EtOH (4×120 mL) and $Et_2O$ (5×100 mL). The $Et_2O$ washes were poured onto a funnel and dried by vacuum filtration. The resulting solid was added to a 3 L flask and dried under vacuum at 50° C. for 30 min, then cooled to RT. The flask was fitted with an addition funnel and reflux condenser, then purged with nitrogen and kept under $N_2$ throughout the reaction. Next, 650 mL of $Et_2O$ was added followed by $I_2$ (0.886 g, 3.49 mmol), and the solution was stirred and heated to reflux. Once at reflux, heating was stopped and diiodomethane (150 mL, 1865 mmol) was slowly added making sure to not allow the reaction to reflux out of control. (2R,3R)-7-methyl-2,3-diphenyl-1,4-dioxaspiro[4.5]dec-6-ene (214 g, 698 mmol in 600 mL $Et_2O$) was then added to the reaction mixture, followed by an additional 0.5 eq of diiodomethane. The reaction was heated to reflux, and the reaction was monitored by LCMS. After 1.5 h the reaction was cooled to RT and quenched with saturated aq $Na_2CO_3$ (170 g in 800 mL water). The mixture was stirred for 30 min, then filtered through celite. The inorganics were washed with $Et_2O$ (2 L), then the combined organics were washed with saturated $NH_4Cl$ (1 L), saturated $NaHCO_3$ (1 L), brine (1 L), then dried over $MgSO_4$, filtered and concentrated to afford the crude product. Methanol (350 mL) was added to the residue and the suspension was heated to 50° C. The resultant solution was cooled with stirring to RT to crystallize the product. The slurry was stirred overnight at RT, then cooled to 0° C., and stirred for an additional 1 h. The slurry was filtered, washed with a minimal amount of MeOH and dried under reduced pressure to afford the desired product as a white solid (137 g, 61% yield).

(2R,3R,7S)-7-(Bromomethyl)-7-methyl-2,3-diphenyl-1,4-dioxasbiro[4.5]decane (1S,4'R,5'R,6R)-6-Methyl-4',5'-diphenylspiro[bicyclo[4.1.0]heptane-2,2'-[1,3]dioxolane] (137 g, 428 mmol) was dissolved in MeOH (1993 mL) and treated with hydrobromic acid in water (145 mL, 1283 mmol). The reaction was stirred at RT for 24 h, then concentrated to give a yellow residue. To the residue was added hexane (1 L) and the solution was stirred for 5 min. The hexane was decanted off leaving a yellow liquid behind. This process of adding hexane followed by decanting was repeated. The final volume of yellow liquid was 100 mL. The combined hexane washes were concentrated under reduced pressure to afford the desired product as a light yellow oil (172 g, 100% yield). The oil was used without further purification.

{[(2R,3R,7S)-7-Methyl-2,3-diphenyl-1,4-dioxasbiro[4.5]dec-7-yl]methyl}amine

To a 1 L flask was added (2R,3R,7S)-7-(bromomethyl)-7-methyl-2,3-diphenyl-1,4-dioxaspiro[4.5]decane (172 g, 428 mmol), potassium phthalimide (399 g, 2140 mmol), and NMP (900 mL). The mixture was allowed to stir at 130° C. for 24 h, then 120° C. for 4 days. Next, the mixture was cooled to RT and filtered. The solids were washed with Et$_2$O. The organics were added to a separatory funnel and diluted with Et$_2$O and water. The ether was separated and washed with saturated aq NaHCO$_3$, brine and then dried over Na$_2$SO$_4$, filtered and concentrated under reduced pressure to afford the desired intermediate as a thick orange/yellow oil which was used directly in the next reaction. To the oil was added methanol (2.25 L) followed by hydrazine (40.3 mL, 1284 mmol). The solution was heated to reflux and the reaction was monitored by LCMS. Following completion (2 h), the solution was then cooled to RT and filtered. The filter cake was washed with MeOH, and the filtrate was then concentrated under reduced pressure. To the residue was added THF and the mixture was stirred. The resulting white solids were collected by filtration and the filtrate concentrated. A third crop was obtained by dissolving the residue in hexane. The solution was stirred with heating, then cooled to RT and filtered. Concentration of the hexane afforded the desired product as a light yellow oil (134.75 g, 93% yield). MS (m/z) 338.2 (M+H$^+$).

3-({[(2R,3R,7S)-7-Methyl-2,3-diphenyl-1,4-dioxaspiro[4.5]dec-7-yl]methyl}amino)-4-nitrobenzonitrile A solution of acetonitrile (2049 mL) in a 3 L flask was heated to 40° C. Next, potassium carbonate (198 g, 1434 mmol), 1-[(2R,3R,7S)-7-methyl-2,3-diphenyl-1,4-dioxaspiro[4.5]dec-7-yl]methanamine (242 g, 717 mmol) and 3-fluoro-4-nitrobenzonitrile (119 g, 717 mmol) were added slowly. The mixture was allowed to stir at 40° C. for 2 h, and then cooled to RT. Stirring was continued at RT overnight. The next day, the slurry was filtered and the solids were washed with acetonitrile (500 mL). The filtrate was concentrated to afford the crude product (while keeping the temperature ~60° C. during concentration). To the thick dark residue was added MeOH. The solution was heated to 60° C. on the rotovap and concentrated to a minimal volume. To the residue was added ~500 mL of MeOH slowly with heating to avoid rapid crystallization, and the solution was heated to reflux. Once at reflux, an additional 250 mL MeOH was slowly added. The resulting slurry was allowed to stir at reflux for about 60 min, then heating was stopped and the slurry was allowed to cool to RT and stirring was continued for 3 days. The slurry was cooled to ~10° C. with an ice/water bath. Stirring was continued for ~2 h, and then the slurry was filtered and washed with cold MeOH (100 mL). The solids were dried under reduced pressure to give the desired product as a bright orange solid (245 g, 70.7% yield).

1-{[(2R,3R,7S)-7-Methyl-2,3-diphenyl-1,4-dioxasbiro[4.5]dec-7-yl]methyl}-1H-benzimidazole-6-carbonitrile A 5 L three neck flask was fitted with a mechanical stirrer and condenser. To the flask was added 3-({[(2R,3R,7S)-7-methyl-2,3-diphenyl-1,4-dioxaspiro[4.5]dec-7-yl]methyl}amino)-4-nitrobenzonitrile (245.5 g, 508 mmol), MeOH (891 mL) and EtOAc (891 mL). Next, trimethyl orthoformate (561 mL, 5077 mmol) and formic acid (195 mL, 5077 mmol) were added. The resulting mixture was heated at 64° C. Next, (2-3 eq) of formic acid, trimethylorthoformate and iron were added every 15 min until the reaction was finished (3.5 h). Next, the mixture was filtered to remove excess iron, and the iron was washed with EtOAc. The filtrate was concentrated and the resulting thick purple residue (residue contained formic acid) was used without further purification (235 g, 100% yield).

1-{[(1S)-1-Methyl-3-oxocyclohexaneyl]methyl}-1H-benzimidazole-6-carbonitrile

A mixture of 1-{[(2R,3R,7S)-7-methyl-2,3-diphenyl-1,4-dioxaspiro[4.5]dec-7-yl]methyl}-1H-benzimidazole-6-carbonitrile (235 g, 508 mmol) in formic acid (1948 mL) was heated to 70° C. for 18 h, then the solution was concentrated under reduced pressure, and diluted with sat. NaHCO$_3$ until it was basic. The resulting mixture was extracted with DCM (3×), and the combined extracts were washed with brine and then concentrated under reduced pressure. To the residue was added EtOAc (1 L) and then it was concentrated at 60° C. to a volume of approximately 750 mL. The slurry was then allowed to cool. Once solids started to form, the slurry was slowly diluted with 500 mL of hexanes and the temperature was raised to about 60° C. An additional 500 mL of hexanes was slowly added and the temperature was raised to reflux (about 68° C.). Once at reflux, heating was stopped, and the solution was allowed to cool to RT and stir for 5 days. Then the slurry was filtered, the solids were washed with hexanes and dried under reduced pressure to give 105.5 g of product (78% yield). The filtrate was concentrated and loaded onto silica gel and purified on a 220 g column (like a plug of silica) using vacuum to pull solvent through the column, and eluted with 500 mL of DCM, then 1 L of 50% EtOAc/DCM, then 1 L of 100% DCM, then 1 L each of 2.5%, 5%, 7.5%, and 10% MeOH/DCM. Fractions were collected in 1 L portions. Fractions containing product were concentrated to afford an additional 20.4 g (15% yield) of product. MS (m/z) 268.1 (M+H$^+$).

Intermediate 2

1-{[(1S)-3-Oxocyclohexaneyl]methyl}-1H-benzimidazole-6-carbonitrile

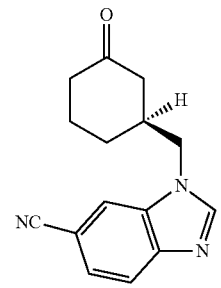 [SMILES: N#Cc1ccc2ncn(C[C@H]3CCCC(=O)C3)c2c1]

(2R,3R)-2,3-Diphenyl-1,4-dioxaspiro[4.5]dec-6-ene

To a 2 L flask was added (1R,2R)-1,2-diphenyl-1,2-ethanediol (200 g, 924 mmol), 2-cyclohexen-1-one (101 g, 1017 mmol), benzene (1232 mL) and PPTS (11.61 g, 46.2 mmol). The flask was fitted with a condenser and a dean-stark trap filled with benzene. The reaction was heated to 115° C. for 18 h (meanwhile trap contained 16.8 mL water indicating reaction completion). The reaction was cooled to RT and diluted with ether. The mixture was washed with saturated aq NaHCO$_3$. The organic layer was dried over MgSO$_4$, filtered and concentrated to give an orange liquid. This was passed over a silica gel plug eluting with 100% hexane (500 mL), then 5% EtOAc/Hexane (2 L), then 10% EtOAc/Hexane (500 mL), then 25% EtOAc/Hexane (500 mL). The product eluted in the first ~2.5 L of solvent. Removal of solvent afforded a light yellow oil. To this residue was added ~275 mL of hexane and the solution was let stand and crystals started to rapidly form. After about 1 h at RT, the solution was cooled in the freezer overnight. The next day, the hexane was decanted off, the solids washed with cold hexane. The solids were dried under reduced pressure at 75° C., and 223.75 g of (2R,3R)-2,3-diphenyl-1,4-dioxaspiro[4.5]dec-6-ene was obtained. The hexane solution was concentrated and purified by silica gel (ISCO, 330 g column, 100 mL/min, 0-10% EtOAc/Hexane over 40 min). Concentration of the pure fractions afforded (2R,3R)-2,3-diphenyl-1,4-dioxaspiro[4.5]dec-6-ene as an oil that solidified on sitting (30.47 g).

(1S,4'R,5'R,6R)-4',5'-Diphenylspiro[bicyclo[4.1.0]heptane-2,2'-[1,3]-dioxolane]

The zinc/copper couple was freshly prepared by quickly washing zinc dust with 1N HCl (4×100 mL), then washing with distilled water (4×120 mL), 2 mol % $CuSO_4$ solution (2×200 mL), water (4×120 mL), EtOH (4×120 mL) and $Et_2O$ (5×100 mL). The washings were done in a flask with decanting of the liquid. The $Et_2O$ washes were poured onto a funnel and dried by vacuum filtration. The resulting solid was added to a 2 L flask and dried under vacuum at 115° C. for 30 min, then cooled to RT. The flask was fitted with an addition funnel and reflux condenser, then purged with nitrogen and kept under $N_2$ throughout the reaction. Next, 400 mL of $Et_2O$ was added followed by $I_2$ (0.551 g, 2.172 mmol), and the solution was stirred and heated to reflux. Once at reflux, heating was stopped and diiodomethane (87 mL, 1086 mmol) was slowly added making sure to not allow the reaction to reflux out of control. (2R,3R)-2,3-diphenyl-1,4-dioxaspiro[4.5]dec-6-ene (127 g, 434 mmol) was then added in 350 mL ether, followed by an additional 0.5 eq of diiodomethane. The reaction was heated to reflux and the reaction monitored by LCMS. After 1.5 h the reaction was cooled to RT and quenched with saturated aq $Na_2CO_3$ (230 g in 900 mL water). The mixture was stirred for 30 min, then filtered through celite. The inorganics were washed with $Et_2O$ (2 L), then the combined organics were washed with saturated aq $NH_4Cl$ (1 L), saturated aq $NaHCO_3$ (1 L), brine (1 L). The organic layers were dried over $MgSO_4$, filtered and concentrated to afford the crude product (176.45 g). To the residue was added $Et_2O$ (250 mL) and the suspension was heated to reflux, then allowed to cool to RT to crystallize the product. The suspension was put in the freezer for 3 days, then the ether decanted off. Drying of the solids gave (1S,4'R,5'R,6R)-4',5'-diphenylspiro[bicyclo[4.1.0]heptane-2,2'-[1,3]dioxolane] (112.5 g, 85% yield). The material was used as an intermediate without further purification.

(2R,3R,7S)-7-(Bromomethyl)-2,3-diphenyl-1,4-dioxaspiro[4.5]decane

The (4'R,5'R,6R)-4',5'-diphenylspiro[bicyclo[4.1.0]heptane-2,2'-[1,3]dioxolane] (112 g, 366 mmol) was dissolved in MeOH (1704 mL) and treated with hydrobromic acid in water (124 mL, 1097 mmol). The reaction was stirred at RT for 18 h and then concentrated. The residue was dissolved in hexane, then the hexane was decanted off leaving a yellow oil behind (HBr residue). The hexane was concentrated under reduced pressure to afford the (2R,3R,7S)-7-(bromomethyl)-2,3-diphenyl-1,4-dioxaspiro[4.5]decane as a light yellow oil (138.88 g, 98% yield). The oil was used without further purification.

1-[(2R,3R,7S)-2,3-Diphenyl-1,4-dioxaspiro[4.5]dec-7-yl]methanamine

To a 2 L flask was added (2R,3R,7S)-7-(bromomethyl)-2,3-diphenyl-1,4-dioxaspiro[4.5]decane (146 g, 377 mmol), phthalimide (140 g, 754 mmol), and DMF (750 mL). The mixture was allowed to stir at 80° C. for 24 h, then cooled to RT. The mixture was added to a separatory funnel and diluted with $Et_2O$ and water. The ether was separated and the water extracted again with $Et_2O$. The combined ether extracts were washed with saturated aq $NaHCO_3$ and brine. The $Et_2O$ layers were dried over $Na_2SO_4$, filtered and concentrated under reduce pressure to afford the desired intermediate as a pale yellow glassy solid. To the residue was added MeOH (1875 mL) followed by hydrazine (35.5 mL, 1131 mmol). The solution was heated to reflux and the reaction monitored by LCMS. After 2 h, the solution was cooled to RT, filtered and washed with MeOH. The filtrate was concentrated under reduced pressure. To the residue was added THF and the mixture was stirred. The resulting solid was filtered off and the THF concentrated. The residue was dissolved in hexane, stirred with heating, then cooled to RT and filtered. Concentration of the hexane afforded the 1-[(2R,3R,7S)-2,3-diphenyl-1,4-dioxaspiro[4.5]dec-7-yl]methanamine as a light yellow oil (116.28 g, 95% yield). The oil was used without further purification.

3-({[(2R,3R,7S)-2,3-Diphenyl-1,4-dioxaspiro[4.5]dec-7-yl]methyl}amino)-4-nitrobenzonitrile A mixture of 3-fluoro-4-nitrobenzonitrile (55.5 g, 334 mmol), 1-[(2R,3R,7S)-2,3-diphenyl-1,4dioxaspiro[4.5]dec-7-yl]methanamine (103 g, 318 mmol) and potassium carbonate (88 g, 637 mmol) in acetonitrile (2654 mL) was stirred at RT for 5 days (~200 mL DCM was added to help with solubility). The resulting solution was filtered and the solids washed with MeCN. The resulting solution was concentrated to give the crude product that was dissolved in MeOH (500 mL) and allowed to crystallize with stirring. The slurry was allowed to stir at RT overnight, filtered and the solids dried under reduced pressure to give 3-({[(2R,3R,7S)-2,3-diphenyl-1,4-dioxaspiro[4.5]dec-7-yl]methyl}amino)-4-nitrobenzonitrile (131.41 g, 88% yield). The product was used without further purification.

1-{[(2R,3R,7S)-2,3-Diphenyl-1,4-dioxaspiro[4.5]dec-7-yl]methyl}-1H-benzimidazole-6-carbonitrile To a 3 L flask fitted with an overhead stirrer was added 3-({[(2R,3R,7S)-2,3-diphenyl-1,4-dioxaspiro[4.5]dec-7-yl]methyl}amino)-4-nitrobenzonitrile (131 g, 279 mmol), iron (156 g, 2790 mmol), MeOH (1 L), EtOAc (1 L), trimethyl orthoformate (0.308 L, 2790 mmol) and formic acid (0.107 L, 2790 mmol). The mixture was heated to 64° C. Every 15 min an additional 2-3 eq of iron, formic acid and trimethyl orthoformate was added. After 3 h, the solution was cooled to RT and filtered through Celite and washed with EtOAc. The filtrate was concentrated to give 1-{[(2R,3R,7S)-2,3-diphenyl-1,4-dioxaspiro[4.5]dec-7-yl]methyl}-1H-benzimidazole-6-carbonitrile (125 g, 100% yield). MS (m/z) 450.2 $(M+H^+)$. The product was used without further purification.

1-{[(1S)-3-Oxocyclohexaneyl]methyl}-1H-benzimidazole-6-carbonitrile

A mixture of 1-{[(2R,3R,7S)-2,3-diphenyl-1,4-dioxaspiro[4.5]dec-7-yl]methyl}-1H-benzimidazole-6-carbonitrile (125 g, 279 mmol) in formic acid (1.5 L) was heated to 70° C. overnight. Then the formic acid was removed via concentration, and the mixture was diluted with DCM and saturated aq NaHCO₃ till basic. The mixture was extracted with DCM (3×). The organic layers were dried over Na₂SO₄, filtered and concentrated and azeotroped with EtOAc. EtOAc (250 mL) was then added and the mixture was stirred at RT which led to solids forming. The slurry was stirred at RT for 15 min and then hexane (500 mL) was added slowly. The slurry was allowed to stir for 3 days at RT and then filtered and washed with hexane. The solids were dried under reduced pressure to give ~61 g product. The filtrate was concentrated and purified via normal phase chromatography (Combiflash Rf, (2×330 g silica column), solid load, 100 mL/min, EtOAc/CH₂Cl₂ 0-100% over 20 min, then 0-10% MeOH/CH₂Cl₂ over 10 min, holding at 10% MeOH/DCM until) all product had eluted from column) to afford the desired product as a tan solid (~7 g). The material was dissolved in EtOAc (15 mL), and heated to reflux. Next, hexane was added until solids started to form. Heating was stopped and the solution was allowed to cool to RT. Stirring was continued overnight at RT. Filtration of the slurry gave the desired product as a light tan powder (3.5 g). MS (m/z) 254.1 (M+H⁺).

Intermediate 3

1-{[(3S,5S)-5-Methyl-1-oxaspiro[2,5]oct-5-yl]methyl}-1H-benzimidazole-6-carbonitrile

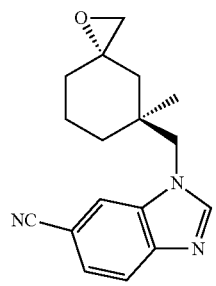 [SMILES: C[C@]1(Cn2cnc3ccc(C#N)cc32)CCC[C@@]2(CO2)C1]

Route 1:

To a 2 L flask was added DMSO (604 mL) and 1-{[(1S)-1-methyl-3-oxocyclohexaneyl]methyl}-1H-benzimidazole-6-carbonitrile (121 g, 453 mmol). The solution was stirred and heated to ~35° C. to get all solids to go into solution. Next, trimethylsulfonium iodide (112 g, 543 mmol) was added followed by potassium tert-butoxide (60.9 g, 543 mmol). The mixture was allowed to stir and cool to RT. After 1 h, LCMS indicated the reaction was complete. Next, the DMSO solution was added to a separatory funnel and diluted with 3 L water and 1 L DCM. The DCM was separated, and the water was extracted with DCM (3×500 mL). The combined DCM extracts were washed with brine (2 L) then dried over Na₂SO₄, filtered and concentrated. Half of the residue was purified by prep-SFC (total of 450-injections, 6 min run each) using the following conditions: Column: GreenSep Silica (ES Industries), 25 cm×21.2 mm, Co-solvent: MeOH, % Co-solvent: 25% Isocratic, Flow rate=60 g/min, Temperature: ambient. Following the purification of this material, the pressure on the SFC was too high to continue purification. The remaining dark MeOH solution of material was concentrated (~70 g), dissolved in DCM and purified on the ISCO: 8×220 g column, 75 mL/min, 0-3.5% MeOH/DCM (0.1% TEA) over 15 min, then holding at 3.5% MeOH until product eluted. Some early fractions contained pure cis product. These were concentrated and combined with the cis product from the SFC purification. The late fractions, which were yellow, were concentrated and re-purified on 3×220 g columns the same way as described above. In this case, some late fractions were pure trans product, and these fractions were isolated and combined with the trans product from the SFC. All mixed fractions were combined and concentrated to give ~36 g of material. This was then purified on the SFC and resulted in no pressure problems. Concentration of the appropriate fractions afforded 42.7 g (33.5% yield) of trans epoxide (1-{[(3S,5S)-5-methyl-1-oxaspiro[2.5]oct-5-yl]methyl}-1H-benzimidazole-6-carbonitrile) and 72.7 g (57% yield) of cis epoxide (1-{[(3R,5S)-5-methyl-1-oxaspiro[2.5]oct-5-yl]methyl}-1H-benzimidazole-6-carbonitrile). MS (m/z) 282.2 (M+H⁺). Route 2: The cis epoxide can be converted to trans-epoxide using the two step procedure described below.

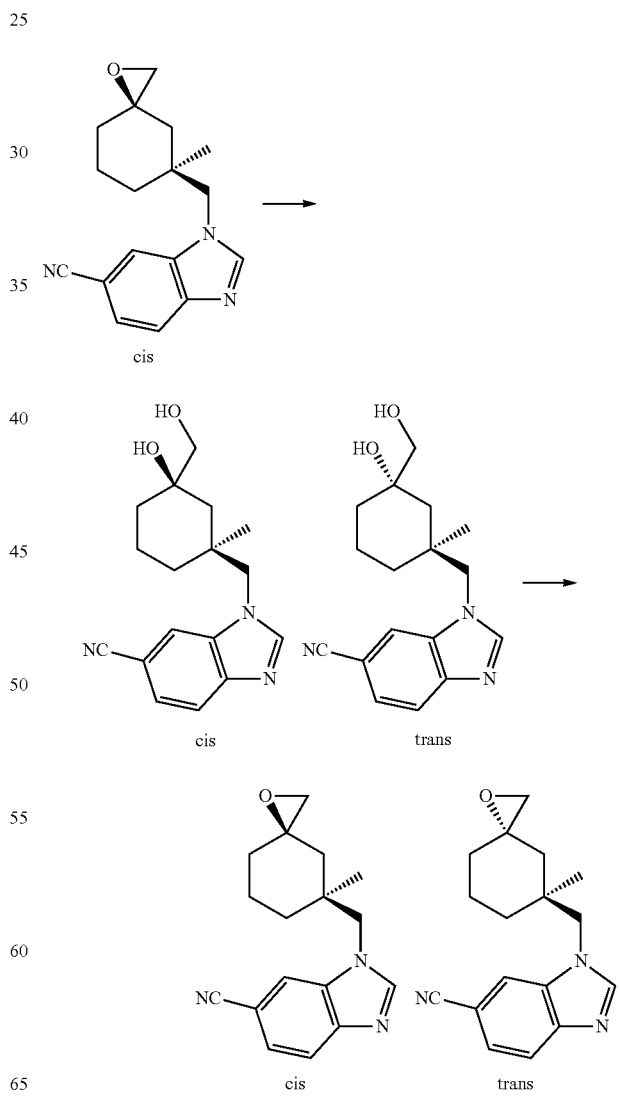

1-{[(1S,3S)-3-Hydroxy-3-(hydroxymethyl)-1-methylcyclohexaneyl]methyl}-1H-benzimidazole-6-carbonitrile To a 3 L flask was added 1-{[(3R,5S)-5-methyl-1-oxaspiro [2.5]oct-5-yl]methyl}-1H-benzimidazole-6-carbonitrile (94.7 g, 337 mmol). The material was azeotroped two times with EtOAc to remove any trace amounts of MeOH from the SFC. Next, to the residue was added DMF (731 mL) and water (731 mL). The solution was cooled to ~18° C. (with an ice water bath). Next, a solution of TFA (51.9 mL, 673 mmol) in water (731 mL) added (pre-cooled to ~10° C.). The entire solution was then cooled with an ice water bath to ~10° C. The temperature was held around 10° C. for about 2.5 h then allowed to warm to RT and stir overnight. The next day, DCM (500 mL) was added, and the solution was made basic by slowly adding 6N NaOH. The mixture was added to a separatory funnel, the DCM separated and the aqueous layer diluted with 6N NaOH (300 mL), and then extracted with DCM (8×250 mL). The combined organic extracts were concentrated under reduced pressure to remove as much DMF as possible. The residue was dissolved in DCM (250 mL) and stirred at RT to crystallize the trans diol. After stirring overnight, the solution was cooled to ~10° C., and the solids were filtered off, washed with DCM and dried under reduced pressure. This yielded 49.15 g of 1-{[(1S,3S)-3-hydroxy-3-(hydroxymethyl)-1-methylcyclohexaneyl]methyl}-1H-benzimidazole-6-carbonitrile (trans diol) as a white solid. The filtrate (~60 g material, a mixture of cis-diol, trans-diol, and elimination side products) was concentrated, loaded onto silica gel and split into 3 equal portions and purified on the ISCO RF (3×330 g column): 0-5% MeOH/DCM over 15 min, hold at 5% for 10 min, then 5-25% over 10 min, then hold at 25%. The trans diol product was combined with the solids from the crystallization and used without further purification. MS (m/z) 300.2 (M+H⁺).

1-{[(3S,5S)-5-Methyl-1-oxaspiro[2.5]oct-5-yl]methyl}-1H-benzimidazole-6-carbonitrile To a 1 L flask was added 1-{[(1S,3S)-3-hydroxy-3-(hydroxymethyl)-1-methylcyclohexaneyl]methyl}-1H-benzimidazole-6-carbonitrile (21.2 g, 70.8 mmol) and DCM (698 mL) and the temperature was lowered to 5° C. Next DMAP (6.49 g, 53.1 mmol), tosyl-Cl (20.25 g, 106 mmol) and triethylamine (20.23 mL, 145 mmol) were added. The solution was allowed to stir and warm to RT. Stirring was continued for 18 h and then the solution was added to a separatory funnel and diluted with saturated aq NaHCO₃ (1 L). The DCM was separated, and washed sequentially with saturated aq NH₄Cl, then saturated aq NaHCO₃. The DCM was then passed over a phase separator to remove leftover water, concentrated, and taken directly onto the next step. To the yellow residue was added methanol (698 mL) followed by K₂CO₃ (10.77 g, 78 mmol). The mixture was stirred at RT for 3 h. Following completion, the solution was filtered, and the solids were washed with MeOH. The mixture was then diluted with DCM (500 mL) and saturated aq NaHCO₃ (1 L). The solution was added to a 3 L separatory funnel, and the aqueous layer extracted three times with DCM. The combined DCM extracts were washed with brine and then dried over Na₂SO₄, filtered and concentrated. The crude solid was azeotroped with EtOAc two times to give a yellow residue. The residue was dried under reduced pressure to give 1-{[(3S,5S)-5-methyl-1-oxaspiro[2.5]oct-5-yl]methyl}-1H-benzimidazole-6-carbonitrile as a yellow solid (19.9 g, 95% yield). MS (m/z) 282.2 (M+H⁺).

Intermediate 4

1-[(3S,5S)-1-Oxaspiro[2.5]oct-5-ylmethyl]-1H-benzimidazole-6-carbonitrile

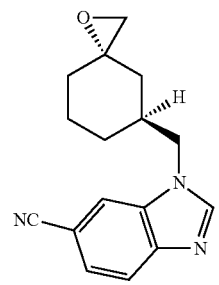 [SMILES: N#Cc1ccc2ncn(C[C@H]3CCC[C@@]4(CO4)C3)c2c1]

A solution of trimethylsulfoxonium iodide (63.1 g, 287 mmol) in DMSO (500 mL) was added sodium hydride (11.46 g, 287 mmol) in portions under nitrogen. The resulting mixture was stirred at RT for 1 h. To the mixture was added a solution of 1-{[(1S)-3-oxocyclohexaneyl]methyl}-1H-benzimidazole-6-carbonitrile (60.5 g, 239 mmol) in DMSO (500 mL) dropwise under nitrogen. The resulting light brown solution was stirred at RT for 1 h. LCMS indicated the mixture was 9:1 trans/cis. Next, the DMSO solution was poured into 2 L water, and then extracted with DCM (3×). The combined DCM extracts were washed with water (2 L) and brine (2 L), and the organic layers were dried over Na₂SO₄, filtered and concentrated to give 68 g of a tan solid. To the residue was added 500 mL of EtOAc. The mixture was heated to reflux with stirring. Once all solids were in solution, the EtOAc was allowed to evaporate off until the amount of EtOAc was 320 mL, then the heating was stopped and the solution was allowed to cool to RT with stirring. Stirring was continued overnight at RT, then cooled to 5° C. and let stir for 3 h. The slurry was then filtered, washed with minimal amount of cold EtOAc, followed by hexane. The resulting tan solid was dried under reduced pressure to give 1-[(3S,5S)-1-oxaspiro[2.5] oct-5-ylmethyl]-1H-benzimidazole-6-carbonitrile (46 g of a 95:5 trans:cis mixture). The filtrate was concentrated to give 1-[(3S,5S)-1-oxaspiro[2.5]oct-5-ylmethyl]-1H-benzimidazole-6-carbonitrile (22 g, 61:39 trans:cis mixture) and the process repeated. MS (m/z) 268 (M+H⁺).

Example 1

1-(((5S,7S)-7-methyl-3-neopentyl-2-oxo-1-oxa-3-azaspiro[4.5]decan-7-yl)methyl)-1H-benzo[d]imidazole-6-carbonitrile

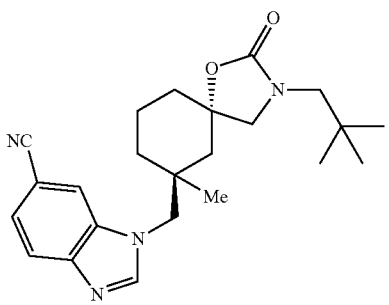 [SMILES: CC(C)(C)CN1C[C@@]2(CCC[C@](C)(Cn3cnc4ccc(C#N)cc43)C2)OC1=O]

Intermediate 3 (0.250 g, 0.889 mmol) was dissolved in isopropanol (10 mL) and treated with neopentylamine (0.387 g, 4.44 mmol). The reaction was stirred at 80° C. for 18 h. The reaction was cooled to rt and concentrated. The crude product was redissolved in DCM and hexanes and concentrated again. This sequence was repeated to remove any trace isopropanol. The crude aminoalcohol was redissolved in 1,4-dioxane (5 mL) and treated with CDI (0.432 g, 2.67 mmol). The resulting solution was stirred at 110° C. for 3 days and then cooled to rt. The crude reaction mixture was concentrated and redissolved in a minimum of DMSO for purification by reverse-phase HPLC (Sunfire Prep C18 column (30×150 mm); 16 min run; 50 mL/min flow rate with at-column dilution; Solvent A: MeCN/0.1% TFA, Solvent B: water/0.1 TFA, gradient: 20-60% solvent A) to yield the title compound (0.230 g, 64% yield) as the TFA salt. ¹H NMR (400 MHz, CDCl₃) δ 8.77 (s, 1H), 8.08 (d, J=8.53 Hz, 1H), 7.91 (s, 1H), 7.70 (dd, J=1.51, 8.53 Hz, 1H), 4.52 (dd, J=14.81, 33.63 Hz, 2H), 3.44 (dd, J=8.78, 22.09 Hz, 2H), 3.18 (d, J=14.30 Hz, 1H), 2.95 (d, J=14.05 Hz, 1H), 2.20 (d, J=14.05 Hz, 1H), 1.94-2.07 (m, 2H), 1.71-1.88 (m, 2H), 1.33-1.57 (m, 3H), 0.99 (s, 9H), 0.94 (s, 3H). MS (m/z) 395.2 (M+H⁺).

The following compounds were prepared using either Intermediate 3 or Intermediate 4 (optically pure or racemic versions) and the requisite amine (either purchased or described as Intermediates or synthesized using standard chemical transformations known to those skill-in-the-art) according to procedures analogous to that described in the synthesis of Example 1. As is appreciated by those skilled in the art, these analogous examples may involve variations in general reaction conditions.

| Ex | Name | Structure | MS (m/z) |
|---|---|---|---|
| 2 | 1-(((5S,7S)-3-neopentyl-2-oxo-1-oxa-3-azaspiro[4.5]decan-7-yl)methyl)-1H-benzo[d]imidazole-6-carbonitrile | 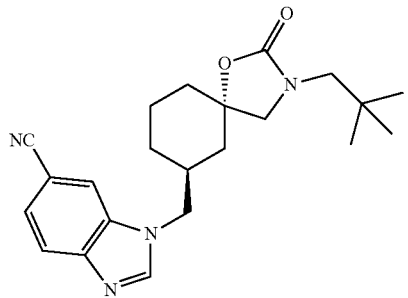 [SMILES: CC(C)(C)CN1C[C@@]2(CCC[C@H](Cn3cnc4ccc(C#N)cc43)C2)OC1=O] | 381.2 (M + H⁺) |
| 3 | 1-(((5S,7S)-2-oxo-3-((trimethylsilyl)methyl)-1-oxa-3-azaspiro[4.5]decan-7-yl)methyl)-1H-benzo[d]imidazole-6-carbonitrile | 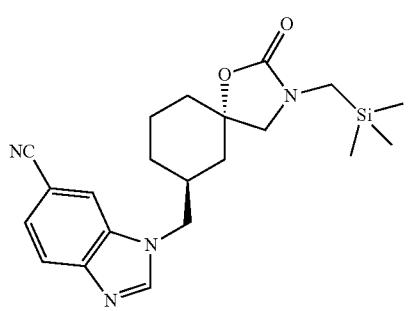 [SMILES: C[Si](C)(C)CN1C[C@@]2(CCC[C@H](Cn3cnc4ccc(C#N)cc43)C2)OC1=O] | 397.1 (M + H⁺) |

-continued

| Ex | Name | Structure | MS (m/z) |
|---|---|---|---|
| 4 | 1-(((5S,7S)-3-((1-(methoxymethyl)cyclopentyl)methyl)-2-oxo-1-oxa-3-azaspiro[4.5]decan-7-yl)methyl)-1H-benzo[d]imidazole-6-carbonitrile | 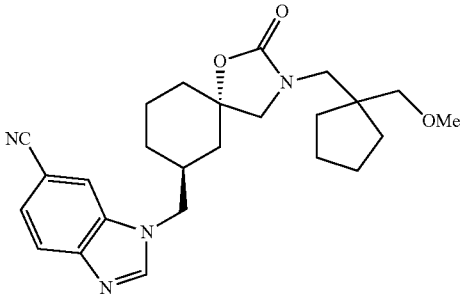 [SMILES: COCC1(CN2C[C@@]3(CCC[C@H](Cn4cnc5ccc(C#N)cc54)C3)OC2=O)CCCC1] | 437.3 (M + H+) |
| 5 | 1-(((5S,7S)-3-((1-ethylcyclobutyl)methyl)-2-oxo-1-oxa-3-azaspiro[4.5]decan-7-yl)methyl)-1H-benzo[d]imidazole-6-carbonitrile | 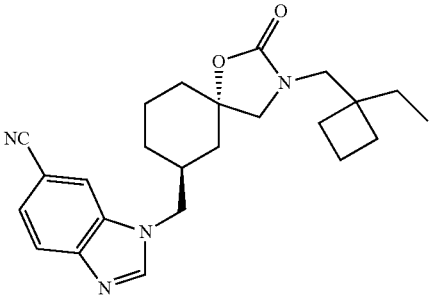 [SMILES: CCC1(CN2C[C@@]3(CCC[C@H](Cn4cnc5ccc(C#N)cc54)C3)OC2=O)CCC1] | 407.2 (M + H+) |
| 6 | 1-(((5S,7S)-3-((2-methyltetrahydrofuran-2-yl)methyl)-2-oxo-1-oxa-3-azaspiro[4.5]decan-7-yl)methyl)-1H-benzo[d]imdazole-6-carbonitrile | 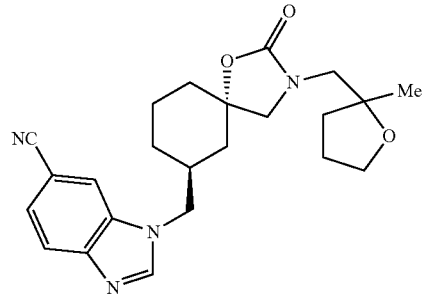 [SMILES: CC1(CN2C[C@@]3(CCC[C@H](Cn4cnc5ccc(C#N)cc54)C3)OC2=O)CCCO1] | 409.2 (M + H+) |
| 7 | 1-(((5S,7S)-7-methyl-3-((2-methyltetrahydrofuran-2-yl)methyl)-2-oxo-1-oxa-3-azaspiro[4.5]decan-7-yl)methyl)-1H-benzo[d]imidazole-6-carbonitrile | 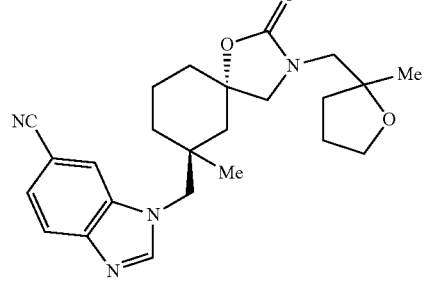 | 423.2 (M + H+) |
| 8 | 1-(((5S,7S)-3-((2-ethyltetrahydrofuran-2-yl)methyl)-2-oxo-1-oxa-3-azaspiro[4.5]decan-7-yl)methyl)-1H-benzo[d]imidazole-6-carbonitrile | 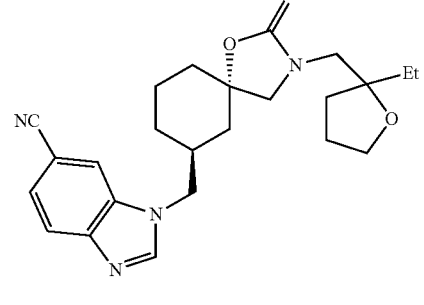 | 423.2 (M + H+) |

| Ex | Name | Structure | MS (m/z) |
|---|---|---|---|
| 9 | 1-(((5S,7S)-7-methyl-2-oxo-3-(((S)-tetrahydrofuran-2-yl)methyl)-1-oxa-3-azaspiro[4.5]decan-7-yl)methyl)-1H-benzo[d]imidazole-6-carbonitrile | 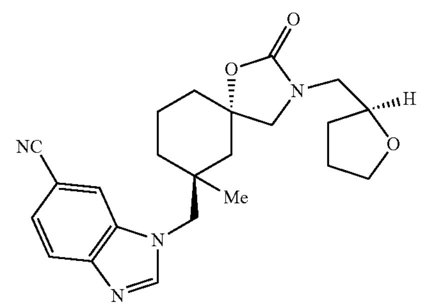 [SMILES: C[C@]1(Cn2cnc3ccc(C#N)cc32)CCC[C@@]2(CN(C[C@@H]3CCCO3)C(=O)O2)C1] | 409.0 (M + H⁺) |
| 10 | 1-(((5S,7S)-3-(2-ethoxy-2-methylpropyl)-2-oxo-1-oxa-3-azaspiro[4.5]decan-7-yl)methyl)-1H-benzo[d]imidazole-6-carbonitrile | 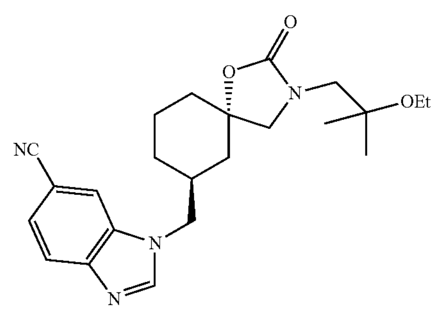 [SMILES: CCOC(C)(C)CN1C[C@@]2(CCC[C@H](Cn3cnc4ccc(C#N)cc43)C2)OC1=O] | 411.2 (M + H⁺) |
| 11 | 1-(((5S,7S)-3-((2-methyltetrahydro-2H-pyran-2-yl)methyl)-2-oxo-1-oxa-3-azaspiro[4.5]decan-7-yl)methyl)-1H-benzo[d]imidazole-6-carbonitrile | 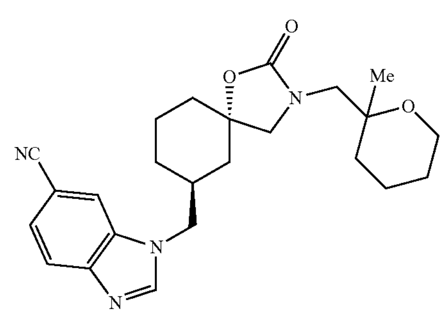 [SMILES: CC1(CN2C[C@@]3(CCC[C@H](Cn4cnc5ccc(C#N)cc54)C3)OC2=O)CCCCO1] | 423.2 (M + H⁺) |
| 12 | 1-(((5S,7S)-3-(3-isopropoxy-2,2-dimethylpropyl)-2-oxo-1-oxa-3-azaspiro[4.5]decan-7-yl)methyl)-1H-benzo[d]imidazole-6-carbonitrile | 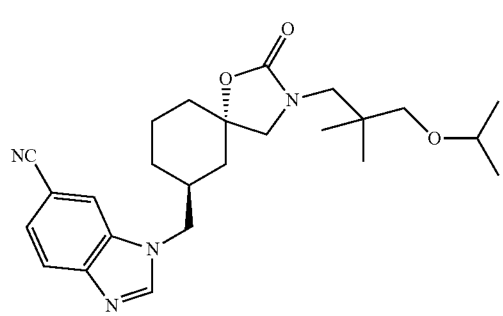 [SMILES: CC(C)OCC(C)(C)CN1C[C@@]2(CCC[C@H](Cn3cnc4ccc(C#N)cc43)C2)OC1=O] | 439.2 (M + H⁺) |

-continued

| Ex | Name | Structure | MS (m/z) |
|---|---|---|---|
| 13 | 1-(((5S,7S)-3-(2-cyano-2-methylpropyl)-2-oxo-1-oxa-3-azaspiro[4.5]decan-7-yl)methyl)-1H-benzo[d]imidazole-6-carbonitrile | 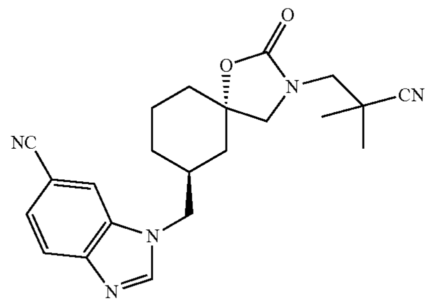 [SMILES: CC(C)(C#N)CN1C[C@@]2(CCC[C@H](Cn3cnc4ccc(C#N)cc43)C2)OC1=O] | 392.2 (M + H+) |
| 14 | 1-(((5S,7S)-3-(2,2-dimethyl-3-(trifluoromethoxy)propyl)-2-oxo-1-oxa-3-azaspiro[4.5]decan-7-yl)methyl)-1H-benzo[d]imidazole-6-carbonitrile | 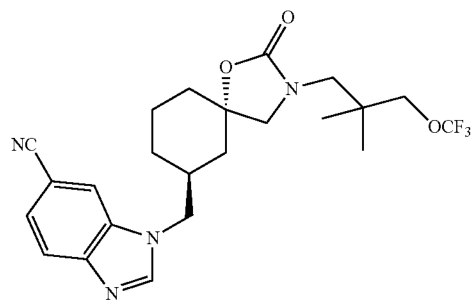 [SMILES: CC(C)(COC(F)(F)F)CN1C[C@@]2(CCC[C@H](Cn3cnc4ccc(C#N)cc43)C2)OC1=O] | 465.2 (M + H+) |
| 15 | 1-(((5S,7S)-3-(2,2-dimethylcyclohexyl)-2-oxo-1-oxa-3-azaspiro[4.5]decan-7-yl)methyl)-1H-benzo[d]imidazole-6-carbonitrile | 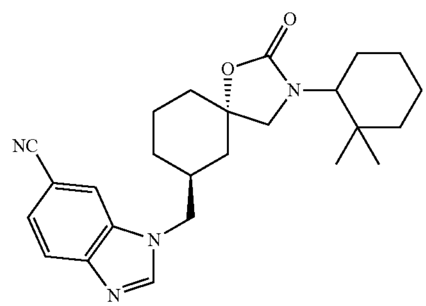 [SMILES: CC1(C)CCCCC1N1C[C@@]2(CCC[C@H](Cn3cnc4ccc(C#N)cc43)C2)OC1=O] | 421.2 (M + H+) |
| 16 | methyl 3-(-7-((6-cyano-1H-benzo[d]imidazol-1-yl)methyl)-2-oxo-1-oxa-3-azaspiro[4.5]decan-3-yl)-2,2-dimethylpropanoate | 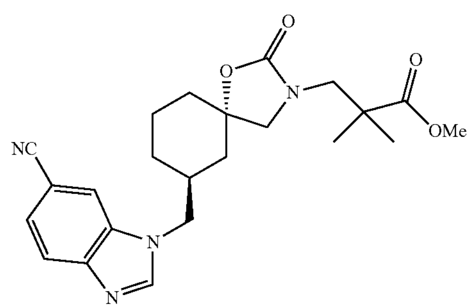 [SMILES: COC(=O)C(C)(C)CN1C[C@@]2(CCC[C@H](Cn3cnc4ccc(C#N)cc43)C2)OC1=O] | 425.3 (M + H+) |
| 17 | 5-fluoro-1-((-2-oxo-3-(2,2,3,3,3-pentafluoropropyl)-1-oxa-3-azapsiro[4.5]decan-7-yl)methyl)-1H-benzo[d]imidazole-6-carbonitrile | 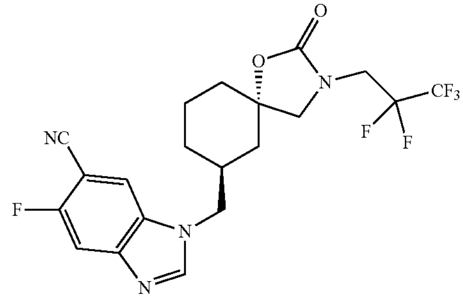 [SMILES: N#Cc1cc2c(cc1F)ncn2C[C@H]1CCC[C@]2(C1)CN(CC(F)(F)C(F)(F)F)C(=O)O2] | 461.1 (M + H+) |

Example 18

7-((6-chloro-1H-benzo[d]imidazol-1-yl)methyl)-7-methyl-3-neopentyl-1-oxa-3-azaspiro[4.5]decan-2-one

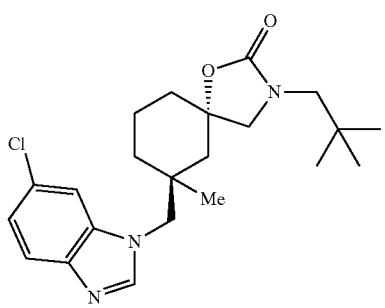 [SMILES: CC(C)(C)CN1C[C@@]2(CCC[C@](C)(Cn3cnc4ccc(Cl)cc43)C2)OC1=O]

Intermediate 5 methyl 3-hydroxycyclohexanecarboxylate

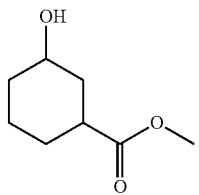

Methyl 3-hydroxycyclohexanecarboxylate (70.0 g, 460 mmol) and rhodium on alumina (7.5 g, 460 mmol) were added to a nitrogen purged 2 L Parr flask. Ethanol (300 mL) was carefully added, and the flask was then shaken under hydrogen pressure (55 psi) on the Parr hydrogenator for 18 h. The Parr flask was carefully purged with $N_2$. The reaction mixture was filtered through a plug of celite, and the eluent was evaporated to provide the crude title compound which was used without further purification.

Intermediate 6 methyl 3-oxocyclohexanecarboxylate

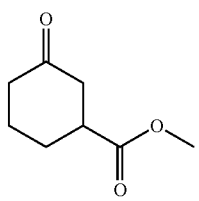

Ruthenium(IV) oxide hydrate (1.47 g, 11.1 mmol) and sodium bromate (100 g, 664 mmol) were combined in $Et_2O$ (600 mL) and water (300 mL). The resulting black mixture was stirred for 10 min and cooled in an ice bath. The methyl 3-hydroxycyclohexanecarboxylate (35 g, 221 mmol) was dissolved in $Et_2O$ (to bring total volume to 100 mL) and added dropwise to the ice cold reaction mixture. The temperature was not allowed to go above 30° C. The reaction mixture was stirred for 1 h with the reaction temperature at ~15° C. Isopropanol was carefully added to the reaction mixture at a rate necessary to keep the reaction temperature at ~27° C. The layers were separated and the organic layers were washed with $Et_2O$. The combined organics were washed with saturated, aqueous $NaHCO_3$ solution and brine. The organics were then dried over $MgSO_4$, filtered, and concentrated to provide the crude title compound (34.5 g, 100% crude yield) which was used without further purification. $^1H$ NMR (400 MHz, $CDCl_3$) δ 3.68 (s, 3H), 2.79 (m, 1H), 2.52 (d, J=7.78 Hz, 2H), 2.23-2.42 (m, 2H), 1.98-2.15 (m, 2H), 1.82 (d, J=10.29 Hz, 1H), 1.61-1.77 (m, 1H).

Intermediate 7

Methyl 1-oxaspiro[2,5]octane-5-carboxylate

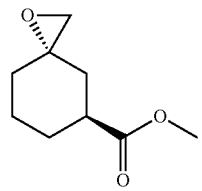

To a solution of trimethylsulfoxonium iodide (53.3 g, 242 mmol) in dry DMSO (300 mL) under $N_2$, was added NaH (9.69 g, 242 mmol) portionwise over 30 min. This light yellow mixture was stirred at rt for 1 h The reaction mixture was cooled in an ice bath and treated with methyl 3-oxocyclohexanecarboxylate (29.0 g, 186 mmol) dropwise while maintaining a temperature at or below 27° C. The resulting reaction mixture was allowed to warm slowly to rt and stir overnight. The reaction was diluted with water and extracted with DCM. The combined organics were washed with water, dried over $MgSO_4$, filtered, and concentrated to provide the crude title compound (31.8 g, 85% crude yield) which was used without further purification. $^1H$ NMR (400 MHz, $CDCl_3$) δ 3.66 (s, 3H), 2.71 (m, 1H), 2.65 (d, J=1.76 Hz, 2H), 2.00 (dd J=11.8, 13.6 Hz, 2H), 1.74-1.85 (m, 2H), 1.60-1.74 (m, 1H), 1.40-1.56 (m, 2H), 1.17-1.32 (m, 1H).

Intermediate 8 methyl 3-neopentyl-2-oxo-1-oxa-3-azaspiro[4.5]decane-7-carboxylate

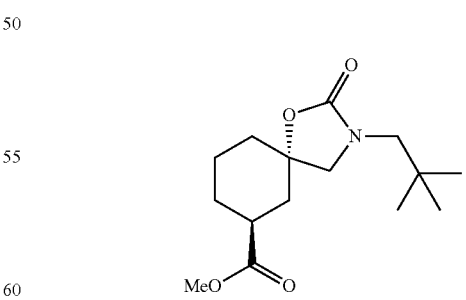

To a solution containing racemic methyl 1-oxaspiro[2.5]octane-5-carboxylate (34.2 g, 201 mmol), dissolved in MeOH (540 mL) was added neopentyl amine (18.4 g, 211 mmol). The reaction was heated at reflux for 20 h. The reaction mixture was cooled to rt and concentrated to an oil. The crude material was dissolved in 1,4-dioxane (540 mL) and treated with CDI (42.3 g, 261 mmol). The reaction was again heated at reflux. After 14 h, the reaction was concentrated to a thick oil, taken up in water, and acidified to pH 3. The product was extracted into DCM (5×300 mL). The combined organics were washed with concentrated aqueous $H_3PO_4$ solution followed by brine. The organics were then dried over sodium sulfate, filtered, and concentrated to a waxy white solid. This solid was purified on a 330 g silica gel column (0-60% EtOAc/hexanes, 30 min gradient; 100 mL/min elution; 254 nm detection) to provide the title compound (40.8 g, 69.7%) as a white solid. $^1$H NMR (400 MHz, $CDCl_3$) δ 3.69 (s, 3H), 3.38 (dd, J=8.78, 13.05 Hz, 2H), 3.01 (dd, J=14.05, 25.35 Hz, 2H), 2.17-2.28 (m, 1H), 2.02-2.12 (m, 1H), 1.98 (dd, J=2.13, 13.68 Hz, 1H), 1.71-1.86 (m, 2H), 1.54-1.65 (m, 2H), 1.29-1.47 (m, 2H), 0.97 (s, 9H).

Intermediate 9 methyl 7-methyl-3-neopentyl-2-oxo-1-oxa-3-azaspiro[4.5]decane-7-carboxylate

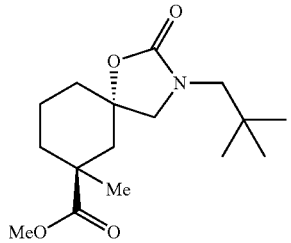 [SMILES: COC(=O)[C@@]1(C)CCC[C@@]2(CN(CC(C)(C)C)C(=O)O2)C1]

To a 78° C. solution of methyl 3-neopentyl-2-oxo-1-oxa-3-azaspiro[4.5]decane-7-carboxylate (15.0 g, 52.9 mmol) in THF (41.0 mL) under $N_2$ was added sodium bis(trimethylsilyl)amide, 1 M in THF (238 mL, 238 mmol) over 1 h using an addition funnel. The reaction mixture was stirred at −78° C. for 3 h. Iodomethane (14.9 mL, 238 mmol) was added, and the reaction was stirred at −78° C. for an additional 2 h. The reaction was quenched at −78° C. with water (5 mL) and diluted with brine (200 mL). The product was extracted into EtOAc (3×200 mL). The combined organics were dried over sodium sulfate, filtered, and concentrated to a light yellow solid. The solid was suspended in $Et_2O$ (75 mL) and collected in a frit. The collected solids were washed with cold $Et_2O$ (4×10 mL) and dried to afford the title compound (13.4 g, 81% yield) as a light yellow solid. $^1$H NMR (400 MHz, $CDCl_3$) δ 3.69 (s, 3H), 3.40 (d, J=8.78 Hz, 1H), 3.29 (d, J=8.78 Hz, 1H), 3.06 (d, J=14.05 Hz, 1H), 2.92 (d, J=14.05 Hz, 1H), 2.16 (d, J=14.05 Hz, 1H), 1.77-1.93 (m, 4H), 1.43-1.69 (m, 3H), 1.35 (s, 3H), 0.96 (s, 9H). MS (m/z) 298.1 (M+H$^+$).

Intermediate 10

7-(hydroxymethyl)-7-methyl-3-neopentyl-1-oxa-3-azaspiro[4.5]decan-2-one

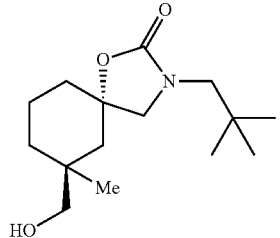 [SMILES: CC(C)(C)CN1C[C@@]2(CCC[C@](C)(CO)C2)OC1=O]

Step 1:

To a −78° C. solution of methyl 7-methyl-3-neopentyl-2-oxo-1-oxa-3-azaspiro[4.5]decane-7-carboxylate (24.2 g, 82.0 mmol) in THF (204 mL) under $N_2$ was slowly added lithium aluminium hydride, 1 M in THF (122 mL, 122 mmol). After stirring 1 h at −78° C., additional lithium aluminum hydride, 1 M in THF (0.061 mL, 61.0 mmol) was added. After 3 h the reaction was quenched with water (5 mL) and diluted with 4 N HCl (500 mL). The product was extracted into EtOAc (3×300 mL). The combined organics were dried over $MgSO_4$, filtered, and concentrated onto florisil for purification on a 330 g silica gel column (10-50% EtOAc/hexanes, 30 min gradient; 50% EtOAc/hexanes, 15 min; 50-75% EtOAc/hexanes, 10 min gradient; 75% EtOAc/hexanes, 10 min; 100 mL/min elution; 254 nm detection) to provide the title compound (14.7 g) as an orange oil and the intermediate aldehyde product (7.19 g) as a yellow solid.

Step 2:

The 7-methyl-3-neopentyl-2-oxo-1-oxa-3-azaspiro[4.5]decane-7-carbaldehyde intermediate product from step 1 (7.19 g, 26.9 mmol) was dissolved in THF (108 mL) and MeOH (27 mL) and treated with sodium borohydride (1.22 g, 32.3 mmol). The reaction was stirred at rt for 2 h and quenched with water (1 mL) and 1 N HCl (75 mL). The product was extracted into EtOAc (2×100 mL). The combined organics were dried over $Na_2SO_4$, filtered, and concentrated onto florisil for purification on a 120 g silica gel column (10-50% EtOAc/hexanes, 30 min gradient; 50% EtOAc/hexanes, 10 min; 50-75% EtOAc/hexanes, 10 min gradient; 85 mL/min elution; 254 nm detection) to afford the title compound (6.23 g, 75% combined yield with step 1). $^1$H NMR (400 MHz, $CDCl_3$) δ 3.30-3.38 (m, 2H), 3.29 (s, 2H), 3.06 (d, J=14.05 Hz, 1H), 2.94 (d, J=14.05 Hz, 1H), 1.95-2.03 (m, 1H), 1.64-1.72 (m, 1H), 1.53-1.64 (m, 3H), 1.29-1.43 (m, 3H), 1.09 (s, 3H), 0.96 (s, 9H). MS (m/z) 270.2 (M+H$^+$).

Intermediate 11

7-(bromomethyl)-7-methyl-3-neopentyl-1-oxa-3-azaspiro[4.5]decan-2-one

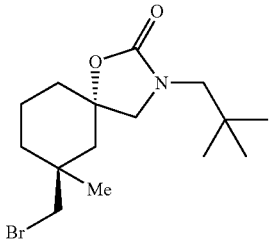

To a colorless solution of 7-(hydroxymethyl)-7-methyl-3-neopentyl-1-oxa-3-azaspiro[4.5]decan-2-one (14.7 g, 54.6 mmol) in MeCN (273 ml) was added dibromotriphenylphosphorane (34.6 g, 82.0 mmol). The reaction was stirred at rt for 3 h and then heated to 80° C. for 42 h. The reaction was cooled to rt and concentrated onto florisil for purification on a 220 g silica gel column (5-15% EtOAc/hexanes, 30 min gradient; 15% EtOAc/hexanes, 10 min; 15-50% EtOAc/hexanes, 15 min gradient; 50% EtOAc/hexanes, 15 min; 50-100% EtOAc/hexanes, 5 min gradient; 100% EtOAc, 5 min; 100 mL/min elution; 254 nm detection) to yield the title compound (9.7 g, 54% yield). $^1$H NMR (400 MHz, $CDCl_3$) δ 3.35 (dd, J=8.78, 12.05 Hz, 2H), 3.26 (s, 2H), 3.08 (d, J=14.05 Hz, 1H), 2.93 (d, J=14.05 Hz, 1H), 1.96-2.03 (m, 1H), 1.78 (dt, J=1.95, 14.18 Hz, 1H), 1.52-1.65 (m, 3H), 1.28-1.48 (m, 3H), 1.24 (s, 3H), 0.97 (s, 9H).

Intermediate 12

7-(azidomethyl)-7-methyl-3-neopentyl-1-oxa-3-azaspiro[4.5]decan-2-one

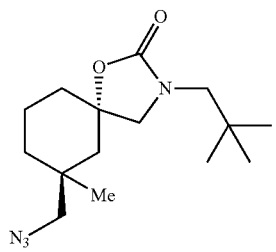 [SMILES: CC(C)(C)CN1C[C@@]2(CCC[C@](C)(CN=[N+]=[N-])C2)OC1=O]

To a solution of 7-(bromomethyl)-7-methyl-3-neopentyl-1-oxa-3-azaspiro[4.5]decan-2-one (11.3 g, 34.1 mmol) in DMSO (171 mL) was added sodium azide (2.89 g, 44.4 mmol). The reaction flask was placed behind a blast shield and heated to 80° C. for 4 days. The temperature was increased to 100° C. After 16 h, additional sodium azide (0.665 g, 10.23 mmol) was added to the reaction. After 19 h, the reaction was cooled to rt and diluted with water (300 mL). The product was extracted into EtOAc (2×300 mL). The combined organics were washed with water (3×400 mL). The organic layer was dried over MgSO$_4$, filtered, and concentrated to provide the title compound (10.0 g, 95% crude yield) as a light yellow solid. $^1$H NMR (400 MHz, CDCl$_3$) δ 3.33 (q, J=8.53 Hz, 2H), 3.09 (s, 2H), 3.06 (d, J=14.00 Hz, 1H), 2.94 (d, J=14.05 Hz, 1H), 1.96-2.05 (m, 1H), 1.83-1.96 (m, 1H), 1.69 (dt, J=2.04, 14.24 Hz, 1H), 1.59-1.65 (m, 1H), 1.47 (d, J=14.05 Hz, 1H), 1.26-1.44 (m, 3H), 1.15 (s, 3H), 0.97 (s, 9H).

Intermediate 13

7-(aminomethyl)-7-methyl-3-neopentyl-1-oxa-3-azaspiro[4.5]decan-2-one

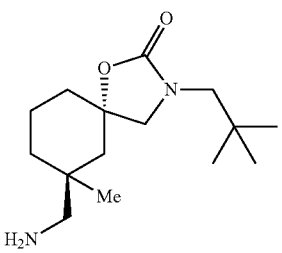 [SMILES: CC(C)(C)CN1C[C@@]2(CCC[C@](C)(CN)C2)OC1=O]

To a light green 0° C. solution of 7-(azidomethyl)-7-methyl-3-neopentyl-1-oxa-3-azaspiro[4.5]decan-2-one (10.0 g, 34.0 mmol) and nickel (II) chloride hexahydrate (8.07 g, 34.0 mmol) in MeOH (226 mL) was added sodium borohydride (1.93 g, 51.0 mmol) in six portions. The reaction quickly became black and was allowed to stir at 0° C. for 3 h. The reaction mixture was concentrated and partitioned between 1 N NaOH (350 mL) and EtOAc (350 mL). The biphasic mixture was filtered through celite, and the layers were separated. The aqueous layer was extracted with EtOAc (2×150 mL). The combined organics were dried over MgSO$_4$, filtered, and concentrated to afford the title compound (8.65 g, 90% crude yield) as a light yellow solid. $^1$H NMR (400 MHz, CDCl$_3$) δ 3.33 (dd, J=8.53, 13.80 Hz, 2H), 3.06 (d, J=14.05 Hz, 1H), 2.93 (d, J=14.05 Hz, 1H), 2.43 (s, 2H), 1.99 (dt, J=1.76, 13.55 Hz, 1H), 1.89 (dt, J=3.48, 13.87 Hz, 1H), 1.69 (d, J=14.05 Hz, 1H), 1.57 (dt, J=4.11, 13.87 Hz, 1H), 1.29-1.47 (m, 3H), 1.15-1.28 (m, 1H), 1.08 (s, 3H), 0.96 (s, 9H).

Intermediate 14

7-(((5-chloro-2-nitrophenyl)amino)methyl)-7-methyl-3-neopentyl-1-oxa-3-azaspiro[4.5]decan-2-one

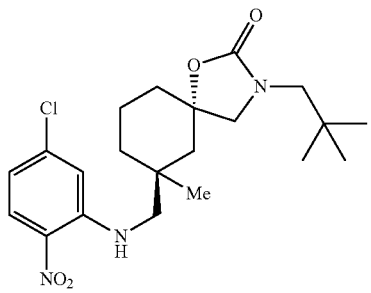

A solution containing 7-(aminomethyl)-7-methyl-3-neopentyl-1-oxa-3-azaspiro[4.5]decan-2-one (0.100 g, 0.373 mmol) in MeCN (5 mL) was treated with 4-chloro-2-fluoronitrobenzene (0.065 g, 0.373 mmol) and potassium carbonate (0.077 g, 0.559 mmol). The reaction mixture was heated to 50° C. and stirred for 18 h. Additional 4-chloro-2-fluoronitrobenzene (0.020 g, 0.114 mmol) was added, and the reaction was stirred at 50° C. for an additional 3 h. The reaction was cooled to rt and concentrated for purification on a 40 g silica gel column (0-100% EtOAc/hexanes, 25 min gradient; 40 mL/min elution; 254 nm detection) to afford the title compound (0.175 g, 100% yield). MS (m/z) 424.1 (M+H$^+$).

7-((6-chloro-1H-benzo[d]imidazol-1-yl)methyl)-7-methyl-3-neopentyl-1-oxa-3-azaspiro[4.5]decan-2-one A solution containing 7-(((5-chloro-2-nitrophenyl)amino) methyl)-7-methyl-3-neopentyl-1-oxa-3-azaspiro[4.5]decan-2-one (0.100 g, 0.236 mmol) in MeOH (5 mL) was treated with iron (325 mesh) (0.132 g, 2.36 mmol) followed by formic acid (0.090 mL, 2.359 mmol) and trimethyl orthoformate (0.261 mL, 2.359 mmol). The resulting mixture was heated at 65° C. for 18 h. LCMS indicated partial conversion to desired product. Additional iron (0.100 g, 1.79 mmol), formic acid (0.200 mL, 5.22 mmol), and trimethyl orthoformate (0.500 mL, 4.53 mmol) were added, and the reaction was stirred at 80° C. for 3 h. The reaction was cooled to rt and filtered through filter paper. The collected solids were washed with MeOH, and the combined MeOH washings and filtrate were concentrated. The crude product was purified by reverse-phase HPLC (Sunfire Prep C18 column (30×150 mm); 14 minute run; 40 mL/min flow rate with at-column dilution; Solvent A: MeCN/0.1% TFA, Solvent B: water/0.1 TFA, gradient: 10-90% solvent A) to afford the title compound (0.071 g, 52% yield) as the TFA salt. $^1$H NMR (400 MHz, CDCl$_3$) δ 8.88 (br. s., 1H), 7.89 (d, J=8.78 Hz, 1H), 7.56 (d, J=1.51 Hz, 1H), 7.49 (dd, J=1.63, 8.66 Hz, 1H), 7.27 (s, 1H), 4.08 (s, 2H), 3.26-3.40 (m, 1H), 3.06 (d, J=14.05 Hz, 1H), 2.92 (d, J=14.05 Hz, 1H), 2.05 (br. s., 1H), 1.79-1.99 (m, 2H), 1.69 (d, J=14.05 Hz, 1H), 1.58 (br. s., 1H), 1.42 (d, J=13.80 Hz, 1H), 1.28-1.37 (m, 2H), 1.27 (s, 3H), 0.95 (s, 9H). MS (m/z) 404.2 (M+H$^+$).

Example 19

7-((5,6-dichloro-1H-benzo[d]imidazol-1-yl)methyl)-7-methyl-3-neopentyl-1-oxa-3-azaspiro[4.5]decan-2-one

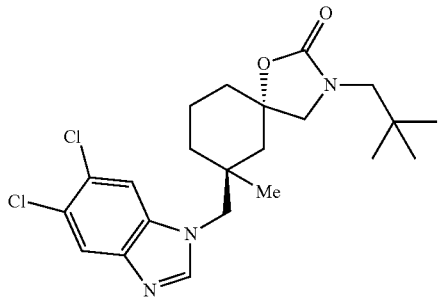 [SMILES: CC(C)(C)CN1C[C@@]2(CCC[C@](C)(Cn3cnc4cc(Cl)c(Cl)cc43)C2)OC1=O]

A rt solution containing Intermediate 11 (0.050 g, 0.150 mmol) in DMF (1.0 mL) was treated with 5,6-dichlorobenzimidazole (0.028 g, 0.150 mmol) and potassium carbonate (0.021 g, 0.150 mmol). The reaction mixture was stirred at rt for 1 h and then heated to 130° C. A catalytic amount of potassium iodide was added, and the reaction was stirred at 130° C. for 16 h. The reaction was cooled to rt, filtered through a frit, and concentrated. The crude product was purified using reverse-phase HPLC (Sunfire Prep C18 column (30×150 mm); 14 minute run; 40 mL/min flow rate with at-column dilution; Solvent A: MeCN/0.1% TFA, Solvent B: water/0.1% TFA, gradient: 10-90% solvent A) to afford the title compound (0.038 g, 43% yield) as the TFA salt. $^1$H NMR (400 MHz, CDCl$_3$) δ 8.63 (s, 1H), 8.06 (s, 1H), 7.64 (s, 1H), 5.52 (br. s., 1H), 4.03 (s, 2H), 3.33 (dd, J=8.78, 23.59 Hz, 2H), 2.99 (dd, J=14.05, 50.70 Hz, 2H), 2.06 (d, J=14.31 Hz, 1H), 1.79-1.98 (m, 2H), 1.54-1.75 (m, 2H), 1.39 (d, J=13.80 Hz, 2H), 1.28-1.35 (m, 1H), 1.26 (s, 3H), 0.95 (s, 9H). MS (m/z) 438.2 (M+H$^+$).

The following compounds were prepared using Intermediate 11 and the requisite substituted benzimidazole according to procedures analogous to that described for the conversion of Intermediate 11 to Example 19. As is appreciated by those skilled in the art, these analogous examples may involve variations in general reaction conditions.

| Ex | Name | Structure | MS (m/z) |
|---|---|---|---|
| 20 | 7-((5,6-difluoro-1H-benzo[d]imidazol-1-yl)methyl)-7-methyl-3-neopentyl-1-oxa-3-azaspiro[4.5]decan-2-one | 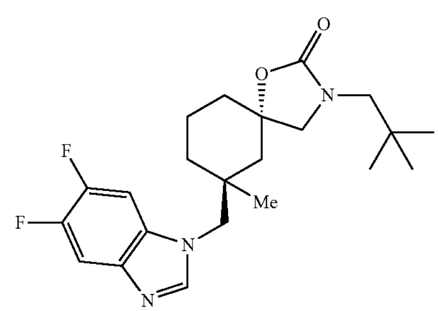 [SMILES: CC(C)(C)CN1C[C@@]2(CCC[C@](C)(Cn3cnc4cc(F)c(F)cc43)C2)OC1=O] | 406.2 (M + H$^+$) |
| 21 | 7-((5,6-dimethoxy-1H-benzo[d]imidazol-1-yl)methyl)-7-methyl-3-neopentyl-1-oxa-3-azaspiro[4.5]decan-2-one | 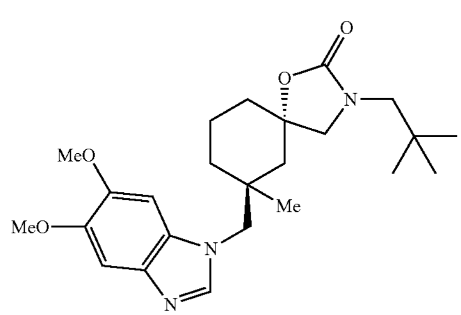 [SMILES: COc1cc2ncn(C[C@@]3(C)CCC[C@@]4(CN(CC(C)(C)C)C(=O)O4)C3)c2cc1OC] | 430.4 (M + H$^+$) |

-continued

| Ex | Name | Structure | MS (m/z) |
|---|---|---|---|
| 22 | 7-((5,6-dimethyl-1H-benzo[d]imidazol-1-yl)methyl)-7-methyl-3-neopentyl-1-oxa-3-azaspiro[4.5]decan-2-one | 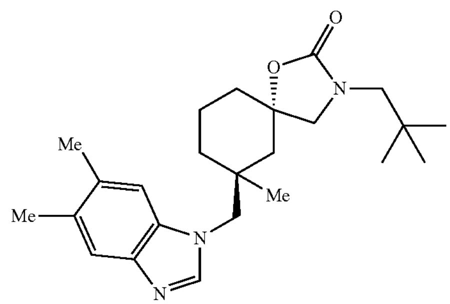 [SMILES: Cc1cc2ncn(C[C@@]3(C)CCC[C@@]4(CN(CC(C)(C)C)C(=O)O4)C3)c2cc1C] | 398.3 (M + H⁺) |

Example 23

3-neopentyl-7-((6-(trifluoromethyl)-1H-benzo[d]imidazol-1-yl)methyl)-1-oxa-3-azaspiro[4.5]decan-2-one

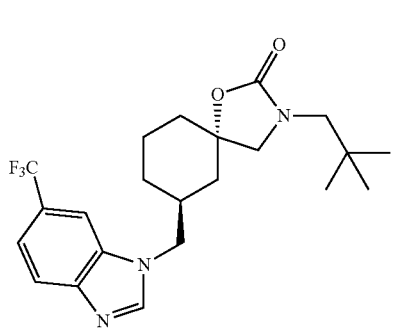 [SMILES: CC(C)(C)CN1C[C@@]2(CCC[C@H](Cn3cnc4ccc(C(F)(F)F)cc43)C2)OC1=O]

Intermediate 15

7-(bromomethyl)-3-neopentyl-1-oxa-3-azaspiro[4.5]decan-2-one

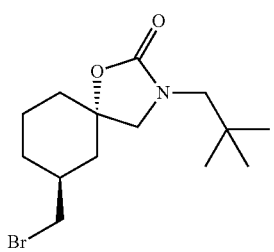 [SMILES: CC(C)(C)CN1C[C@@]2(CCC[C@H](CBr)C2)OC1=O]

Intermediate 15 was synthesized from Intermediate 8 using an analogous synthetic sequence as that used for the synthesis of Intermediate 11. MS (m/z) 318.1 (M⁺).

Intermediate 16

3-neopentyl-7-(((2-nitro-5-(trifluoromethyl)phenyl)amino)methyl)-1-oxa-3-azaspiro[4.5]decan-2-one

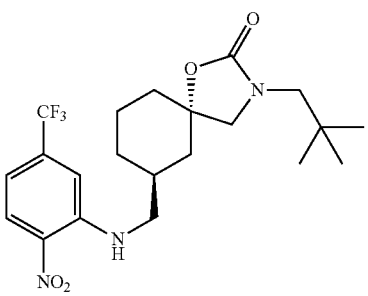 [SMILES: CC(C)(C)CN1C[C@@]2(CCC[C@H](CNc3cc(C(F)(F)F)ccc3[N+](=O)[O-])C2)OC1=O]

A solution containing 2-nitro-5-(trifluoromethyl)aniline (0.777 g, 3.77 mmol) and 7-(bromomethyl)-3-neopentyl-1-oxa-3-azaspiro[4.5]decan-2-one (1.00 g, 3.14 mmol) in DMF (15 mL) was treated with cesium carbonate (3.07 g, 9.43 mmol) and stirred at 60° C. overnight. The cooled reaction mixture was diluted with saturated, aqueous ammonium chloride solution, and the product was extracted into DCM. The organics were washed with brine, dried over Na₂SO₄, and concentrated. The residue was purified on a 120 g silica gel column (10-60 EtOAc/hexanes; 65 mL/min elution; 254 nm detection) to afford the title compound (0.260 g, 19 yield). MS (m/z) 444.2 (M+H⁺).

3-neopentyl-7-((6-(trifluoromethyl)-1H-benzo[d]imidazol-1-yl)methyl)-1-oxa-3-azaspiro[4.5]decan-2-one A solution of 3-neopentyl-7-(((2-nitro-5-(trifluoromethyl)phenyl)amino)methyl)-1-oxa-3-azaspiro[4.5]decan-2-one (0.260 g, 0.586 mmol) in MeOH (50 mL) was hydrogenated via a H-Cube® hydrogenation reactor (1 mL/min, 25° C., 10 bar H₂ pressure) with a 100 mm Pd/C cartridge. The reaction was monitored by LCMS and concentrated upon disappearance of starting material to afford 0.190 g of crude diamine. The crude diamine was dissolved in trimethylorthoformate (5.0 mL, 45.7 mmol) and formic acid (0.018 mL, 0.460 mmol), and the resulting mixture was stirred at rt for 3 h. The reaction was concentrated, and the crude material was partitioned between DCM and saturated sodium bicarbonate solution. The layers were separated, and the aqueous layer was washed with DCM. The combined organics were washed with brine, dried over $Na_2SO_4$, filtered, and concentrated. The crude product was purified using reverse-phase HPLC (Sunfire Prep C18 column (30×150 mm); 16 minute run; 50 mL/min flow rate with at-column dilution; Solvent A: MeCN/0.1% TFA, Solvent B: water/0.1% TFA, gradient: 20-60% solvent A) to afford the title compound (0.136 g, 52% yield) as the TFA salt. $^1$H NMR (500 MHz, DMSO-$d_6$) δ 8.68 (s, 1H), 8.23 (s, 1H), 7.89 (d, J=8.55 Hz, 1H), 7.58 (d, J=8.30 Hz, 1H), 4.31 (d, J=6.84 Hz, 2H), 3.31 (dd, J=9.03, 27.34 Hz, 2H), 2.86 (d, J=1.71 Hz, 2H), 2.11-2.23 (m, 1H), 1.80 (d, J=13.67 Hz, 2H), 1.61 (br. S., 1H), 1.54 (d, J=12.70 Hz, 1H), 1.45 (br. s., 2H), 1.34 (t, J=13.06 Hz, 1H), 1.03 (d, J=12.21 Hz, 1H), 0.83 (s, 9H). MS (m/z) 424.3 (M+H$^+$).

Example 24

2-ethyl-1-((7-methyl-3-neopentyl-2-oxo-1-oxa-3-azaspiro[4.5]decan-7-yl)methyl)-1H-benzo[d]imidazole-6-carbonitrile

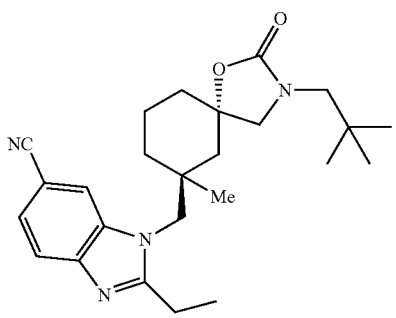 [SMILES: CCc1nc2ccc(C#N)cc2n1C[C@@]1(C)CCC[C@@]2(CN(CC(C)(C)C)C(=O)O2)C1]

Intermediate 17

3-(((7-methyl-3-neopentyl-2-oxo-1-oxa-3-azaspiro[4.5]decan-7-yl)methyl)amino)-4-nitrobenzonitrile

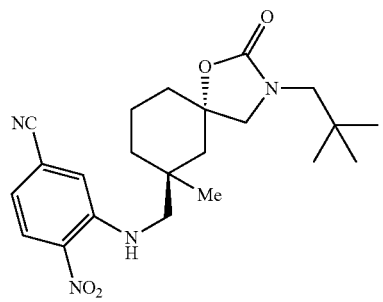 [SMILES: CC(C)(C)CN1C[C@@]2(CCC[C@](C)(CNc3cc(C#N)ccc3[N+](=O)[O-])C2)OC1=O]

To a yellow solution containing Intermediate 13 (0.500 g, 1.86 mmol) and 3-fluoro-4-nitrobenzonitrile (0.309 g, 1.86 mmol) in MeCN (12.4 mL) was added potassium carbonate (0.386 g, 2.79 mmol). The reaction mixture was stirred at rt for 18 h. The reaction was filtered through a frit. The filtrate was concentrated and purified on a 12 g silica gel column (5-30% EtOAc/hexanes, 30 min gradient; 30% EtOAc/hexanes, 5 min; 30 mL/min elution; 254 nm detection) to afford the title compound (0.690 g, 85% yield) as an orange oil. MS (m/z) 415.1 (M+H$^+$).

2-ethyl-1-((7-methyl-3-neopentyl-2-oxo-1-oxa-3-azaspiro[4.5]decan-7-yl)methyl)-1H-benzo[d]imidazole-6-carbonitrile To an orange solution containing 3-(((7-methyl-3-neopentyl-2-oxo-1-oxa-3-azaspiro[4.5]decan-7-yl)methyl)amino)-4-nitrobenzonitrile (0.100 g, 0.241 mmol) in 1-propanol (2.41 mL) was added iron (325 mesh) (0.135 g, 2.41 mmol), trimethyl orthopropionate (0.324 g, 2.41 mmol), and propionic acid (0.179 g, 2.41 mmol). The reaction mixture was stirred at 65° C. for 2 h and then cooled to rt. The reaction was diluted with MeCN (2 mL) and filtered through an Acrodisc CR 25 mm syringe filter with a 0.2 µm PTFE membrane. The filtered solution was purified by reverse-phase HPLC (Sunfire Prep C18 (30×150 mm); Solvent A: MeCN/0.1% TFA, Solvent B: water/0.1% TFA; gradient: 25-55% solvent A over 15 min; 25 mL/min elution; 220 nm detection) to afford the title compound (0.092 g, 69% yield) as the TFA salt. $^1$H NMR (400 MHz, CDCl$_3$) δ 8.07 (br. s., 1H), 7.83 (s, 1H), 7.69-7.79 (m, 1H), 4.08 (s, 2H), 3.32 (dd, J=8.78, 35.39 Hz, 2H), 3.01 (dd, J=14.05, 43.42 Hz, 2H), 2.05 (d, J=13.55 Hz, 1H), 1.85-1.99 (m, J=12.55 Hz, 2H), 1.48-1.77 (m, 5H), 1.20-1.44 (m, 8H), 0.96 (s, 9H). MS (m/z) 423.3 (M+H$^+$).

Example 25

5-chloro-1-((3-(2,2-dimethylpropyl)-2-oxo-1-oxa-3-azaspiro[4.5]dec-7-yl)methyl)-1H-benzimidazole-6-carbonitrile

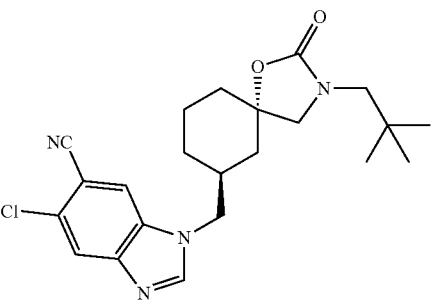 [SMILES: CC(C)(C)CN1C[C@@]2(CCC[C@H](Cn3cnc4cc(Cl)c(C#N)cc43)C2)OC1=O]

Intermediate 18

7-(aminomethyl)-3-neopentyl-1-oxa-3-azaspiro[4.5]decan-2-one

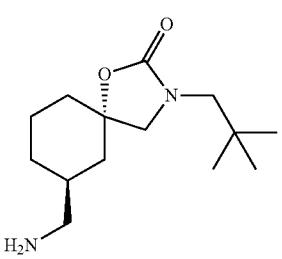 [SMILES: CC(C)(C)CN1C[C@@]2(CCC[C@H](CN)C2)OC1=O]

Intermediate 18 was synthesized from Intermediate 5 using the same synthetic sequence as outlined for the synthesis of Intermediate 13 without the ester enolate alkylation step outlined in the synthesis of Intermediate 9. ¹H NMR (400 MHz, CDCl₃) δ 3.35 (s, 2H), 3.01 (d, J=1.25 Hz, 2H), 2.60 (d, J=5.77 Hz, 2H), 2.06 (d, J=13.6 Hz, 1H), 2.00 (d, J=15.5 Hz, 1H), 1.60-1.94 (m, 5H), 1.37 (td, J=4.89, 13.36 Hz, 1H), 1.14 (t, J=12.80 Hz, 1H), 0.97 (s, 9H).

Intermediate 19

7-(((5-bromo-4-chloro-2-nitrophenyl)amino)methyl)-3-neopentyl-1-oxa-3-azaspiro[4.5]decan-2-one

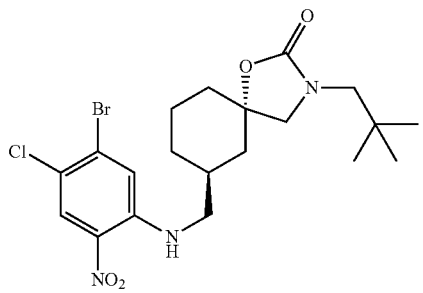 [SMILES: CC(C)(C)CN1C[C@@]2(CCC[C@H](CNc3cc(Br)c(Cl)cc3[N+](=O)[O-])C2)OC1=O]

A rt suspension of 1-bromo-2-chloro-5-fluoro-4-nitrobenzene (0.600 g, 2.36 mmol) in MeCN (8 mL) was treated with 7-(aminomethyl)-3-neopentyl-1-oxa-3-azaspiro[4.5]decan-2-one (0.400 g, 1.57 mmol) and potassium carbonate (0.543 g, 3.93 mmol). The reaction was stirred for 18 h, and the solids were filtered off and washed with EtOAc. The filtrate was concentrated and purified on a 40 g silica gel column (0-100% DCM/hexanes, 20 min gradient; 100% DCM, 15 min; 40 mL/min elution; 254 nm detection) to provide the title compound (0.340 g, 44% yield) as an orange solid. MS (m/z) 488.1, 490.1 (M+H⁺).

Intermediate 20

2-chloro-5-(((3-neopentyl-2-oxo-1-oxa-3-azaspiro[4.5]decan-7-yl)methyl)amino)-4-nitrobenzonitrile

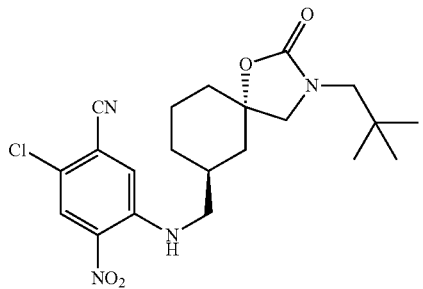 [SMILES: CC(C)(C)CN1C[C@@]2(CCC[C@H](CNc3cc(C#N)c(Cl)cc3[N+](=O)[O-])C2)OC1=O]

A suspension containing 7-(((5-bromo-4-chloro-2-nitrophenyl)amino)methyl)-3-neopentyl-1-oxa-3-azaspiro[4.5]decan-2-one (0.260 g, 0.532 mmol) and copper (I) cyanide (0.333 g, 3.72 mmol) in DMF (2 mL) was subject to microwave heating at 180° C. for 1.5 h. The reaction was cooled to rt, diluted with brine solution, and stirred for 20 min. The mixture was filtered through a pad of celite, and the celite was washed with EtOAc. The combined filtrates were washed with EtOAc. The combined organics were washed with water, dried over magnesium sulfate, filtered, and concentrated. The crude product was purified on a 24 g silica gel column (0-75% EtOAc/hexanes, 15 min gradient; 75% EtOAc/hexanes, 10 min; 35 mL/min elution; 254 nm detection) to afford the title compound as an orange solid. MS (m/z) 435.2 (M+H⁺).

5-chloro-1-((3-(2,2-dimethylpropyl)-2-oxo-1-oxa-3-azaspiro[4.5]dec-7-yl)methyl)-1H-benzimidazole-6-carbonitrile A suspension of 2-chloro-5-(((3-neopentyl-2-oxo-1-oxa-3-azaspiro[4.5]decan-7-yl)methyl)amino)-4-nitrobenzonitrile (0.236 g, 0.543 mmol), iron (325 mesh) (0.152 g, 2.71 mmol), and ammonium chloride (0.015 g, 0.271 mmol) in EtOH (3 mL) and water (0.5 mL) was stirred at 75° C. for 45 min. The reaction was cooled to rt and filtered through a pad of celite. The celite was washed with EtOAc, and the combined filtrates were partitioned between EtOAc and saturated sodium bicarbonate solution and 1 N NaOH (1:1). The organic layer was dried over Na₂SO₄, filtered, and concentrated to a purple foam. This residue was dissolved in formic acid (0.060 mL, 1.56 mmol) and trimethyl orthoformate (1.72 mL, 15.6 mmol). The resulting solution was stirred at rt for 18 h. The reaction mixture was concentrated and redissolved in EtOAc. The organic solution was washed with saturated sodium bicarbonate solution and concentrated. The crude product was purified using reverse-phase HPLC (Sunfire Prep C18 column (30×150 mm); 16 minute run; 50 mL/min flow rate with at-column dilution; Solvent A: MeCN/0.1% TFA, Solvent B: water/0.1% TFA, gradient: 30-70% solvent A) to afford the title compound (0.125 g, 57% yield) as the TFA salt. ¹H NMR (400 MHz, CDCl₃) δ 8.05 (s, 1H), 7.93 (s, 1H), 7.74 (s, 1H), 4.07 (ddd, J=7.53, 14.56, 24.85 Hz, 2H), 3.36 (dd, J=8.53, 24.09 Hz, 2H), 3.00 (dd, J=14.31, 32.37 Hz, 2H), 2.37-2.52 (m, 1H), 2.03 (d, J=16.81 Hz, 1H), 1.94 (dd, J=2.01, 12.80 Hz, 1H), 1.64-1.82 (m, 3H), 1.31-1.44 (m, 1H), 1.22 (t, J=12.80 Hz, 1H), 0.98-1.11 (m, 1H), 0.95 (s, 9H). MS (m/z) 415.2 (M+H⁺).

The following compounds were prepared using Intermediate 15 and the requisite substituted benzimidazole according to procedures analogous to that described for the conversion of Intermediate 15 to Example 25. As is appreciated by those skilled in the art, these analogous examples may involve variations in general reaction conditions.

| Ex | Name | Structure | MS (m/z) |
|---|---|---|---|
| 26 | 4-chloro-1-((-3-((4-methyltetrahydro-2H-pyran-4-yl)methyl)-2-oxo-1-oxa-3-azaspiro[4.5]decan-7-yl)methyl)-1H-benzo[d]imidazole-6-carbonitrile | 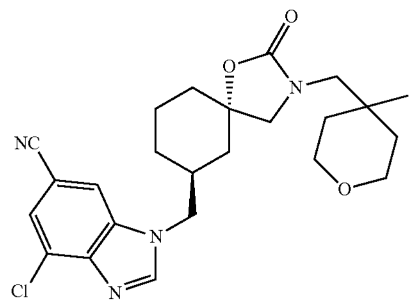 [SMILES: CC1(CN2C[C@@]3(CCC[C@H](Cn4cnc5c(Cl)cc(C#N)cc54)C3)OC2=O)CCOCC1] | 459.2 (M + H$^+$) |
| 27 | 1-((-3-((4-ethyltetrahydro-2H-pyran-4-yl)methyl)-2-oxo-1-oxa-3-azaspiro[4.5]decan-7-yl)methyl)-1H-benzo[d]imidazole-6-carbonitrile | 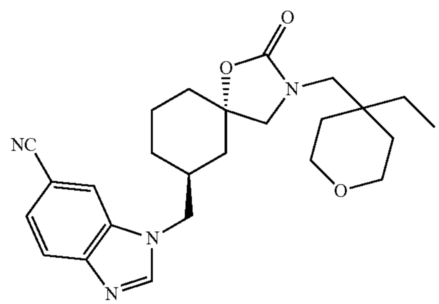 [SMILES: CCC1(CN2C[C@@]3(CCC[C@H](Cn4cnc5ccc(C#N)cc54)C3)OC2=O)CCOCC1] | 437.3 (M + H$^+$) |
| 28 | 1-((-3-(2-methylbutyl)-2-oxo-1-oxa-3-azaspiro[4.5]decan-7-yl)methyl)-1H-benzo[d]imidazole-6-carbonitrile | 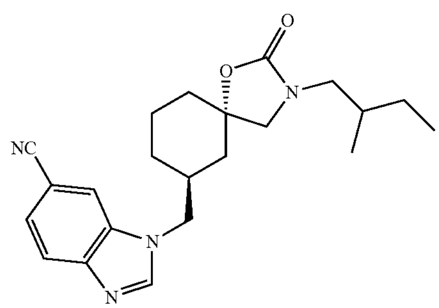 [SMILES: CCC(C)CN1C[C@@]2(CCC[C@H](Cn3cnc4ccc(C#N)cc43)C2)OC1=O] | 381.3 (M + H$^+$) |
| 29 | 5-fluoro-1-((-3-neopentyl-2-oxo-1-oxa-3-azaspiro[4.5]decan-7-yl)methyl)-1H-benzo[d]imidazole-6-carbonitrile | 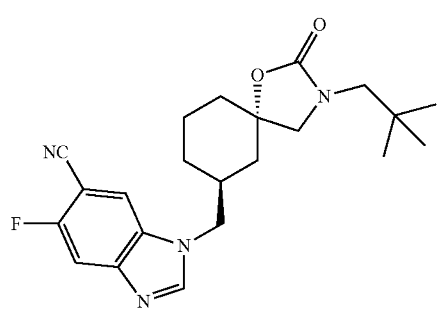 [SMILES: CC(C)(C)CN1C[C@@]2(CCC[C@H](Cn3cnc4cc(F)c(C#N)cc43)C2)OC1=O] | 399.2 (M + H$^+$) |
| 30 | 4-fluoro-1-((-3-neopentyl-2-oxo-1-oxa-3-azaspiro[4.5]decan-7-yl)methyl)-1H-benzo[d]imidazole-6-carbonitrile | 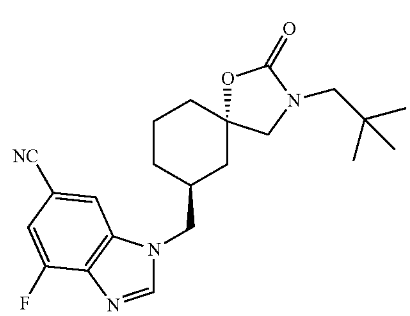 [SMILES: CC(C)(C)CN1C[C@@]2(CCC[C@H](Cn3cnc4c(F)cc(C#N)cc43)C2)OC1=O] | 399.2 (M + H$^+$) |

Example 31

4-chloro-1-((7-methyl-3-neopentyl-2-oxo-1-oxa-3-azaspiro[4.5]decan-7-yl)methyl)-1H-benzo[d]imidazole-6-carbonitrile

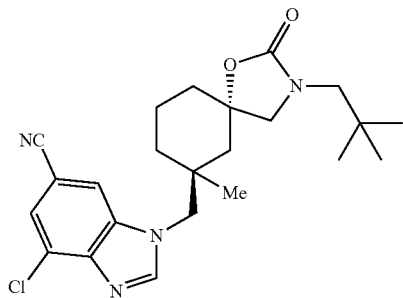 [SMILES: CC(C)(C)CN1C[C@@]2(CCC[C@](C)(Cn3cnc4c(Cl)cc(C#N)cc43)C2)OC1=O]

Intermediate 21

3-chloro-5-fluoro-4-nitrobenzonitrile

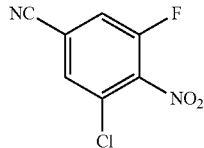 [SMILES: N#Cc1cc(F)c([N+](=O)[O-])c(Cl)c1]

Sodium perborate tetrahydrate (131 g, 851 mmol) in acetic acid (200 mL) was heated to 60° C. A solution of 4-amino-3-chloro-5-fluorobenzonitrile (29.0 g, 170 mmol) in acetic acid (500 mL) was added dropwise, and the resulting reaction was stirred at 60° C. for 18 h. LCMS analysis indicated ~50% conversion. Additional sodium perborate tetrahydrate (14.4 g, 93.6 mmol) was added, and the reaction was stirred at 70° C. for 2 h followed by another addition of sodium perborate tetrahydrate (70.0 g, 455 mmol). The reaction was stirred at 80° C. for 5 h and then at rt for 2 d. The reaction was poured into ice water, and the product was extracted into EtOAc. The combined organics were washed with water and brine. Finally, the organics were dried over MgSO$_4$, filtered, and concentrated to half volume. Addition of water resulted in precipitation of the desired product which was collected in a frit, washed with water, and dried in vacuo to provide an orange solid (27.5 g, 81% crude yield). $^1$H NMR (400 MHz, CDCl$_3$) δ 7.68 (s, 1H), 7.55 (d, 1H).

Intermediate 22

3-chloro-5-(((7-methyl-3-neopentyl-2-oxo-1-oxa-3-azaspiro[4.5]decan-7-yl)methyl)amino)-4-nitrobenzonitrile

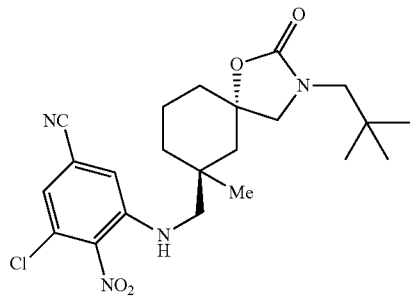 [SMILES: CC(C)(C)CN1C[C@@]2(CCC[C@](C)(CNc3cc(C#N)cc(Cl)c3[N+](=O)[O-])C2)OC1=O]

To a rt solution containing Intermediate 13 (0.100 g, 0.373 mmol) and 3-chloro-5-fluoro-4-nitrobenzonitrile (0.090 g, 0.447 mmol) in MeCN (4.97 mL) was added potassium carbonate (0.103 g, 0.745 mmol). After stirring for 17 h, the reaction was treated with additional 3-chloro-5-fluoro-4-nitrobenzonitrile (0.030 g, 0.149 mmol) and stirred at rt for 4 h. The reaction mixture was filtered through a frit, and the filtrate was concentrated onto florisil for purification on a 12 g silica gel column (0-30% EtOAc/hexanes, 30 min gradient; 30% EtOAc/hexanes, 5 min; 30 mL/min elution; 254 nm detection) to afford the title compound (0.137 g, 78% yield) as an orange solid. MS (m/z) 449.1 (M+H$^+$).

4-chloro-1-((7-methyl-3-neopentyl-2-oxo-1-oxa-3-azaspiro[4.5]decan-7-yl)methyl)-1H-benzo[d]imidazole-6-carbonitrile To an orange suspension containing 3-chloro-5-(((7-methyl-3-neopentyl-2-oxo-1-oxa-3-azaspiro[4.5]decan-7-yl)methyl)amino)-4-nitrobenzonitrile (0.132 g, 0.294 mmol) in MeOH (5.44 mL) was added iron (325 mesh) (0.164 g, 2.94 mmol), trimethyl orthoformate (0.325 mL, 2.94 mmol), and formic acid (0.113 mL, 2.94 mmol). The resulting solution was stirred at 65° C. for 26 h. Additional trimethyl orthoformate (0.325 mL, 2.94 mmol) and formic acid (0.113 mL, 2.94 mmol) was added, and stirring was continued at 65° C. for 24 h. The reaction was cooled to rt and concentrated. The resulting residue was suspended in MeCN (2 mL) and DMSO (4 mL) and filtered through a Hirsch funnel to remove any remaining solids. The filtrate was purified using reverse-phase HPLC (Sunfire Prep C18 column (30×150 mm); 14 minute run; 25 mL/min flow rate with at-column dilution; Solvent A: MeCN/0.1% TFA, Solvent B: water/0.1% TFA, gradient: 40-90% solvent A) to provide the title compound (0.101 g, 62% yield) as a TFA salt. $^1$H NMR (400 MHz, DMSO-d$_6$) δ 8.55 (s, 1H), 8.41 (d, J=1.25 Hz, 1H), 7.81 (d, J=1.25 Hz, 1H), 4.15 (s, 2H), 3.29 (dd, J=9.03, 20.33 Hz, 2H), 2.87 (s, 2H), 1.80 (d, J=13.55 Hz, 1H), 1.49-1.74 (m, 4H), 1.22-1.48 (m, 3H), 1.02 (s, 3H), 0.85 (s, 9H). MS (m/z) 429.2 (M+H$^+$).

Example 32

1-((7-ethyl-3-neopentyl-2-oxo-1-oxa-3-azaspiro[4.5]decan-7-yl)methyl)-1H-benzo[d]imidazole-6-carbonitrile

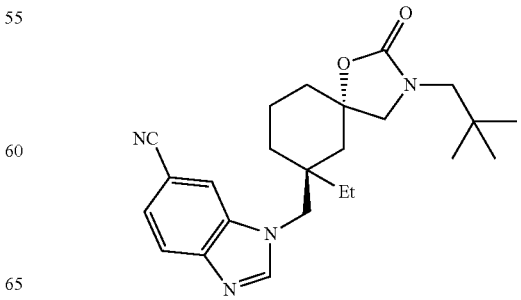

Intermediate 23

7-(aminomethyl)-7-ethyl-3-neopentyl-1-oxa-3-azaspiro[4.5]decan-2-one

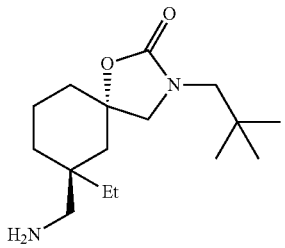

Intermediate 23 was synthesized from Intermediate 8 using the same synthetic sequence as outlined for the synthesis of Intermediate 13. The ester enolate alkylation required for Intermediate 23, highlighted previously in the synthesis of Intermediate 9, utilized iodoethane. NS (m/z) 283.3 (M+H$^+$).

Intermediate 24

3-(((7-ethyl-3-neopentyl-2-oxo-1-oxa-3-azaspiro[4.5]decan-7-yl)methyl)amino)-4-nitrobenzonitrile

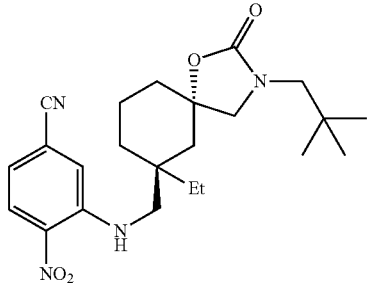 [SMILES: CC[C@]1(CNc2cc(C#N)ccc2[N+](=O)[O-])CCC[C@@]2(CN(CC(C)(C)C)C(=O)O2)C1]

To a yellow solution containing 7-(aminomethyl)-7-ethyl-3-neopentyl-1-oxa-3-azaspiro[4.5]decan-2-one (0.195 g, 0.690 mmol) and 3-fluoro-4-nitrobenzonitrile (0.126 g, 0.760 mmol) in MeCN (6.90 ml) was added potassium carbonate (0.191 g, 1.381 mmol). The reaction was stirred at rt for 16 h. The reaction was filtered through a frit, and the filtrate was concentrated onto florisil for purification on a 12 g silica gel column (5-25% EtOAc/hexanes, 30 min gradient; 25-55% EtOAc/hexanes, 5 min gradient; 30 mL/min elution; 254 nm detection) to afford the title compound (0.232 g, 75% yield) as an orange solid. MS (m/z) 429.2 (M+H$^+$).

1-((7-ethyl-3-neopentyl-2-oxo-1-oxa-3-azaspiro[4.5]decan-7-yl)methyl)-1H-benzo[d]imidazole-6-carbonitrile To an orange solution containing 3-(((7-ethyl-3-neopentyl-2-oxo-1-oxa-3-azaspiro[4.5]decan-7-yl)methyl)amino)-4-nitrobenzonitrile (0.125 g, 0.292 mmol) in MeOH (2.48 mL) was added iron (325 mesh) (0.163 g, 2.92 mmol), trimethyl orthoformate (0.322 mL, 2.92 mmol), and formic acid (0.112 mL, 2.92 mmol). The reaction mixture was stirred at 65° C. for 21 h. Additional trimethyl orthoformate ((0.322 mL, 2.92 mmol) and formic acid (0.112 mL, 2.92 mmol) were added, and the reaction was stirred at 65° C. for another 4 h. The reaction was cooled to rt, diluted with MeCN (2 mL), and filtered through a Acrodisc CR 25 mm syringe filter with 0.2 μm PTFE membrane. The filtered solution was purified by reverse-phase HPLC (Sunfire Prep C18 column (30×150 mm); 15 min run; 25 mL/min elution; Solvent A: MeCN/0.1% TFA, Solvent B: water/0.1% TFA, gradient: 30-60% solvent A) to afford the title compound (0.139 g, 88% yield) as the TFA salt. $^1$H NMR (400 MHz, CDCl$_3$) δ 8.65 (s, 1H), 8.06 (d, J=8.53 Hz, 1H), 7.85 (s, 1H), 7.73 (dd, J=1.25, 8.53 Hz, 1H), 4.13 (s, 2H), 3.31 (dd, J=8.78, 22.84 Hz, 2H), 3.00 (dd, J=14.31, 38.15 Hz, 2H), 2.01 (d, J=13.55 Hz, 2H), 1.81-1.97 (m, 2H), 1.58-1.75 (m, 3H), 1.10-1.29 (m, 3H), 1.06 (t, J=7.40 Hz, 3H), 0.96 (s, 9H); MS (m/z) 409.2 (M+H$^+$).

Example 33

1-{[3-(2,2-dimethylpropyl)-2-oxo-1-oxa-3-azaspiro[4.5]dec-7-yl]methyl}-1H-benzimidazole-6-carbonitrile-d2

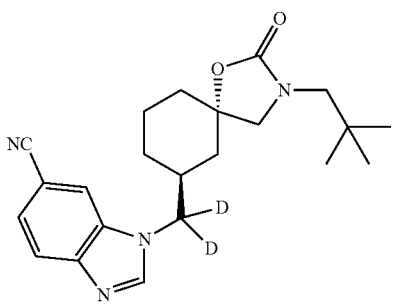 [SMILES: [2H]C([2H])([C@H]1CCC[C@]2(C1)CN(CC(C)(C)C)C(=O)O2)n1cnc2ccc(C#N)cc21]

Intermediate 25

3-(2,2-dimethylpropyl)-7-(hydroxymethyl)-1-oxa-3-azaspiro[4.5]decan-2-one-d2

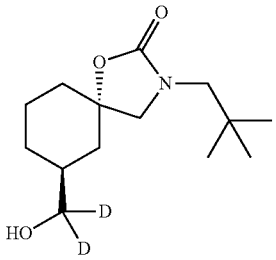 [SMILES: [2H]C([2H])(O)[C@H]1CCC[C@]2(C1)CN(CC(C)(C)C)C(=O)O2]

A −78° C. solution containing Intermediate 8 (1.00 g, 3.53 mmol) in THF (13.8 mL) was treated with lithium aluminium deuteride, 1 M in THF (3.88 mL, 3.88 mmol) dropwise. After stirring at −78° C. for 2 h, the reaction was quenched with 1 N HCl (30 mL) and diluted with EtOAc (30 mL). The layers were separated, and the aqueous layer was washed with EtOAc (30 mL). The combined organics were dried over Na$_2$SO$_4$, filtered, and concentrated onto florisil for purification on a 12 g silica gel column (5-35% EtOAc/hexanes, 30 min gradient; 35% EtOAc/hexanes, 5 min; 35-50% EtOAc/hexanes, 7 min gradient; 50-100% EtOAc/hexanes, 3 min gradient; 100% EtOAc, 5 min; 30 mL/min elution; 254 nm detection) to afford the title compound (0.350 g, 37% yield) as a white solid. $^1$H NMR (400 MHz, CDCl$_3$) δ 3.36 (s, 2H), 3.01 (d, J=2.26 Hz, 2H), 1.95-2.12 (m, 3H), 1.67-1.87 (m, 3H), 1.38 (td, J=4.89, 13.24 Hz, 1H), 1.23 (t, 1H), 0.98-1.07 (m, 1H), 0.97 (s, 9H); MS (m/z) 258.2 (M+H$^+$).

Intermediate 26

7-(aminomethyl)-3-(2,2-dimethylpropyl)-1-oxa-3-azaspiro[4.5]decan-2-one-d2

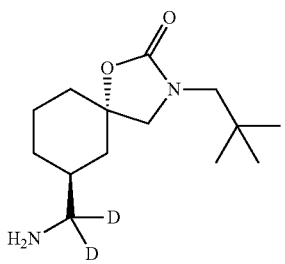 [SMILES: [2H]C([2H])(N)[C@H]1CCC[C@]2(C1)CN(CC(C)(C)C)C(=O)O2]

Intermediate 26 was synthesized from Intermediate 25 using the same synthetic sequence outlined for the conversion of Intermediate 10 to Intermediate 13 to provide the title compound (0.215 g, 75% yield) as an light yellow oil. $^1$H NMR (400 MHz, CDCl$_3$) δ 3.35 (s, 2H), 3.01 (d, J=2.01 Hz, 2H), 1.94-2.10 (m, 2H), 1.63-1.90 (m, 4H), 1.37 (td, J=5.02, 13.30 Hz, 1H), 1.14 (t, J=12.67 Hz, 1H), 0.97 (s, 9H), 0.91 (m, 1H); MS (m/z) 257.2 (M+H$^+$).

Intermediate 27

3-({[3-(2,2-dimethylpropyl)-2-oxo-1-oxa-3-azaspiro[4.5]dec-7-yl]methyl}amino)-4-nitrobenzonitrile-d2

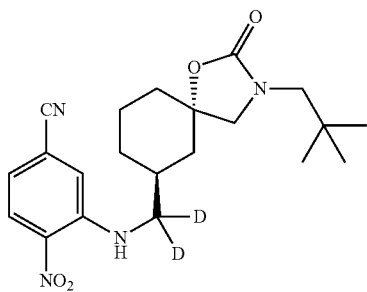 [SMILES: [2H]C([2H])(Nc1cc(C#N)ccc1[N+](=O)[O-])[C@H]1CCC[C@]2(C1)CN(CC(C)(C)C)C(=O)O2]

To a rt solution containing 7-(aminomethyl)-3-(2,2-dimethylpropyl)-1-oxa-3-azaspiro[4.5]decan-2-one-d2 (0.210 g, 0.819 mmol) and 3-fluoro-4-nitrobenzonitrile (0.136 g, 0.819 mmol) in MeCN (5.46 mL) was added potassium carbonate (0.226 g, 1.64 mmol). The reaction was stirred for 16 h. The reaction was quenched with water (15 mL), and the product was extracted into EtOAc (2×20 mL). The combined organics were dried over MgSO$_4$, filtered, and concentrated to provide the crude title compound (0.270 g, 78% crude yield). MS (m/z) 403.2 (M+H$^+$).

1-{[3-(2,2-dimethylpropyl)-2-oxo-1-oxa-3-azaspiro[4.5]dec-7-yl]methyl}-1H-benzimidazole-6-carbonitrile-d2

To an orange/black suspension containing 3-({[(5S,7S)-3-(2,2-dimethylpropyl)-2-oxo-1-oxa-3-azaspiro[4.5]dec-7-yl]methyl}amino)-4-nitrobenzonitrile-d2 (0.270 g, 0.671 mmol) and palladium on carbon, 10% (0.054 g, 0.507 mmol) in MeOH (5.71 mL) was added ammonium formate (0.423 g, 6.71 mmol). The reaction mixture was stirred at 65° C. After 30 min, trimethyl orthoformate (0.742 mL, 6.71 mmol) and formic acid (0.257 mL, 6.71 mmol) were added to the reaction mixture, and heating was continued for 1 h. The reaction was cooled to rt and filtered through celite. The celite was rinsed with EtOAc (3×10 mL), and the combined filtrates were concentrated. The crude solid was partitioned between EtOAc (15 mL) and saturated sodium bicarbonate solution (15 mL). The layers were separated, and the aqueous was washed with EtOAc (10 mL). The combined organics were dried over Na$_2$SO$_4$, filtered, and concentrated onto florisil for purification on a 4 g silica gel column (0-3% MeOH/DCM, 30 min gradient; 3-5% MeOH/DCM, 5 min gradient; 5% MeOH/DCM, 15 min; 18 mL/min elution; 254 nm detection) to provide the title compound (0.189 g, 70% yield). $^1$H NMR (400 MHz, CDCl$_3$) δ 8.04 (s, 1H), 7.89 (d, J=8.53 Hz, 1H), 7.74 (s, 1H), 7.56 (dd, J=1.51, 8.53 Hz, 1H), 3.35 (dd, J=8.53, 23.09 Hz, 2H), 2.99 (dd, J=14.05, 33.13 Hz, 2H), 2.39-2.51 (m, 1H), 1.92-2.07 (m, 2H), 1.66-1.82 (m, 3H), 1.37 (td, J=5.27, 13.05 Hz, 1H), 1.22 (t, J=12.80 Hz, 1H), 1.09 (m, 1H), 0.95 (s, 9H); MS (m/z) 383.2 (M+H$^+$).

Example 34

4-chloro-1-(((5S,7S)-3-neopentyl-2-oxo-1-oxa-3-azaspiro[4.5]decan-7-yl)methyl)-1H-benzo[d]imidazole-6-carbonitrile

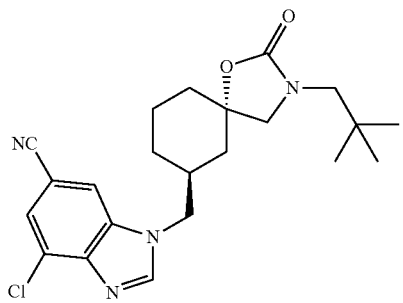 [SMILES: CC(C)(C)CN1C[C@@]2(CCC[C@H](Cn3cnc4c(Cl)cc(C#N)cc43)C2)OC1=O]

Intermediate 28

(S)-7-(nitromethyl)-1,4-dioxaspiro[4.5]decane

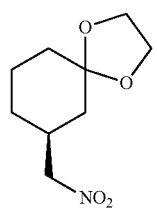 [SMILES: O=[N+]([O-])C[C@H]1CCCC2(C1)OCCO2]

(S)-3-(nitromethyl)cyclohexanone was synthesized according to the general procedure found in Mei, K.; et al *Org. Lett.* 2009, 11, 2864-2867. A rt solution containing (3S)-3-(nitromethyl)cyclohexanone (64.6 g, 411 mmol) and ethylene glycol (68.8 mL, 1233 mmol) in THF (741 mL) was treated with HCl (12.5 mL, 411 mmol) under nitrogen. After stirring for 18 h the reaction mixture was concentrated. The residue was dissolved in Et₂O and washed with water and saturated aqueous sodium bicarbonate. The combined aqueous layers were washed with Et₂O. The combined organics were washed with brine, dried over Na₂SO₄, filtered, and concentrated. The crude residue was purified on two 330 g silica gel columns (0-35% EtOAc/hexanes, 35 min gradient; 100 mL/min elution; 254 nm detection) to provide the title compound (27.7 g, 34% yield) as a yellow oil. ¹H NMR (400 MHz, CDCl₃) δ 4.29 (dd, J=7.03, 11.80 Hz, 2H), 3.94 (d, J=3.01 Hz, 4H), 2.44-2.57 (m, J=3.51, 7.26, 7.26, 11.18, 14.95 Hz, 1H), 1.68-1.83 (m, 4H), 1.54-1.68 (m, 1H), 1.42-1.53 (m, 1H), 1.34 (t, J=12.17 Hz, 1H), 1.09 (ddd, J=3.76, 12.80, 24.59 Hz, 1H). MS (m/z) 202.1 (M+H⁺).

Intermediate 29

(S)-1,4-dioxaspiro[4.5]decan-7-ylmethanamine

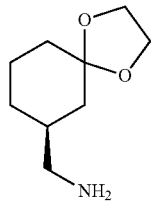 [SMILES: NC[C@H]1CCCC2(C1)OCCO2]

A solution of (S)-7-(nitromethyl)-1,4-dioxaspiro[4.5]decane (5.00 g, 24.9 mmol) in EtOH (150 mL) in a 1000 mL Parr bottle was flushed with nitrogen before Pd/C (1.32 g, 1.24 mmol) was added in one portion under nitrogen. The reaction flask was evacuated, charged with hydrogen (56 psi), and shaken for 19 h on the Parr shaker. The reaction mixture was filtered through celite under a stream of nitrogen, and the filtrate was concentrated to afford the crude title compound (4.37 g, 103% crude yield) which was used without further purification.

Intermediate 30

(S)-N-(1,4-dioxaspiro[4.5]decan-7-yl)methyl)-5-bromo-3-chloro-2-nitroaniline

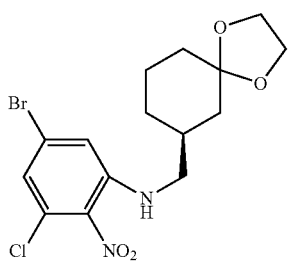 [SMILES: O=[N+]([O-])c1c(Cl)cc(Br)cc1NC[C@H]1CCCC2(C1)OCCO2]

To a rt solution containing (S)-1,4-dioxaspiro[4.5]decan-7-ylmethanamine (4.3 g, 25.1 mmol) in MeCN (100 mL) was added 5-bromo-1-chloro-3-fluoro-2-nitrobenzene (6.39 g, 25.1 mmol) and potassium carbonate (5.21 g, 37.7 mmol). After stirring for 21 h the reaction was filtered through a frit, and the filtrate was concentrated onto florisil for purification on a 120 g silica gel column (0-1% MeOH/DCM, 30 min gradient; 85 mL/min elution; 254 nm detection) to afford the title compound (8.48 g, 79% yield). MS (m/z) 405.0, 407.0 (M+H⁺).

Intermediate 31

(S)-3-((6-bromo-4-chloro-1H-benzo[d]imidazol-1-yl)methyl)cyclohexanone

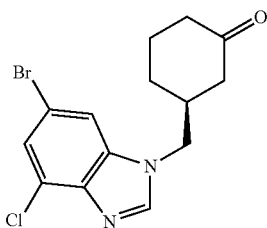 [SMILES: O=C1CCC[C@H](Cn2cnc3c(Cl)cc(Br)cc32)C1]

To an orange suspension containing (S)-N-(1,4-dioxaspiro [4.5]decan-7-yl)methyl)-5-bromo-3-chloro-2-nitroaniline (8.48 g, 20.9 mmol) in MeOH (142 mL) was added water (35.6 mL), iron (325 mesh) (5.84 g, 104 mmol), and ammonium chloride (0.559 g, 10.5 mmol). The suspension was stirred at 65° C. for 2 h. The reaction was cooled to rt and treated with trimethyl orthoformate (23.1 mL, 209 mmol) and formic acid (8.02 mL, 209 mmol). The resulting reaction mixture was stirred at rt for 19 h. Additional trimethyl orthoformate (23.1 mL, 209 mmol) and formic acid (8.02 mL, 209 mmol) were added. The reaction was stirred at rt for 23 h and then at 60° C. for 2 h. The reaction was treated with additional trimethyl orthoformate (11.6 mL, 105 mmol) and formic acid (4.01 mL, 402 mmol). Stirring was continued at 60° C. for 6 h at which time more trimethyl orthoformate (23.1 mL, 209 mmol) and formic acid (8.02 mL, 209 mmol) were added. The reaction was stirred at rt for 18 h and then filtered through celite. The celite was washed with EtOAc (3×100 mL), and the combined filtrates were concentrated. The crude material was partitioned between 2 N NaOH (250 mL) and EtOAc. The layers were separated, and the aqueous layer was washed with EtOAc (2×250 mL). The combined organics were dried over Na₂SO₄, filtered, and concentrated onto florisil for purification on a 120 g silica gel column (0-2% MeOH/DCM, 25 min gradient; 2-10% MeOH/DCM, 5 min gradient; 85 mL/min elution; 254 nm detection) to afford a 1:1 mixture of ketone title compound and ethylene glycol ketal (5.28 g, 74%) as a orange foam. This mixture was used without further purification. MS (m/z) 343.0 (ketone), 385.7 (ketal) (M+H⁺).

Intermediate 32

(S)-1-(1,4-dioxaspiro[4.5]decan-7-yl)methyl)-6-bromo-4-chloro-1H-benzo[d]imidazole

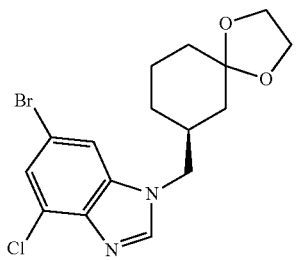 [SMILES: Clc1cc(Br)cc2c1ncn2C[C@H]1CCCC2(C1)OCCO2]

To a brown, rt solution containing a mixture of 6-bromo-4-chloro-1-[(7S)-1,4-dioxaspiro[4.5]dec-7-ylmethyl]-1H- benzimidazole (8.06 g, 20.90 mmol) and (3S)-3-[(6-bromo-4-chloro-1H-benzimidazol-1-yl)methyl]cyclohexanone (7.14 g, 20.90 mmol) in THF (135 ml) was added ethylene glycol (3.50 mL, 62.7 mmol) and HCl, 4 N in 1,4-dioxane (1.045 mL, 4.18 mmol). After stirring for 210 min, 2 N NaOH (200 mL) was added to the reaction, and the product was extracted into EtOAc (2×150 mL). The combined organics were dried over $Na_2SO_4$, filtered, and concentrated onto florisil for purification on a 120 g silica gel column (0-2.5% MeOH/DCM, 40 min gradient; 2.5% MeOH/DCM, 5 min; 85 mL/min elution; 254 nm detection) to provide the title compound 5.14 g, 61% yield) as an orange foam. MS (m/z) 385.0, 387.0 (M+H$^+$).

Intermediate 33

(S)-1-(1,4-dioxaspiro[4.5]decan-7-yl)methyl)-4-chloro-1H-benzo[d]imidazole-6-carbonitrile

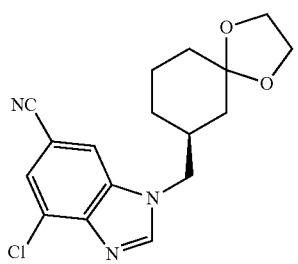 [SMILES: N#Cc1cc(Cl)c2ncn(C[C@H]3CCCC4(C3)OCCO4)c2c1]

To an orange solution of (S)-1-(1,4-dioxaspiro[4.5]decan-7-yl)methyl)-6-bromo-4-chloro-1H-benzo[d]imidazole (1.71 g, 4.43 mmol) in NMP (12.67 mL) was added copper(I) cyanide (1.99 g, 22.2 mmol). The reaction mixture was stirred at 180° C. in the microwave for 2 h. The reaction was cooled to rt and diluted with brine (200 mL). After stirring for 10 min the mixture was diluted with EtOAc (300 mL) and filtered through celite. The celite was washed with EtOAc (2×100 mL), and the combined filtrates were adjusted to pH 13 with 2 N NaOH. The layers were separated, and the aqueous was washed with EtOAc (200 mL). The combined organics were washed with water (3×400 mL), dried over $MgSO_4$, filtered, and concentrated to a dark orange oil which was used without purification. LCMS analysis indicates that the crude product is a mixture of the title compound and corresponding ketone. MS (m/z) 288.1 (ketone), 332.1 (title compound) (M+H$^+$).

Intermediate 34

(S)-4-chloro-1-((3-oxocyclohexyl)methyl)-1H-benzo[d]imidazole-6-carbonitrile

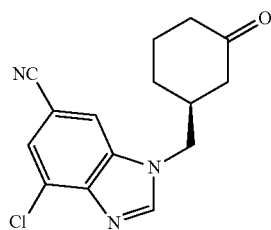 [SMILES: N#Cc1cc(Cl)c2ncn(C[C@H]3CCCC(=O)C3)c2c1]

To an orange solution containing a mixture of 4-chloro-1-[(7S)-1,4-dioxaspiro[4.5]dec-7-ylmethyl]-1H-benzimidazole-6-carbonitrile (4.41 g, 13.3 mmol) and 4-chloro-1-{[(1S)-3-oxocyclohexyl]methyl}-1H-benzimidazole-6-carbonitrile (3.83 g, 13.3 mmol) in acetone (46.6 ml) was added HCl, 2 N in water (20.0 mL, 39.9 mmol). The mixture was stirred at rt for 15 h and concentrated. The residue was suspended in 2 N NaOH and extracted into EtOAc (3×75 mL) while maintaining an aqueous pH of 13. The combined organic extracts were dried over $Na_2SO_4$, filtered, and concentrated onto florisil for purification on a 80 g silica gel column (0-5% MeOH/DCM, 35 min gradient; 5% MeOH/DCM, 5 min; 5-10% MeOH/DCM, 25 min gradient; 10% MeOH/DCM, 15 min; 60 mL/min elution; 254 nm detection) to afford the title compound and the analogous bromide (1.15 g, 27% yield, 2 steps) as an orange solid. MS (m/z) 288.1 (M+H$^+$).

Intermediate 35

1-((3S,5S)-1-oxaspiro[2,5]octan-5-ylmethyl)-4-chloro-1H-benzo[d]imidazole-6-carbonitrile

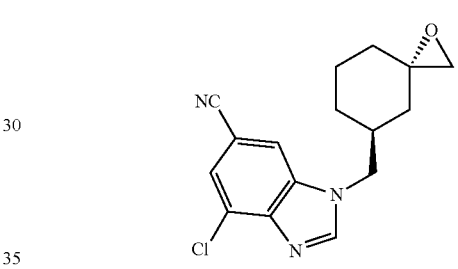

To a yellow solution of trimethylsulfoxonium iodide (1.31 g, 5.97 mmol) in DMSO (31.8 mL) under nitrogen at rt was added sodium hydride (0.239 g, 5.97 mmol). The color disappeared and bubbling occurred. Stirring was continued at rt for 30 min, and then a solution containing a mixture of 4-chloro-1-{[(1S)-3-oxocyclohexyl]methyl}-1H-benzimidazole-6-carbonitrile (1.15 g, 3.98 mmol) and (3S)-3-[(6-bromo-4-chloro-1H-benzimidazol-1-yl)methyl]cyclohexanone (1.36 g, 3.98 mmol) dissolved in DMSO (7.96 mL) was slowly added. After stirring 16 h, brine solution (25 mL) was added followed by 2 N NaOH (25 mL) to pH 13. The product was extracted into EtOAc (3×75 mL). The combined organics were washed with water (2×150 mL), dried over $Na_2SO_4$, filtered, and concentrated onto florisil for purification on a 12 g silica gel column (0-2% MeOH/DCM, 20 min gradient; 30 mL/min elution; 254 nm detection) to afford the title compound (0.735 g, 55% yield). MS (m/z) 302.1 (M+H$^+$).

4-chloro-1-(((5S,7S)-3-neopentyl-2-oxo-1-oxa-3-azaspiro[4.5]decan-7-yl)methyl)-1H-benzo[d]imidazole-6-carbonitrile To an orange solution of 1-((3S,5S)-1-oxaspiro[2.5]octan-5-yl)methyl)-4-chloro-1H-benzo[d]imidazole-6-carbonitrile (0.732 g, 2.18 mmol) in MeOH (14.6 mL) in a 20 mL microwave vial was added neopentylamine (0.571 g, 6.55 mmol). The microwave vial was tightly capped and heated at 110° C. behind a blast shield. After stirring for 18 h, the reaction was cooled to rt before the cap was safely removed and the reaction concentrated. The crude product was dissolved in 1,4-dioxane (14.6 mL), and the resulting solution was treated with CDI (1.77 g, 10.9 mmol). The reaction was stirred at 120° C. for 17 h. The reaction was cooled to rt and concentrated. The residue was dissolved in MeOH (25 mL) and the resulting solution was filtered through an Acrodisc CR 25 mm syringe filter with 0.2 µm PTFE membrane. The solution was purified by reverse-phase HPLC (Sunfire Prep C18 column (30×150 mm); 15 min run; 25 mL/min elution; Solvent A: MeCN/0.1% TFA, Solvent B: water/0.1% TFA, gradient: 30-70 solvent A) to afford the title compound with some impurities. The collected solids were loaded onto florisil and purified on a 40 g silica gel column (0-2% MeOH/DCM, 20 min gradient; 2% MeOH/DCM, 5 min; 40 mL/min elution; 254 nm detection) to provide the title compound (0.315 g, 33% yield) as a white foam. $^1$H NMR (400 MHz, CDCl$_3$) δ 8.09 (s, 1H), 7.67 (d, J=1.25 Hz, 1H), 7.60 (d, J=1.25 Hz, 1H), 4.09 (ddd, J=7.53, 14.56, 25.35 Hz, 2H), 3.36 (dd, J=8.53, 23.59 Hz, 2H), 3.00 (dd, J=14.05, 31.87 Hz, 2H), 2.38-2.53 (m, 1H), 2.01 (d, J=2.01, 14.05 Hz, 1H), 1.90-1.99 (m, J=10.79, 12.80 Hz, 1H), 1.64-1.81 (m, 3H), 1.31-1.43 (m, 1H), 1.21 (t, J=12.80 Hz, 1H), 0.98-1.10 (m, 1H), 0.95 (s, 9H); MS (m/z) 415.1 (M+H$^+$).

The following compounds were prepared using either racemic or optically-pure Intermediate 29 and the requisite substituted 2-fluoronitrobenzene according to procedures analogous to that described for the synthesis of Example 34. As is appreciated by those skilled in the art, these analogous examples may involve variations in general reaction conditions.

| Ex | Name | Structure | MS (m/z) |
|---|---|---|---|
| 35 | 4-bromo-1-((-3-neopentyl-2-oxo-1-oxa-3-azaspiro[4.5]decan-7-yl)methyl)-1H-benzo[d]imidazole-6-carbonitrile | 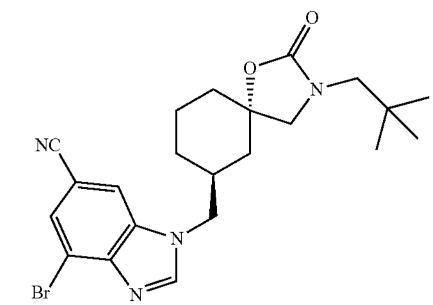 [SMILES: CC(C)(C)CN1C[C@@]2(CCC[C@H](Cn3cnc4c(Br)cc(C#N)cc43)C2)OC1=O] | 459.1, 460.1 (M + H$^+$) |
| 36 | 4-methoxy-1-((-3-neopentyl-2-oxo-1-oxa-3-azaspiro[4.5]decan-7-yl)methyl)-1H-benzo[d]imidazole-6-carbonitrile | 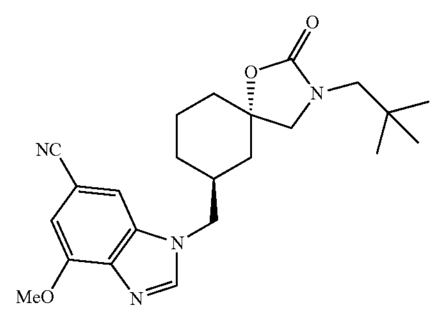 [SMILES: COc1cc(C#N)cc2c1ncn2C[C@H]1CCC[C@]2(C1)CN(CC(C)(C)C)C(=O)O2] | 411.2 (M + H$^+$) |
| 37 | 5-fluoro-1-((-3-((2-methyltetrahydrofuran-2-yl)methyl)-2-oxo-1-oxa-3-azaspiro[4.5]decan-7-yl)methyl)-1H-benzo[d]imidazole-6-carbonitrile | 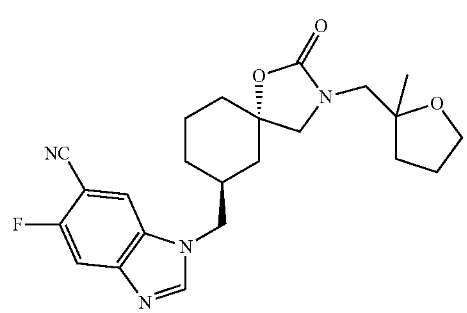 [SMILES: CC1(CN2C[C@@]3(CCC[C@H](Cn4cnc5cc(F)c(C#N)cc54)C3)OC2=O)CCCO1] | 427.3 (M + H$^+$) |

-continued

| Ex | Name | Structure | MS (m/z) |
|---|---|---|---|
| 38 | 5-fluoro-1-((-3-(3-methoxy-2,2-dimethylpropyl)-2-oxo-1-oxa-3-azaspiro[4.5]decan-7-yl)methyl)-1H-benzo[d]imidazole-6-carbonitrile | 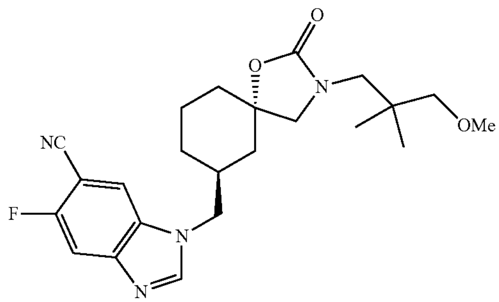 [SMILES: COCC(C)(C)CN1C[C@@]2(CCC[C@H](Cn3cnc4cc(F)c(C#N)cc43)C2)OC1=O] | 429.3 (M + H+) |
| 39 | 1-(((5S,7S)-3-((2-ethyltetrahydro-2H-pyran-2-yl)methyl)-2-oxo-1-oxa-3-azaspiro[4.5]decan-7-yl)methyl)-1H-benzo[d]imidazole-6-carbonitrile | 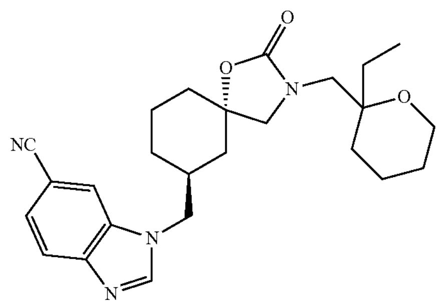 [SMILES: CCC1(CN2C[C@@]3(CCC[C@H](Cn4cnc5ccc(C#N)cc54)C3)OC2=O)CCCCO1] | 437.2 (M + H+) |
| 40 | 1-(((5S,7S)-3-(3-ethoxy-2,2-dimethylpropyl)-2-oxo-1-oxa-3-azaspiro[4.5]decan-7-yl)methyl)-1H-benzo[d]imidazole-6-carbonitrile | 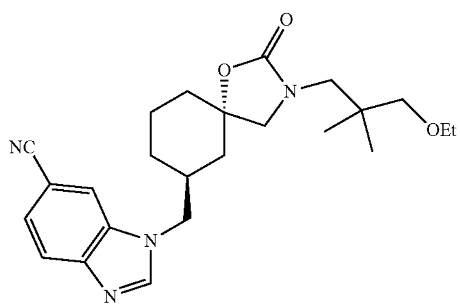 [SMILES: CCOCC(C)(C)CN1C[C@@]2(CCC[C@H](Cn3cnc4ccc(C#N)cc43)C2)OC1=O] | 425.2 (M + H+) |
| 41 | 4-chloro-1-(((5S,7S)-3-((2-methyltetrahydrofuran-2-yl)methyl)-2-oxo-1-oxa-3-azaspiro[4.5]decan-7-yl)methyl)-1H-benzo[d]imidazole-6-carbonitrile | 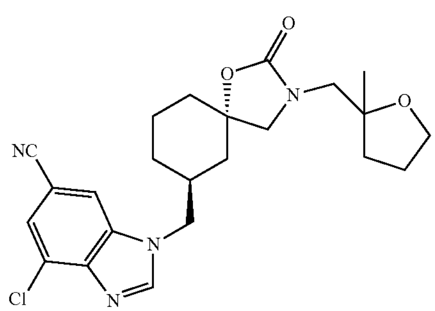 [SMILES: CC1(CN2C[C@@]3(CCC[C@H](Cn4cnc5c(Cl)cc(C#N)cc54)C3)OC2=O)CCCO1] | 443.2 (M + H+) |
| 42 | 7-((6-chloro-5-fluoro-1H-benzo[d]imidazol-1-yl)methyl)-3-((2-methyltetrahydrofuran-2-yl)methyl)-1-oxa-3-azaspiro[4.5]decan-2-one | 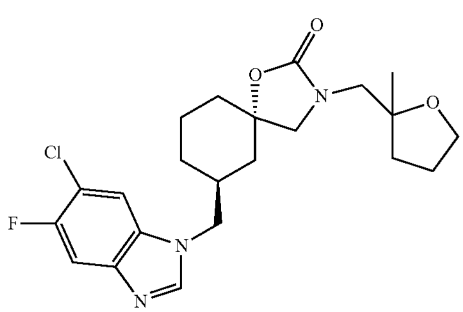 [SMILES: CC1(CN2C[C@@]3(CCC[C@H](Cn4cnc5cc(F)c(Cl)cc54)C3)OC2=O)CCCO1] | 436.1 (M + H+) |

-continued

| Ex | Name | Structure | MS (m/z) |
|---|---|---|---|
| 43 | 1-(((5S,7S)-2-oxo-3-((tetrahydro-2H-pyran-2-yl)methyl)-1-oxa-3-azaspiro[4.5]decan-7-yl)methyl)-1H-benzo[d]imidazole-6-carbonitrile | 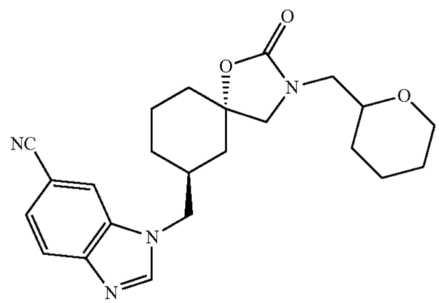 [SMILES: N#Cc1ccc2ncn(C[C@H]3CCC[C@]4(C3)CN(CC3CCCCO3)C(=O)O4)c2c1] | 409.1 (M + H$^+$) |
| 44 | 5-fluoro-1-((-3-((1-(methoxymethyl)cyclopropyl)methyl)-2-oxo-1-oxa-3-azaspiro[4.5]decan-7-yl)methyl)-1H-benzo[d]imidazole-6-carbonitrile | 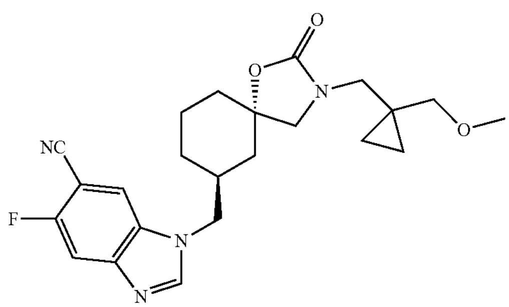 [SMILES: COCC1(CN2C[C@@]3(CCC[C@H](Cn4cnc5cc(F)c(C#N)cc54)C3)OC2=O)CC1] | 427.2 (M + H$^+$) |
| 45 | 1-(((5S,7S)-3-(3-methoxy-2,2-dimethylpropyl)-2-oxo-1-oxa-3-azaspiro[4.5]decan-7-yl)methyl)-1H-benzo[d]imidazole-6-carbonitrile | 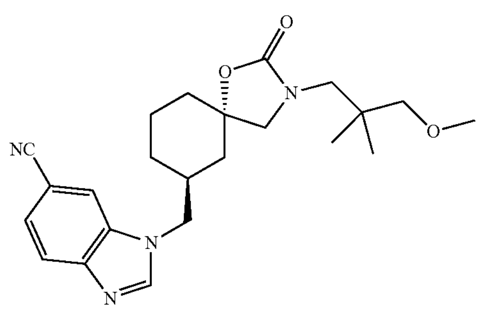 [SMILES: COCC(C)(C)CN1C[C@@]2(CCC[C@H](Cn3cnc4ccc(C#N)cc43)C2)OC1=O] | 411.2 (M + H$^+$) |
| 46 | 1-(((5S,7S)-3-((4-(methoxymethyl)tetrahydro-2H-pyran-4-yl)methyl)-2-oxo-1-oxa-3-azaspiro[4.5]decan-7-yl)methyl)-1H-benzo[d]imidazole-6-carbonitrile | 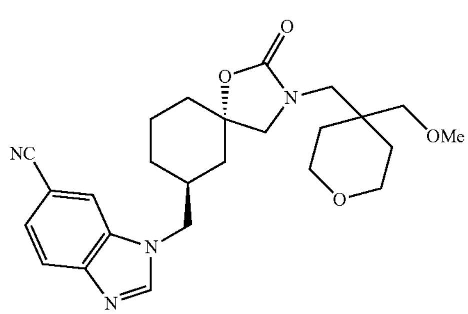 [SMILES: COCC1(CN2C[C@@]3(CCC[C@H](Cn4cnc5ccc(C#N)cc54)C3)OC2=O)CCOCC1] | 453.2 (M + H$^+$) |

| Ex | Name | Structure | MS (m/z) |
|---|---|---|---|
| 47 | (5S,7S)-3-(3-methoxy-2,2-dimethylpropyl)-7-((6-(trifluoromethyl)-1H-benzo[d]imidazol-1-yl)methyl)-1-oxa-3-azaspiro[4.5]decan-2-one | 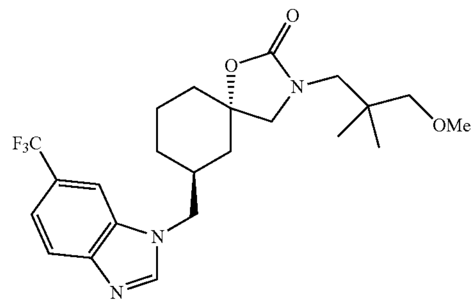 [SMILES: COCC(C)(C)CN1C[C@@]2(CCC[C@H](Cn3cnc4ccc(C(F)(F)F)cc43)C2)OC1=O] | 454.2 (M + H⁺) |
| 48 | 1-(((5S,7S)-2-oxo-3-(2,2,3,3,3-pentafluoropropyl)-1-oxa-3-azaspiro[4.5]decan-7-yl)methyl)-1H-benzo[d]imidazole-6-carbonitrile | 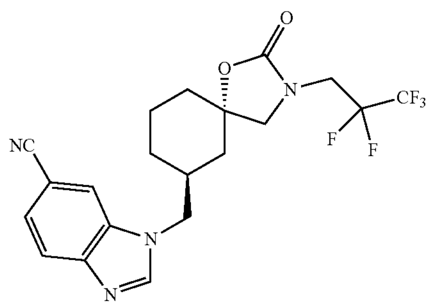 [SMILES: N#Cc1ccc2ncn(C[C@H]3CCC[C@]4(C3)CN(CC(F)(F)C(F)(F)F)C(=O)O4)c2c1] | 443.1 (M + H⁺) |
| 49 | 1-(((5S,7S)-3-(2-methoxy-2-methylpropyl)-2-oxo-1-oxa-3-azaspiro[4.5]decan-7-yl)methyl)-1H-benzo[d]imidazole-6 carbonitrile | 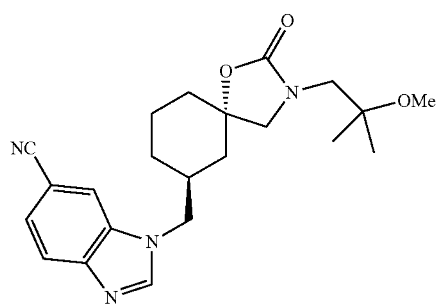 [SMILES: COC(C)(C)CN1C[C@@]2(CCC[C@H](Cn3cnc4ccc(C#N)cc43)C2)OC1=O] | 397.2 (M + H⁺) |
| 50 | 4-chloro-1-(((5S,7S)-2-oxo-3-(((S)-tetrahydrofuran-2-yl)methyl)-1-oxa-3-azaspiro[4.5]decan-7-yl)methyl)-1H-benzo[d]imidazole-6-carbonitrile | 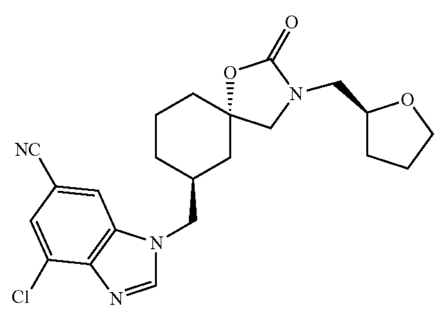 [SMILES: N#Cc1cc(Cl)c2ncn(C[C@H]3CCC[C@]4(C3)CN(C[C@@H]3CCCO3)C(=O)O4)c2c1] | 429.2 (M + H⁺) |
| 51 | 1-(((5S,7S)-3-((1-methylcyclobutyl)methyl)-2-oxo-1-oxa-3-azaspiro[4.5]decan-7-yl)methyl)-1H-benzo[d]imidazole-6-carbonitrile | 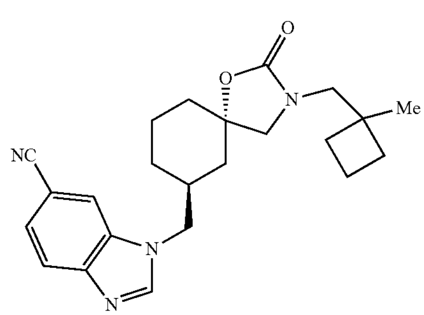 [SMILES: CC1(CN2C[C@@]3(CCC[C@H](Cn4cnc5ccc(C#N)cc54)C3)OC2=O)CCC1] | 393.2 (M + H⁺) |

| Ex | Name | Structure | MS (m/z) |
|---|---|---|---|
| 52 | 1-{[(5S,7S)-3-(2,2-dimethylpropyl)-2-oxo-1-oxa-3-azaspiro[4.5]dec-7-yl]methyl}-1H-benzimidazole-6-carbonitrile-d2 | 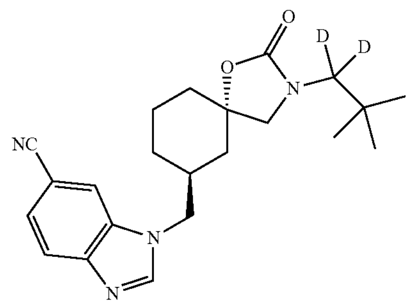 [SMILES: [2H]C([2H])(N1C[C@@]2(CCC[C@H](Cn3cnc4ccc(C#N)cc43)C2)OC1=O)C(C)(C)C] | 383.2 (M + H⁺) |
| 53 | 1-(((5S,7S)-3-(2,2-dimethylbutyl)-2-oxo-1-oxa-3-azaspiro[4.5]decan-7-yl)methyl)-1H-benzo[d]imidazole-6-carbonitrile | 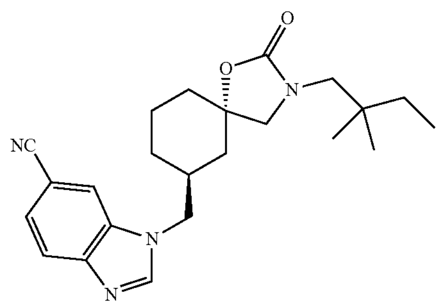 [SMILES: CCC(C)(C)CN1C[C@@]2(CCC[C@H](Cn3cnc4ccc(C#N)cc43)C2)OC1=O] | 395.2 (M + H⁺) |
| 54 | 1-(((5S,7S)-3-((S)-2-methylbutyl)-2-oxo-1-oxa-3-azaspiro[4.5]decan-7-yl)methyl)-1H-benzo[d]imidazole-6 carbonitrile | 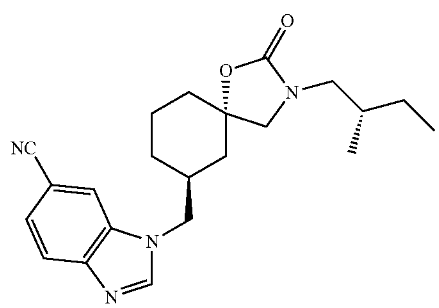 [SMILES: CC[C@H](C)CN1C[C@@]2(CCC[C@H](Cn3cnc4ccc(C#N)cc43)C2)OC1=O] | 381.2 (M + H⁺) |
| 55 | 1-(((5S,7S)-3-(cyclopentylmethyl)-2-oxo-1-oxa-3-azaspiro[4.5]decan-7-yl)methyl)-1H-benzo[d]imidazole-6-carbonitrile | 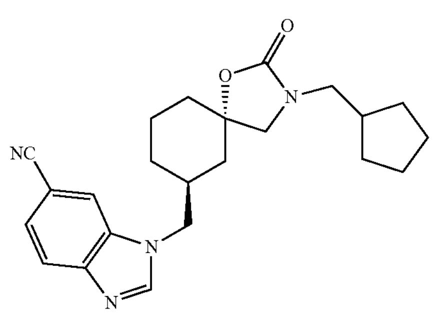 [SMILES: N#Cc1ccc2ncn(C[C@H]3CCC[C@]4(C3)CN(CC3CCCC3)C(=O)O4)c2c1] | 393.2 (M + H⁺) |

Example 56

4-methyl-1-((3-neopentyl-2-oxo-1-oxa-3-azaspiro[4.5]decan-7-yl)methyl)-1H-benzo[d]imidazole-6-carbonitrile

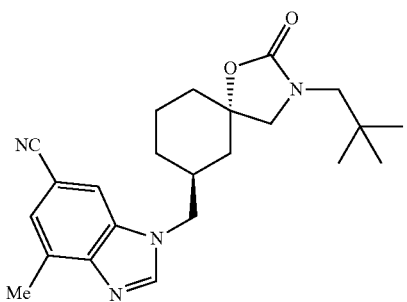 [SMILES: Cc1cc(C#N)cc2c1ncn2C[C@H]1CCC[C@]2(C1)CN(CC(C)(C)C)C(=O)O2]

4-bromo-1-((3-neopentyl-2-oxo-1-oxa-3-azaspiro[4.5]decan-7-yl)methyl)-1H-benzo[d]imidazole-6-carbonitrile (0.100 g, 0.218 mmol) was dissolved in THF (1.00 mL) and treated with tetrakis(triphenylphosphine)palladium(0) (0.503 g, 0.044 mmol) followed by dimethylzinc (1.09 mL, 2.18 mmol). Addition of the dimethylzinc resulted in an exotherm with gas evolution and a color change from brownish-yellow to bright yellow. The reaction mixture was purged with nitrogen and capped. The reaction was allowed to stir at rt for 18 h. The reaction mixture turned dark brown over the course of the reaction. The reaction was quenched with sat. aq. ammonium chloride solution and diluted with EtOAc. The layers were separated, and the organics were washed with brine, dried over MgSO$_4$, filtered, and concentrated. The crude product was purified by reverse-phase HPLC (Sunfire Prep C18 column (30×150 mm); 15 min run; 50 mL/min elution; Solvent A: MeCN/0.1% TFA, Solvent B: water/0.1% TFA, gradient: 35-69% solvent A) to afford the title compound (0.035 g, 31% yield) as the TFA salt. $^1$H NMR (400 MHz, DMSO-d$_6$) δ 8.55 (br. s., 1H), 8.19 (s, 1H), 7.44 (s, 1H), 4.21 (d, J=7.03 Hz, 2H), 3.31 (dd, J=8.78, 18.57 Hz, 2H), 2.85 (s, 2H), 2.56 (s, 3H), 2.06-2.21 (m, 1H), 1.81 (d, J=11.04 Hz, 1H), 1.73 (d, J=13.80 Hz, 1H), 1.40-1.58 (m, 4H), 1.25-1.35 (m, 1H), 0.95-1.08 (m, 1H), 0.83 (s, 9H). MS (m/z) 395.2 (M+H$^+$).

Example 57

1-{[(5S,7S)-7-methyl-3-(2-methylpropyl)-2-oxo-1-oxa-3-azaspiro[4.5]dec-7-yl]methyl}-1H-benzimidazole-6-carbonitrile

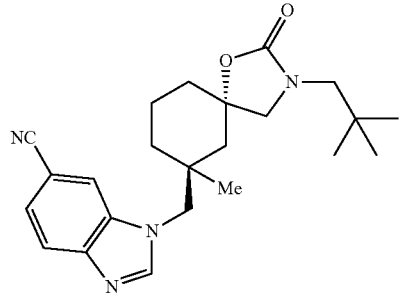 [SMILES: CC(C)(C)CN1C[C@@]2(CCC[C@](C)(Cn3cnc4ccc(C#N)cc43)C2)OC1=O]

Intermediate 3 (100 mg, 0.355 mmol) and isobutyl amine (130 mg, 1.777 mmol) was dissolved in methanol (4 mL) and heated at 120° C. for 4 h. The reaction was cooled to rt, concentrated, and codistilled with DCM to afford a colorless oil. The crude product was redissolved in 1,4-dioxane (4.00 mL) and carbonyldiimidazole (57.6 mg, 0.355 mg) was added. The reaction mixture was heated at 120° C. overnight. The crude reaction mixture was concentrated and the residue purified by reverse-phase HPLC (Sunfire Prep C18 column (30×150 mm); 16 min run; 50 mL/min flow rate with at-column dilution; Solvent A: MeCN/0.1% TFA, Solvent B: water/0.1% TFA, gradient: 20-60% solvent A) to yield the title compound (127 mg, 68.6% yield) as the TFA salt. $^1$H NMR (400 MHz, CDCl$_3$) 9.28 (s, 1H), 8.10 (d, J=8.0 Hz, 1H), 8.04 (s, 1H), 7.84 (dd, J=1.5, 8.5 Hz, 1H), 4.23 (s, 2H), 3.24-3.29 (m, 2H), 2.98-3.11 (m, 2H), 2.00-2.15 (m, 1H), 1.80-2.00 (m, 3H), 1.70-1.80 (m, 1H), 1.60-1.68 (m, 1H), 1.49 (d, J=8.0 Hz, 1H), 1.30-1.40 (m, 2H), 1.24 (s, 3H), 0.93 (s, 3H), 0.91 (s, 3H). MS (m/z) 381.0 (M+H$^+$).

The invention claimed is:
1. A compound of Formula (I):

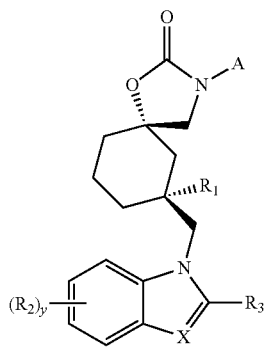

Wherein:
R$_1$ is hydrogen, C$_{1-3}$ alkyl, CH$_2$OH, CH$_2$—O—CH$_3$, CH$_2$OCH$_2$Ph, CH$_2$CN, CN, halo or C(O)OCH$_3$;
R$_2$ is independently hydrogen, CN, CF$_3$, halo, SO$_2$C$_{1-3}$ alkyl, C$_{1-3}$ alkyl or C≡CH;
R$_3$ is hydrogen, C$_{1-2}$ alkyl, CF$_3$ or —OH;
R$_4$ is hydrogen, halo or C$_{1-3}$ alkyl;
X is CR$_4$ or N;
A is C$_{1-6}$ alkyl unsubstituted or substituted by 1-5 substituents chosen from:
halo, C$_{1-3}$ alkyl, C$_{3-6}$ cycloalkyl, Si(CH$_3$)$_3$, CN, C≡CH, OC$_{1-3}$alkyl, SMe, CF$_3$, OCF$_3$, SCF$_3$, C(O)OR$_c$, C(O)(NR$_d$R$_e$), tetrahydrofuryl, tetrahydropyranyl, tetrahydropyrrolyl, or oxotetrahydropyrrolyl;
  wherein the tetrahydrofuryl and tetrahydropyranyl may be further substituted with one or two C$_{1-3}$ alkyl groups;
or A is C$_{5-6}$cycloalkyl substituted by one or more C$_{1-3}$alkyl groups;
or A is (CHR$_f$)$_n$—(CR$_a$R$_b$)—(CH$_2$)$_m$—R$_x$;
R$_a$ is hydrogen or C$_{1-3}$alkyl; wherein the C$_{1-3}$alkyl may be further substituted with one or more halos;
R$_b$ is C$_{1-3}$alkyl;
or R$_a$ and R$_b$ together with the carbon atom they are attached form a C$_{3-6}$ cycloalkyl group;
or one of the carbon atoms in the C$_{3-6}$cycloalkyl group formed by R$_a$ and R$_b$ may be replaced with an oxygen to form an oxetane, tetrahydrofuryl or tetrahydropyranyl group;

or one of the carbon atoms in the $C_{3-6}$cycloalkyl group formed by $R_a$ and $R_b$ may be replaced by a nitrogen to form a dihydropyrroyl group which may be further substituted with $SO_2Me$, $C_{1-4}$ alkyl, or $C(O)C_{1-4}$ alkyl;

$R_x$ is hydrogen, dihydrofuryl, $C(O)OR_c$, $C(O)$—$(NR_dR_e)$, $OC_{1-4}$ alkyl, $CF_3$, CN, C(O)piperidinyl, $C_{1-4}$ alkyl, or —$OCF_3$;

$R_c$ is $C_{1-4}$ alkyl;

$R_d$ is $C_{1-4}$ alkyl or $C_{3-6}$ cycloalkyl;

$R_e$ is hydrogen or $C_{1-4}$ alkyl;

$R_f$ is hydrogen or $C_{1-3}$ alkyl;

n is 1, 2, or 3;

m is 0, 1, or 2;

y is 0, 1, or 2;

or a pharmaceutically acceptable salt thereof.

2. A compound of claim 1 wherein:

$R_1$ is hydrogen or $C_{1-3}$ alkyl;

$R_2$ is independently hydrogen, CN, $CF_3$, halo or $C_{1-3}$ alkyl;

$R_3$ is hydrogen, $C_{1-2}$ alkyl, $CF_3$ or —OH;

X is N;

A is $C_{1-6}$ alkyl unsubstituted or substituted by 1-5 substituents chosen from:
halo, $C_{1-3}$alkyl, $C_{3-6}$cycloalkyl, $Si(CH_3)_3$, CN, C≡CH, $OC_{1-3}$ alkyl, SMe, $CF_3$, $OCF_3$, $SCF_3$, $C(O)OR_c$, $C(O)(NR_dR_e)$, tetrahydrofuryl, tetrahydropyranyl, tetrahydropyrrolyl, or oxotetrahydropyrrolyl;
wherein the tetrahydrofuryl and tetrahydropyranyl may be further substituted with one or two $C_{1-3}$ alkyl groups;

or A is $C_{5-6}$cycloalkyl substituted by one or more $C_{1-3}$alkyl groups;

or A is $(CHR_f)_n$—$(CR_aR_b)$—$(CH_2)_m$—$R_x$;

$R_a$ is hydrogen or $C_{1-3}$alkyl; wherein the $C_{1-3}$alkyl may be further substituted with one or more halos;

$R_b$ is $C_{1-3}$alkyl;

or $R_a$ and $R_b$ together with the carbon atom they are attached form a $C_{3-6}$ cycloalkyl group;

or one of the carbon atoms in the $C_{3-6}$cycloalkyl group formed by $R_a$ and $R_b$ may be replaced with an oxygen to form an oxetane, tetrahydrofuryl or tetrahydropyranyl group;

or one of the carbon atoms in the $C_{3-6}$cycloalkyl group formed by $R_a$ and $R_b$ may be replaced by a nitrogen to form a dihydropyrroyl group which may be further substituted with $SO_2Me$, $C_{1-4}$ alkyl, or $C(O)C_{1-4}$ alkyl;

$R_x$ is hydrogen, dihydrofuryl, $C(O)OR_c$, $C(O)$—$(NR_dR_e)$, $OC_{1-4}$ alkyl, $CF_3$, CN, C(O)piperidinyl, $C_{1-4}$ alkyl, or —$OCF_3$;

$R_c$ is $C_{1-4}$ alkyl;

$R_d$ is $C_{1-4}$ alkyl or $C_{3-6}$ cycloalkyl;

$R_e$ is hydrogen or $C_{1-4}$ alkyl;

$R_f$ is hydrogen or $C_{1-3}$ alkyl;

n is 1, 2, or 3;

m is 0, 1, or 2;

y is 1 or 2;

or a pharmaceutically acceptable salt thereof.

3. A compound of claim 1 wherein:

$R_1$ is hydrogen or $C_{1-3}$ alkyl;

$R_2$ is independently hydrogen, CN, halo or $C_{1-3}$ alkyl;

$R_3$ is hydrogen;

X is N;

A is $C_{1-6}$ alkyl unsubstituted or substituted by 1-5 substituents chosen from:
halo, $C_{1-3}$alkyl, $C_{3-6}$cycloalkyl, $Si(CH_3)_3$, CN, C≡CH, $OC_{1-3}$alkyl, SMe, $CF_3$, $OCF_3$, $SCF_3$, $C(O)OR_c$, $C(O)(NR_dR_e)$, tetrahydrofuryl, tetrahydropyranyl, tetrahydropyrrolyl, or oxotetrahydropyrrolyl;
wherein the tetrahydrofuryl and tetrahydropyranyl may be further substituted with one or two $C_{1-3}$ alkyl groups;

or A is $(CHR_f)_n$—$(CR_aR_b)$—$(CH_2)_m$—$R_x$;

$R_a$ is hydrogen or $C_{1-3}$alkyl; wherein the $C_{1-3}$alkyl may be further substituted with one or more halos;

$R_b$ is $C_{1-3}$alkyl;

or $R_a$ and $R_b$ together with the carbon atom they are attached form a $C_{3-6}$ cycloalkyl group;

or one of the carbon atoms in the $C_{3-6}$cycloalkyl group formed by $R_a$ and $R_b$ may be replaced with an oxygen to form an oxetane, tetrahydrofuryl or tetrahydropyranyl group;

or one of the carbon atoms in the $C_{3-6}$cycloalkyl group formed by $R_a$ and $R_b$ may be replaced by a nitrogen to form a dihydropyrroyl group which may be further substituted with $SO_2Me$, $C_{1-4}$ alkyl, or $C(O)C_{1-4}$ alkyl;

$R_x$ is hydrogen, dihydrofuryl, $C(O)OR_c$, $C(O)$—$(NR_dR_e)$, $OC_{1-4}$ alkyl, $CF_3$, CN, C(O)piperidinyl, $C_{1-4}$ alkyl, or —$OCF_3$;

$R_c$ is $C_{1-4}$ alkyl;

$R_d$ is $C_{1-4}$ alkyl or $C_{3-6}$ cycloalkyl;

$R_e$ is hydrogen or $C_{1-4}$ alkyl;

$R_f$ is hydrogen or $C_{1-3}$ alkyl;

n is 1;

m is 0 or 1; and y is 1 or 2;

or a pharmaceutically acceptable salt thereof.

4. A compound of claim 1 chosen from:

1-(((5S,7S)-7-methyl-3-neopentyl-2-oxo-1-oxa-3-azaspiro[4.5]decan-7-yl)methyl)-1H-benzo[d]imidazole-6-carbonitrile;

1-(((5S,7S)-3-neopentyl-2-oxo-1-oxa-3-azaspiro[4.5]decan-7-yl)methyl)-1H-benzo[d]imidazole-6-carbonitrile;

1-(((5S,7S)-2-oxo-3-((trimethylsilyl)methyl)-1-oxa-3-azaspiro[4.5]decan-7-yl)methyl)-1H-benzo[d]imidazole-6-carbonitrile;

1-(((5S,7S)-3-((1-(methoxymethyl)cyclopentyl)methyl)-2-oxo-1-oxa-3-azaspiro[4.5]decan-7-yl)methyl)-1H-benzo[d]imidazole-6-carbonitrile;

1-(((5S,7S)-3-((1-ethylcyclobutyl) methyl)-2-oxo-1-oxa-3-azaspiro[4.5]decan-7-yl)methyl)-1H-benzo[d]imidazole-6-carbonitrile;

1-(((5S,7S)-3-((2-methyltetrahydrofuran-2-yl)methyl)-2-oxo-1-oxa-3-azaspiro[4.5]decan-7yl)methyl)-1H-benzo[d]imidazole-6-carbonitrile;

1-(((5S,7S)-7-methyl-3-((2-methyltetrahydrofuran-2-yl)methyl)-2-oxo-1-oxa-3-azaspiro[4.5]decan-7-yl)methyl)-1H-benzo[d]imidazole-6-carbonitrile;

1-(((5S,7S)-3-((2-ethyltetrahydrofuran-2-yl)methyl)-2-oxo-1-oxa-3-azaspiro[4.5]decan-7-yl)methyl)-1H-benzo[d]imidazole-6-carbonitrile;

1-(((5S,7S)-7-methyl-2-oxo-3-(((S)-tetrahydrofuran-2-yl)methyl)-1-oxa-3-azaspiro[4.5]decan-7-yl)methyl)-1H-benzo[d]imidazole-6-carbonitrile;

1-(((5S,7S)-3-(2-ethoxy-2-methylpropyl)-2-oxo-1-oxa-3-azaspiro[4.5]decan-7-yl)methyl)-1H-benzo[d]imidazole-6-carbonitrile;

1-(((5S,7S)-3-((2-methyltetrahydro-2H-pyran-2-yl)methyl)-2-oxo-1-oxa-3-azaspiro[4.5]decan-7-yl)methyl)-1H-benzo[d]imidazole-6-carbonitrile;

1-(((5S,7S)-3-(3-isopropoxy-2,2-dimethylpropyl)-2-oxo-1-oxa-3-azaspiro[4.5]decan-7-yl)methyl)-1H-benzo[d]imidazole-6-carbonitrile;

1-(((5S,7S)-3-(2-cyano-2-methylpropyl)-2-oxo-1-oxa-3-azaspiro[4.5]decan-7-yl)methyl)-1H-benzo[d]imidazole-6-carbonitrile;

1-(((5S,7S)-3-(2,2-dimethyl-3-(trifluoromethoxy)propyl)-2-oxo-1-oxa-3-azaspiro[4.5]decan-7yl)methyl)-1H-benzo[d]imidazole-6-carbonitrile;

1-(((5S,7S)-3-(2,2-dimethylcyclohexyl)-2-oxo-1-oxa-3-azaspiro[4.5]decan-7-yl)methyl)-1H-benzo[d]imidazole-6-carbonitrile;

methyl 3-(-7-((6-cyano-1H-benzo[d]imidazol-1-yl)methyl)-2-oxo-1-oxa-3-azaspiro[4.5]decan-3-yl)-2,2-dimethylpropanoate;

5-fluoro-1-((-2-oxo-3-(2,2,3,3,3-pentafluoropropyl)-1-oxa-3-azaspiro[4.5]decan-7-yl)methyl)-1H-benzo[d]imidazole-6-carbonitrile;

7-((6-chloro-1H-benzo[d]imidazol-1-yl)methyl)-7-methyl-3-neopentyl-1-oxa-3-azaspiro[4.5]decan-2-one;

7-((5,6-dichloro-1H-benzo[d]imidazol-1-yl)methyl)-7-methyl-3-neopentyl-1-oxa-3-azaspiro[4.5]decan-2-one;

7-((5,6-difluoro-1H-benzo[d]imidazol-1-yl)methyl)-7-methyl-3-neopentyl-1-oxa-3-azaspiro[4.5]decan-2-one;

7-((5,6-dimethoxy-1H-benzo[d]imidazol-1-yl)methyl)-7-methyl-3-neopentyl-1-oxa-3azaspiro[4.5]decan-2-one;

7-((5,6-dimethyl-1H-benzo[d]imidazol-1-yl)methyl)-7-methyl-3-neopentyl-1-oxa-3azaspiro[4.5]decan-2-one;

3-neopentyl-7-((6-(trifluoromethyl)-1 H-benzo[d]imidazol-1-yl)methyl)-1-oxa-3-azaspiro[4.5]decan-2-one;

2-ethyl-1-((-7-methyl-3-neopentyl-2-oxo-1-oxa-3-azaspiro[4.5]decan-7-yl)methyl)-1H-benzo[d]imidazole-6-carbonitrile;

5-chloro-1-((3-(2,2-dimethylpropyl)-2-oxo-1-oxa-3-azaspiro[4.5]dec-7-yl)methyl)-1H-benzimidazole-6-carbonitrile;

4-chloro-1-((-3-((4-methyltetrahydro-2H-pyran-4-yl)methyl)-2-oxo-1-oxa-3-azaspiro[4.5]decan-7-yl)methyl)-1H-benzo[d]imidazole-6-carbonitrile;

1-((-3-((4-ethyltetrahydro-2H-pyran-4-yl)methyl)-2-oxo-1-oxa-3-azaspiro[4.5]decan-7-yl)methyl)-1H-benzo[d]imidazole-6-carbonitrile;

1-((-3-(2-methylbutyl)-2-oxo-1-oxa-3-azaspiro[4.5]decan-7-yl)methyl)-1H-benzo[d]imidazole-6-carbonitrile;

5-fluoro-1-((-3-neopentyl-2-oxo-1-oxa-3-azaspiro[4.5]decan-7-yl)methyl)-1H-benzo[d]imidazole-6-carbonitrile;

4-fluoro-1-((-3-neopentyl-2-oxo-1-oxa-3-azaspiro[4.5]decan-7-yl)methyl)-1H-benzo[d]imidazole-6-carbonitrile;

4-chloro-1-((-7-methyl-3-neopentyl-2-oxo-1-oxa-3-azaspiro[4.5]decan-7-yl)methyl)-1H-benzo[d]imidazole-6-carbonitrile;

1-((-7-ethyl-3-neopentyl-2-oxo-1-oxa-3-azaspiro[4.5]decan-7-yl)methyl)-1H-benzo[d]imidazole-6-carbonitrile;

{[3-(2,2-dimethylpropyl)-2-oxo-1-oxa-3-azaspiro[4.5]dec-7-yl]methyl}-1H-benzoimidazole-6-carbonitrile-d2;

4-chloro-1-(((5S,7S)-3-neopentyl-2-oxo-1-oxa-3-azaspiro[4.5]decan-7-yl)methyl)-1H-benzo[d]imidazole-6-carbonitrile;

4-bromo-1-((-3-neopentyl-2-oxo-1-oxa-3-azaspiro[4.5]decan-7-yl)methyl)-1H-benzo[d]imidazole-6-carbonitrile;

4-methoxy-1-((-3-neopentyl-2-oxo-1-oxa-3-azaspiro[4.5]decan-7-yl)methyl)-1H-benzo[d]imidazole-6-carbonitrile;

5-fluoro-1-((-3-((2-methyltetrahydrofuran-2-yl)methyl)-2-oxo-1-oxa-3-azaspiro[4.5]decan-7-yl)methyl)-1H-benzo[d]imidazole-6-carbonitrile;

5-fluoro-1-((-3-(3-methoxy-2,2-dimethylpropyl)-2-oxo-1-oxa-3-azaspiro[4.5]decan-7-yl)methyl)-1H-benzo[d]imidazole-6-carbonitrile;

1-(((5S,7S)-3-((2-ethyltetrahydro-2H-pyran-2-yl)methyl)-2-oxo-1-oxa-3-azaspiro[4.5]decan-7-yl)methyl)-1H-benzo[d]imidazole-6-carbonitrile;

1-(((5S,7S)-3-(3-ethoxy-2,2-dimethylpropyl)-2-oxo-1-oxa-3-azaspiro[4.5]decan-7-yl)methyl)-1 H-benzo[d]imidazole-6-carbonitrile;

4-chloro-1-(((5S,7S)-3-((2-methyltetrahydrofuran-2-yl)methyl)-2-oxo-1-oxa-3-azaspiro[4.5]decan-7-yl)methyl)-1H-benzo[d]imidazole-6-carbonitrile;

7-((6-chloro-5-fluoro-1H-benzo[d]imidazol-1-yl)methyl)-3-((2-methyltetrahydrofuran-2-yl)methyl)-1-oxa-3-azaspiro[4.5]decan-2-one;

1-(((5S,7S)-2-oxo-3-((tetrahydro-2H-pyran-2-yl)methyl)-1-oxa-3-azaspiro[4.5]decan-7-yl)methyl)-1H-benzo[d]imidazole-6-carbonitrile;

5-fluoro-1-((-3-((1-(methoxymethyl)cyclopropyl)methyl)-2-oxo-1-oxa-3-azaspiro[4.5]decan-7-yl)methyl)-1H-benzo[d]imidazole-6-carbonitrile;

1-(((5S,7S)-3-(3-methoxy-2,2-dimethylpropyl)-2-oxo-1-oxa-3-azaspiro[4.5]decan-7-yl)methyl)-1H-benzo[d]imidazole-6-carbonitrile;

1-(((5S,7S)-3-((4-(methoxymethyl)tetrahydro-2H-pyran-4-yl)methyl)-2-oxo-1-oxa-3-azaspiro[4.5]decan-7-yl)methyl)-1H-benzo[d]imidazole-6-carbonitrile;

(5S,7S)-3-(3-methoxy-2,2-dimethylpropyl)-7-((6-(trifluoromethyl)-1H-benzo[d]imidazol-1-yl)methyl)-1-oxa-3-azaspiro[4.5]decan-2-one;

1-(((5S,7S)-2-oxo-3-(2,2,3,3,3-pentafluoropropyl)-1-oxa-3-azaspiro[4.5]decan-7-yl)methyl)-1H-benzo[d]imidazole-6-carbonitrile;

1-(((5S,7S)-3-(2-methoxy-2-methylpropyl)-2-oxo-1-oxa-3-azaspiro[4.5]decan-7-yl)methyh-1H-benzo[d]imidazole-6-carbonitrile;

4-chloro-1-(((5S,7S)-2-oxo-3-(((S)-tetrahydrofuran-2-yl)methyl)-1-oxa-3-azaspiro[4.5]decan-7-yl)methyl)-1H-benzo[d]imidazole-6-carbonitrile;

1-(((5S,7S)-3-((1-methylcyclobutyl)methyl)-2-oxo-1-oxa-3-azaspiro[4.5]decan-7-yl)methyl)-1H-benzo[d]imidazole-6-carbonitrile;

1-{[(5S,7S)-3-(2,2-dimethylpropyl)-2-oxo-1-oxa-3-azaspiro[4.5]dec-7-yl]methyl}-1H-benzimidazole-6-carbonitrile-d2;

1-(((5S,7S)-3-(2,2-dimethylbutyl)-2-oxo-1-oxa-3-azaspiro[4.5]decan-7-yl)methyl)-1H-benzo[d]imidazole-6-carbonitrile;

1-(((5S,7S)-3-((S)-2-methylbutyl)-2-oxo-1-oxa-3-azaspiro[4.5]decan-7-yl)methyl)-1H-benzo[d]imidazole-6-carbonitrile;

1-(((5S,7S)-3-(cyclopentylmethyl)-2-oxo-1-oxa-3-azaspiro[4.5]decan-7-yl)methyl)-1H-benzo[d]imidazole-6-carbonitrile;

4-methyl-1-((-3-neopentyl-2-oxo-1-oxa-3-azaspiro[4.5]decan-7-yl)methyl)-1H-benzo[d]imidazole-6-carbonitrile;

1-{[(5S,7S)-7-methyl-3-(2-methylpropyl)-2-oxo-1-oxa-3-azaspiro[4.5]dec-7-yl]methyl}1-1H-benzimidazole-6-carbonitrile;

or a pharmaceutically acceptable salt thereof.

5. A pharmaceutical composition comprising a compound of claim 1 and a pharmaceutically acceptable carrier or excipient.

6. A method of treating congestive heart failure, overactive bladder, pain, cardiovascular disease, motor neuron disorders, or osteoarthritis, which comprises administering to a human in need thereof, a compound of claim 1.

7. A method according to claim 6 wherein the compound is administered orally.

8. A method according to claim 6 wherein the compound is administered intravenously.

9. A method according to claim 6 wherein the compound is administered by inhalation.

* * * * *